(12) United States Patent
Sukhatme et al.

(10) Patent No.: US 10,550,186 B2
(45) Date of Patent: Feb. 4, 2020

(54) CANCER THERAPY TARGETING INTERCELLULAR ADHESION MOLECULE 4 (ICAM4)

(71) Applicant: Beth Israel Deaconess Medical Center, Inc., Boston, MA (US)

(72) Inventors: Vikas P. Sukhatme, Newton, MA (US); Zaheed Husain, Medford, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/532,844

(22) PCT Filed: Dec. 2, 2015

(86) PCT No.: PCT/US2015/063347
§ 371 (c)(1),
(2) Date: Jun. 2, 2017

(87) PCT Pub. No.: WO2016/089950
PCT Pub. Date: Jun. 9, 2016

(65) Prior Publication Data
US 2017/0362320 A1 Dec. 21, 2017

Related U.S. Application Data

(60) Provisional application No. 62/087,433, filed on Dec. 4, 2014.

(51) Int. Cl.
| | | |
|---|---|---|
| *A61K 41/00* | (2006.01) | |
| *A61K 51/00* | (2006.01) | |
| *G01N 33/53* | (2006.01) | |
| *C07K 16/28* | (2006.01) | |
| *G01N 33/574* | (2006.01) | |
| *A61K 39/395* | (2006.01) | |
| *A61K 47/68* | (2017.01) | |
| *A61K 45/06* | (2006.01) | |
| *C07K 16/30* | (2006.01) | |
| *G01N 33/569* | (2006.01) | |

(52) U.S. Cl.
CPC .... *C07K 16/2821* (2013.01); *A61K 39/39558* (2013.01); *A61K 45/06* (2013.01); *A61K 47/6851* (2017.08); *C07K 16/30* (2013.01); *G01N 33/56966* (2013.01); *G01N 33/57492* (2013.01); *C07K 2317/21* (2013.01); *C07K 2317/24* (2013.01); *C07K 2317/31* (2013.01); *G01N 2333/70525* (2013.01); *G01N 2500/10* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| | | |
|---|---|---|
| 5,773,293 A | 6/1998 | Kilgannon et al. |
| 8,883,497 B2 | 11/2014 | Epstein et al. |
| 2011/0059106 A1 | 3/2011 | Kuchroo et al. |
| 2012/0156280 A1 | 6/2012 | Dow et al. |
| 2017/0044127 A1* | 2/2017 | Wei ...................... C07D 311/62 |

OTHER PUBLICATIONS

Lechner et al. A new mechanism for blocking myeloid-derived suppressor cells by CpG. Clin Cancer Res. Apr. 1, 2011; 17(7): 1645-1648 . (Year: 2011).*
DeVeirman et al Myeloid-derived suppressor cells as therapeutic target in hematol. Front Oncol. Dec. 8, 2014;4:349. (Year: 2014).*
Kammerer et al. Large-Scale Association Study Identifies ICAM Gene Region as Breast and Prostate Cancer Susceptibility Locus. Cancer Research 64, 8906-8910, Dec. 15, 2004. (Year: 2004).*
Almand et al., "Increased Production of Immature Myeloid Cells in Cancer Patients: A Mechanism of Immunosuppression in Cancer," J Immunol. 166(1):678-689, 2001.
Antonia et al., "Immuno-oncology Combinations: A Review of Clinical Experience and Future Prospects," Clin Cancer Res, Dec. 15, 2014, 20(24):6258-6268.
Apweiler et al., "UniProt: The Universal Protein knowledgebase." Nucleic Acids Research, Jan. 1, 2004, 32:D115-D119.
Benjamin et al., "Controlling the false discovery rate: a practical and powerful approach to multiple testing." J R Stat Soc Series B Jan. 1, 1995, 57(1):289-300.
Bronte et al., "Regulation of immune responses buy L-arginine metabolism." Nat. Rev. Immunol. Aug. 1, 2005, 5:641-654.
Bronte et al., "Tumor-induced immune dysfunctions caused by myeloid suppressor cells. J Immunother." Nov. 1, 2001, 24:431-446.
Carrero et al., "IL1β induces mesenchymal stem cells migration and leucocyte chemotaxis through NF-κB." Stem Cell Rev and Rep. Sep. 1, 2012, 8(3):905-916.
Cerdeira et al., "Conversion of peripheral blood NK cells to a decidual NK-like phenotype by a cocktail of defined factors." J. Immunol. Apr. 15, 2013, 190(8):3939-3948.
Clark et al., "Dynamics of the immune reaction to pancreatic cancer from inception to invasion." Oct. 1, 2007, Cancer Res. 67:9518-9527.
Diaz-Montero et al., "Increased circulating myeloid-derived suppressor cells correlate with clinical cancer stage, metastatic tumor burden, and doxorubicincyclophosphamide chemotherapy," Cancer Immunol. Immunother. Jan. 1, 2009, 58(1):49-59.
Donkor et al., "Mammary tumor heterogeneity in the expansion of myeloid-derived suppressor cells," Int. Immunopharmacology, Jul. 31, 2009, 9:937-948.

(Continued)

*Primary Examiner* — Maher M Haddad
(74) *Attorney, Agent, or Firm* — Fish & Richardson P.C.

(57) ABSTRACT

Methods for treating cancer, e.g., in conjunction with anti-cancer therapy, like immunotherapy, and for identifying candidate therapeutic agents, by targeting ICAM4. While MDSCs in mice have been extensively characterized, their human counterparts are not well defined, and cell markers present in mice are not always usable in humans. MDSCs have been described as a heterogenous population of myeloid derived cells with immune suppressive capacity (5, 9, 40, 41). Recent renewed interest in the role of MDSC accumulation in human tumors has resulted in the increased need to define these cells better in order to target them for therapeutic intervention.

4 Claims, 31 Drawing Sheets

(56) References Cited

OTHER PUBLICATIONS

Egan et al., "Understanding the multiple functions of Gr-1(+) cell subpopulations during microbial infection." Immunol. Res., Jan. 1, 2008, 40(1):35-48.
Filipazzi et al., "Identification of a new subset of myeloid suppressor cells in peripheral blood of melanoma patients with modulation by a granulocyte-macrophage colony-stimulation factor-based antitumor vaccine." Jun. 20, 2007, J Clin. Oncol. 25(18):2546-2553.
Gabitass et al., "Elevated myeloid-deprived suppressor cells in pancreatic, esophageal and gastric cancer are an independent prognostic factor and are associated with significant elevation of the Th2 cytokine interleukin-13," Oct. 1, 2011, Cancer Imrnunol Immunother. 60(10):1419-1430 (2011).
Gabrilovich et al., "Myeloid-derived suppressor cells as regulators of the immune system." Nat. Rev. Immunol., Mar. 1, 2009, 9:162-174.
Gabrilovich et al., "Mechanism of immune dysfunction in cancer mediated by immature Gr-1+ myeloid cells." The Journal of Immunology. May 1, 2001, 166(9):5398-406.
Gabrilovich et al., "Coordinated regulation of myeloid cells by tumours-." Nat. Rev. Immunol. Apr. 1, 2012, 12(4):253-268.
Gallina et al., "Tumors induce a subset of inflammatory monocytes with immunosuppressive activity on CD8+ T cells." J Clin. Invest. Oct. 2, 2006, 116(10):2777-2790.
Gottfried et al., "Tumor-induced modulation of dendritic cell function." Cytokine Growth Factor Rev., Feb. 29, 2008, 19(1):65-77.
Greifenberg et al., "Myeloid-derived suppressor cell activation by combined LPS and IFN-gamma treatment impairs DC development." Eur. J Immunol. Oct. 1, 2009, 39(10):2865-2876.
Greten et al., "Myeloid derived suppressor cells in human disease." Int. Immunopharmacol. Jul. 31, 2011, 11(7):802-807.
Haile et al., "Immune suppression: the hallmark of myeloid derived suppressor cells." Immunol. Invest., Aug. 1, 2012, 41(6-7):581-594.
Hermand et al., "Red cell ICAM-4 is a novel ligand for platelet activated alpha IIbbeta 3 integrin." J Biol. Chem., Feb. 14, 2003, 278(7):4892-4898.
Huang et al., "Gr-1+CD115+ immature myeloid suppressor cells mediate the development of tumor-induced T regulatory cells and T-cell anergy in tumor-bearing host." Cancer Res., Jan. 15, 2006, 66:1123-1131.
Husain et al., "Tumor-derived lactate and myeloid-derived suppressor cells: Linking metabolism to cancer immunology." Oncoimmunology, Nov. 1, 2013, 2(11):e26383, 3 pages.
Husain et al., "Tumor-derived lactate modifies antitumor immune response: effect on myeloid-derived suppressor cells and NK cells." J. Immunol., Aug. 1, 2013, 191(3):1486-1495.
Iida et al., "Commensal bacteria control cancer response to therapy by modulating the tumor microenvironment." Science, Nov. 22, 2013, 342(6161):967-970.
International Preliminary Report on Patentability in International Application No. PCT/US2015/063347, dated Jun. 6, 2017, 7 pages.
International Search Report and Written Opinion in International Application No. PCT/US2015/063347, dated Feb. 9, 2016, 10 pages.
Kammerer et al., "Large-scale association study identifies ICAM gene region as breast and prostate cancer susceptibility locus." Cancer Res., Dec. 15, 2004, 64(24):8906-8910.
Kao et al., "Targeting immune suppressing myeloid-derived suppressor cells in oncology." Crit. Rev. Oncol. Hematol., Jul. 31, 2011, 77(1):12-19.
Kohanbash et al., "Myeloid-derived suppressor cells (MDSCs) in gliomas and glioma-development." Immunol Invest., Jan. 1, 2012, 41(6-7):658-79.
Kusmartsev et al., "Reversal of myeloid cell-mediated immunosuppression in patients with metastatic renal carcinoma." Clin. Cancer Res., Dec. 18, 2008, 14:8270-8278.
LaFace et al., "Meeting report: regulatory myeloid cells." Int. Immunopharmacol., Jul. 31, 2011, 7:780-782.
Lechner et al., "Characterization of cytokine-induced myeloid-derived suppressor cells from normal human peripheral blood mononuclear cells." J Immunol., Aug. 15, 2010, 185(4):2273-2278.
Liu et al., "Population alterations of L-arginase- and inducible nitric oxide synthase-expressed CD1 lb+/CD14-/CD15+/CD33+ myeloid-derived suppressor cells and CD8+ T lymphocytes in patients with advanced-stage non-small cell lung cancer." J Cancer Res. Clin. Oncol., Jan. 1, 2010, 136(1):35-45.
Ma et al., "Anti-Gr-I antibody depletion fails to eliminate hepatic myeloid-derived suppressor cells in tumor-bearing mice." J Leukoc Biol., Dec. 1, 2012, 92(6):1199-1206.
Marigo, et al., "Tumor-induced tolerance and immune suppression by myeloid derived suppressor cells." Immunol. Rev., Apr. 1, 2008, 222:162-179.
Markowitz et al., "Myeloid-derived suppressor cells in breast cancer." Breast Cancer Res Treat., Jul. 1, 2013, 140(1):13-21.
Mielcarek et al., "Suppression of alloantigen-induced T-cell proliferation by CD14+ cells derived from granulocyte colony-stimulating factor-mobilized peripheral blood mononuclear cells." Blood, Mar. 1, 1997, 89(5):1629-1634.
Mirza et al., "All-trans-retinoic acid improves differentiation of myeloid cells and immune response in cancer patients." Cancer Res., Sep. 15, 2006, 66:9299-9307.
Mundy-Bosse et al., "Myeloid-Derived suppressor cell inhibition of the IFN response in tumor-bearing mice." Cancer Res., Aug. 1, 2011, 71(15):5101-5110.
Nagaraj et al., "Regulation of suppressive function of myeloid-derived suppressor cells by CD4+ T cells." Semin. Cancer Biol., Aug. 31, 2012, 22(4):282-288.
Najjar et al., "Clinical perspectives on targeting of myeloid derived suppressor cells in the treatment of cancer." Front. Oncol., Mar. 15, 2013, 3(49):1-9.
Ostrand-Rosenberg et al., "Myeloid-derived suppressor cells: more mechanisms for inhibiting antitumor activity." Cancer Immunol. Immunother., Oct. 2010, 59(10):1593-1600.
Ostrand-Rosenberg et al., "Myeloid-derived suppressor cells: linking inflammation and cancer." J. Imrnunol., Apr. 15, 2009, 182(8):4499-4506.
Pan et al., "Immune stimulatory receptor CD40 is required for Tcell suppression and T regulatory cell activation mediated by myeloid-derived suppressor cells in cancer." Cancer Res., Jan. 1, 2010, 70(1):99-108.
Peranzoni et al., "Myeloid-derived suppressor cell heterogeneity and subset definition." Curr Opinion Immunol., Apr. 30, 2010. 22(2):238-244.
Porembka et al., "Pancreatic adenocarcinoma induces bone marrow mobilization of myeloid-derived suppressor cells which promote primary tumor growth." Cancer Immunol. Immunother., Sep. 1, 2012, 61(9):1373-1385.
Ribechini et al., "Subsets, expansion and activation of myeloid-derived suppressor cells." Med. Microbiol. Immunol., Aug. 1, 2010, 199(3):273-281.
Rosenzweig et al., "Development of TRX518, an aglycosyl humanized monoclonal antibody (Mab) agonist of huGITR." J Clin Oncol., May 20, 2010, 28(15_suppl):e13028.
Schaer et al., "Anti-GITR antibodies—potential clinical applications for tumor immunotherapy." Curr Opin Investig Drugs. Dec. 2010, 11(12):1378-1386.
Serafini et al., "Myeloid-derived suppressor cells promote cross-tolerance in B-cell lymphoma by expanding regulatory T cells." Cancer Res., Jul. 1, 2008, 68:5439-5449.
Shurin et al., "Intratumoral cytokines/chemokines/growth factors and tumor infiltrating dendritic cells: friends or enemies?" Cancer Matastasis Rev., Sep. 1, 2006, 25(3):333-356.
Singh et al., "Fas-FasL-mediated CD4+ T-cell apoptosis following stem cell transplantation." Cancer Res., Jul. 1, 1999, 59(13):3107-3111.
Smyth "Linear models and empirical bayes methods for assessing differential expression in microarray experiments." Stat. Appl. Genet. Mol. Biol., Feb. 12, 2004, 3(1):1-25.
Stewart et al., "Improving cancer immunotherapy by targeting tumor-induced immune suppression," Cancer Metastasis Rev., Mar. 2011, 30(1):125-140.

(56) References Cited

OTHER PUBLICATIONS

Talmadge et al., "History of myeloid-derived suppressor cells." Nat. Rev. Cancer., Sep. 24, 2013, 13(10):739-752.

Talmadge et al., "Immunologic attributes of cytokine mobilized peripheral blood stem cells and recovery following transplantation." Bone Marrow Transplant., Jan. 1, 1996 17(1):101-109.

Terabe et al., "Transforming growth factor-b production and myeloid cells are an effector mechanism through which Cd 1d restricted T cells block cytotoxic T lymphocyte-mediated tumor immunosurveillance: abrogation prevents tumor recurrence." J Exp. Med., Dec. 1, 2003, 198(11):1741-1752.

Ugel et al., "Therapeutic targeting of myeloid-derived suppressor cells." Curr. Opin. Pharmacol., Aug. 31, 2009, 9(4):470-481.

van Cruijsen et al., "Sunitinib-induced myeloid lineage redistribution in renal cell cancer patients: CD 1 c+ dendritic cell frequency predicts progression-free survival." Clin. Cancer Res., Sep. 15, 2008, 14(18):5884-5892.

Vieweg et al., "Reversal of tumor mediated immunosuppression." Clin. Cancer Res Jan. 15, 2007, 13(2):727s-732s.

Wang et al., "Increased myeloid-derived suppressor cells in gastric cancer correlate with cancer stage and plasma S100A8/A9 proinflammatory proteins." J. Immunol., Jan. 15, 2013, 190(2):794-804.

Wesolowski et al., "Myeloid derived suppressor cells—a new therapeutic target in the treatment of cancer," Journal for ImmunoTherapy of Cancer, Jul. 15, 2013, 1(10):1-11.

Yang et al., "CD80 in immune suppression by mouse ovarian carcinoma-associated Gr-1+CD11b+ myeloid cells." Cancer Res., Jul. 1, 2006, 66(13):6807-6815.

Youn et al., "The biology of myeloid-derived suppressor cells: the blessing and the curse of morphological and functional heterogeneity." Eur. J Immunol., Nov. 1, 2010, 40(11):2969-2975.

Youn et al., "Subsets of myeloid-derived suppressor cells in tumor-bearing mice." J Immunol., Oct. 15, 2008, 181(8):5791-5802.

Young et al., "Hematopoiesis and suppressor bone marrow cells in mice bearing large metastatic Lewis lung carcinoma tumors." Cancer Res., Jan. 1, 1987, 47(1):100-105.

Younos et al., "Tumor regulation of myeloid-derived suppressor cell proliferation and trafficking." Int. Immunopharmacol., Jul. 31, 2012, 13(3):245-256.

Yuk-Pavlović et al., "Immunosuppressive CD14+HLA-DRlow/-monocytes in prostate cancer," Prostate, Mar. 1, 2010, 70(4):443-455.

Zea et al., "Arginase-producing myeloid suppressor cells in renal cell carcinoma patients: a mechanism of tumor evasion." Cancer Res., Apr. 15, 2005, 65(8):3044-3048.

Zhang et al., "Circulating and Tumor-Infiltrating Myeloid-Derived Suppressor Cells in Patients with Colorectal Carcinoma" PLoS One. Feb. 2013, 8(2):e57114.

Zhao et al., "S100A9 a new marker for monocytic human myeloid derived suppressor cells." Immunology, Jun. 1, 2012, 136(2):176-183.

Zhao et al., "Increase in frequency of myeloid-derived suppressor cells in mice with spontaneous pancreatic carcinoma." Immunology, Sep. 1, 2009, 128(1):141-149.

\* cited by examiner

Her2 induced tumor

Her2 de-induced tumor

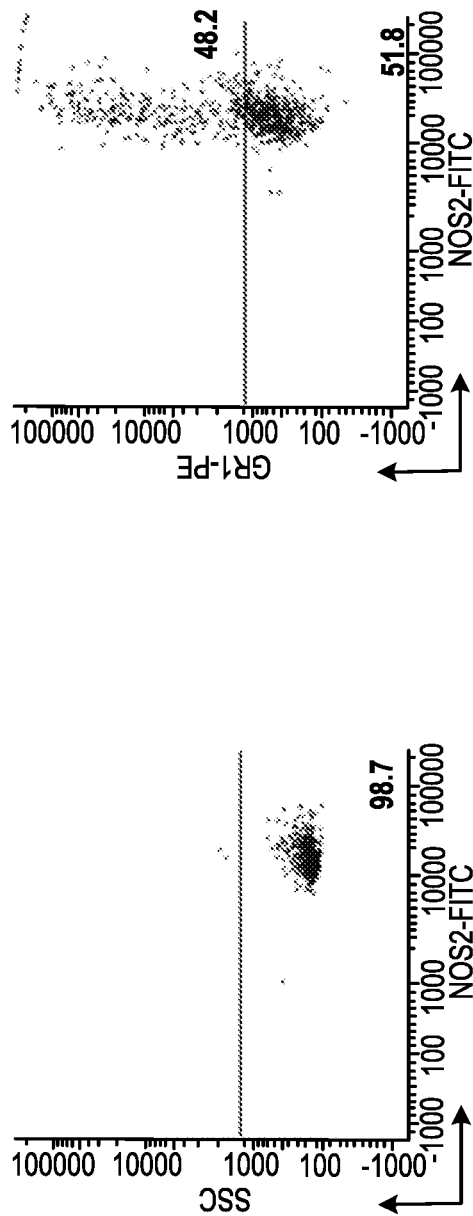
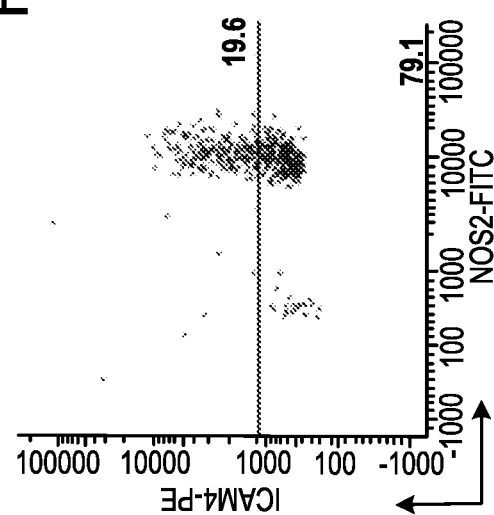
FIG. 10A
FIG. 10B
FIG. 10C

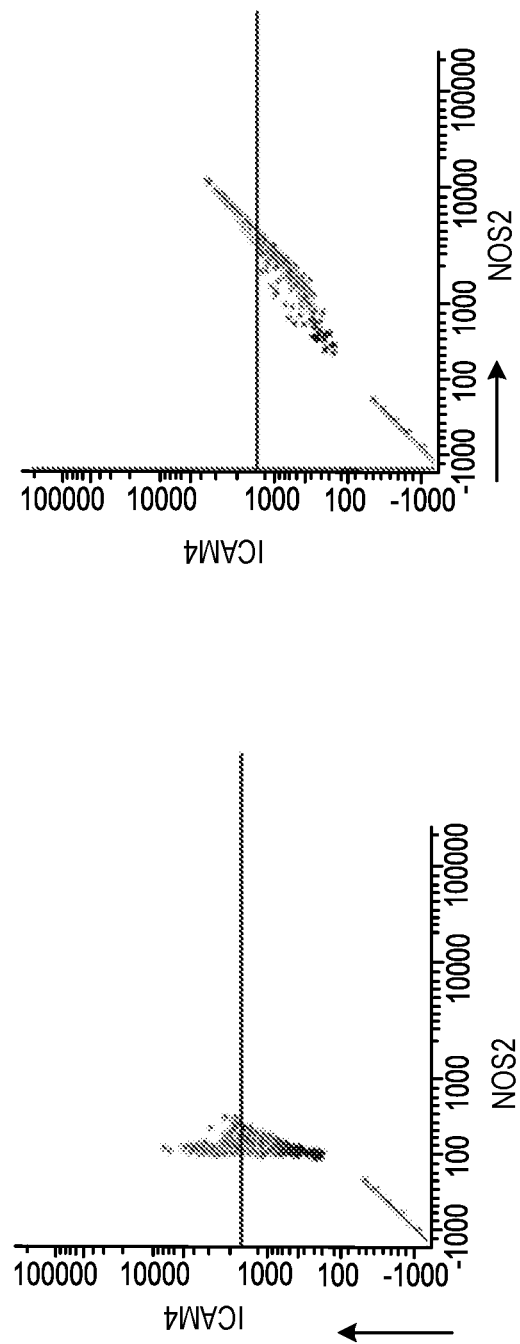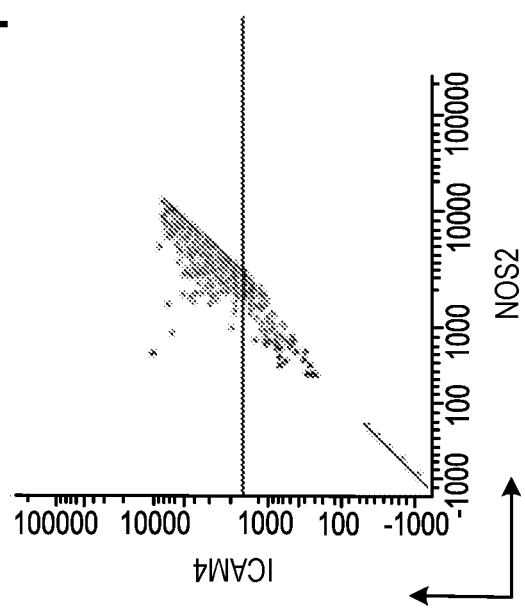

ICAM4

Q14773|23-240|, Intercellular adhesion molecule 4, Homo sapiens

```
         10         20         30         40         50         60
  MGSLFPLSLL FFLAAAYPGV GSALGRRTKR AQSPKGSPLA PSGTSVPFWF RMSPEFVAVQ
         70         80         90        100        110        120
  PGKSVQLNCS NSCPQPQNSS LRTPLRQGKT LRGPGWVSYQ LLDVRAWSSL AHCLVTCAGK
        130        140        150        160        170        180
  TRWATSRITA YKPPHSVILE PPVLKGRKYT LRCHVTQVFP VGYLVTLRH GSRVIYSESL
        190        200        210        220        230        240
  ERFTGLDLAN VTLTYEFAAG PRDFWQPVIC HARLNLDGLV VRNSSAPITL MLAWSPAPTA
        250        260        270
  LASGSIAALV GILLTVGAAY LLCKCLAMKSQ A
```

Extracellular domain: aa 23-240

Yellow regions represent extracellular domain

Pairwise Alignment Scores

| Gene | | Identity (%) | |
|---|---|---|---|
| Species | Symbol | Protein | DNA |
| H. sapiens | ICAM4 | | |
| vs. P. troglodytes | ICAM4 | 97.9 | 98.6 |
| vs. C. lupus | ICAM4 | 71.9 | 79.4 |
| vs. M. musculus | ICAM4 | 70.0 | 74.3 |

FIG. 18

CANCER THERAPY TARGETING INTERCELLULAR ADHESION MOLECULE 4 (ICAM4)

CROSS-REFERENCE TO RELATED APPLICATIONS

This application is a U.S. National Phase Application under 35 U.S.C. § 371 of International Patent Application No. PCT/US2015/063347, filed on Dec. 2, 2015, which claims the benefit of U.S. Application No. 62/087,433, filed on Dec. 4, 2014. The entire contents of the foregoing are hereby incorporated by reference.

TECHNICAL FIELD

The present invention relates to methods for treating cancer, e.g., in conjunction with other anti-cancer therapies, and for identifying candidate therapeutic agents, by targeting ICAM4.

BACKGROUND

Tumor-mediated immunosuppression prevents effective cancer immunotherapy. Tolerance to immune effectors in cancer development is partly achieved by the development of suppressor cell populations that infiltrate the tumor environment and migrate to metastatic niches. To date, the best characterized of such populations include regulatory T cells (Tregs), myeloid derived suppressor cells (MDSCs), and M2 polarized macrophages. Thus, MDSCs are a major cell type utilized by tumors to escape immune surveillance.

SUMMARY

While MDSCs in mice have been extensively characterized, their human counterparts are not well defined, and cell markers present in mice are not always usable in humans. MDSCs have been described as a heterogeneous population of myeloid derived cells with immune suppressive capacity (5, 9, 40, 41). Recent renewed interest in the role of MDSC accumulation in human tumors has resulted in the increased need to define these cells better in order to target them for therapeutic intervention. While most studies targeting MDSC in mice have used CD11b+, Gr-1+ as identifying markers (9), human MDSC are less well defined and have been variously characterized as being CD33+, CD11b+, Lin− and HLA-DR-cells (28, 30, 42).

As described herein, gene expression profiles of splenic MDSCs isolated from a transplanted murine pancreatic adenocarcinoma were compared with those from MDSCs from non-tumor bearing animals to identify a cell surface antigen, ICAM4, which recognizes an immunosuppressive MDSC population, both in mice and humans. The MDSC marker described herein can be used, e.g., as a target for therapy, to carry out pre-clinical studies on the role MDSCs in cancer development, progression and metastasis, and for monitoring efficacy of anti-cancer therapies.

Thus, in a first aspect the invention provides methods for treating cancer in a subject, or selecting a subject for treatment. The methods include detecting a level of ICAM4+ MDSC in a sample from the subject, e.g., a sample comprising blood, serum, urine or cancerous tissue; comparing the level of ICAM4+ MDSC in the sample to a reference level of ICAM4+ MDSC; and selecting a subject who has a level of ICAM4+ MDSC above a reference level for treatment with an immunotherapy targeting MDSCs, and optionally administering the immunotherapy targeting MDSCs to the subject; or selecting a subject who has a level of ICAM4+ MDSC at or below a reference level for treatment with a therapy that does not target MDSCs, e.g., an immunotherapy that does not target MDSCs or a non-immunotherapy anti-cancer therapy; and optionally administering the therapy that does not target MDSCs.

In another aspect, the invention provides methods for treating cancer in a subject. The methods include administering a therapeutically effective amount of an antibody that binds specifically to ICAM4 and reduces numbers or activity of ICAM4+ myeloid derived suppressor cells in the subject.

In some embodiments, the antibody is human, humanized, chimeric, or bifunctional. In some embodiments, the antibody is coupled to a cytotoxic peptide or protein, a radioisotope, or an anticancer drug. In some embodiments, the methods include administering an anti-cancer therapy, e.g., an immunotherapy, to the subject.

In some embodiments, the anti-cancer therapy is administered to the subject after the antibody that binds specifically to ICAM4, e.g., after at least one week of administration of the antibody that binds specifically to ICAM4.

In some embodiments, the anti-cancer therapy is selected from the group consisting of surgical resection with cold instruments or lasers, radiotherapy, phototherapy, biologic therapy (e.g., with tyrosine kinase inhibitors), radiofrequency ablation (RFA), radioembolisation (e.g., with 90Y spheres), chemotherapy, and immunotherapy (e.g., administering one or more of: a cancer vaccine, IL-2, cyclophosphamide, anti-interleukin-2R immunotoxins, or a checkpoint inhibitor or other immunotherapeutic antibody). In some embodiments, the anti-cancer therapy comprises administration of a checkpoint inhibitor, e.g., anti-CD137, anti-PD1, anti-PDL1, or anti-CTLA-4 antibody, and/or a cancer vaccine, e.g., vaccination with irradiated cancer cells, e.g., cells expressing ICOS, GM-CSF (Gvax) or Flt3-ligand (Fvax).

In some embodiments, the cancer is a solid cancer of epithelial origin. In some embodiments, the cancer is leukemia. In some embodiments, the cancer is characterized by the presence of ICAM4+ myeloid derived suppressor cells (MDSC) in the cancer tissue.

In some embodiments, the methods include obtaining a sample from the subject, e.g., a sample comprising blood, urine, CSF, or cancerous tissue; detecting the presence of ICAM4+ MDSC in the sample; and selecting a subject who has ICAM4+ MDSC present in the cancer tissue, e.g., a level of ICAM4+ MDSC above a reference level, and then administering a therapeutically effective amount of the antibody.

In a further aspect, the invention provides methods for monitoring the efficacy of a treatment for cancer in a subject over time. The methods include determining a first level of ICAM4+ MDSC in the subject, e.g., in a first sample from the subject, e.g., in a sample comprising blood urine, CSF, or cancerous tissue; determining a subsequent level of ICAM4+ MDSC in the subject, g., in a first sample from the subject, e.g., in a sample comprising blood or cancerous tissue; comparing the first and subsequent levels of ICAM4+ MDSC, and identifying a treatment as effective when the subsequent level of ICAM4+ MDSC is below the first level of ICAM4+ MDSC.

In some embodiments, the treatment specifically or non-specifically depletes ICAM4+ MDSC in the subject.

In some embodiments, the treatment is an anti-cancer therapy, e.g., an immunotherapy, as known in the art or described herein. In some embodiments, the treatment includes administration of a checkpoint inhibitor, e.g., anti-CD137, anti-PD1, anti-PDL1, or anti-CTLA-4 antibody.

In another aspect, the invention provides methods for identifying a candidate compound for the treatment of cancer. The methods include selecting a test compound that binds to ICAM4; contacting the test compound with a sample comprising myeloid derived suppressor cells (MDSC) that express ICAM4; detecting an effect of the test compound on the cells, e.g., on viability of the MDSC, lifespan of the MDSC, immune suppressive ability of the MDSC, or proliferation of the MDSC; and selecting as a candidate compound a test compound that reduces viability, life span, immune suppression or proliferation of the MDSC.

In some embodiments, selecting a test compound that binds to ICAM4 comprises providing a sample comprising ICAM4, e.g., cells expressing ICAM4 or purified ICAM4 protein; contacting the sample with a test compound; detecting binding of a test compound to ICAM4 in the sample; and selecting a test compound that binds to ICAM4.

In some embodiments, the methods include administering the selected candidate compound to an in vivo model of a disorder, e.g., an animal tumor model, e.g., a tumor xenograft model; detecting an effect on the model of the disorder, e.g., on one or more symptoms of the disorder (e.g., on numbers of MDSC in the tumor or spleen, tumor growth or metastasis); and selecting a candidate compound that reduces numbers of MDSC in the tumor or spleen, reduces tumor growth, or reduces metastasis as a candidate therapeutic agent and improves survival of the animal.

In some embodiments, the in vivo model of a disorder is an animal tumor model, e.g., a tumor xenograft model.

In yet another aspect, the invention provides methods for determining the effect of a treatment on MDSC levels in a subject over time. The methods include determining a first level of ICAM4+ MDSC in the subject, e.g., in a first sample from the subject, e.g., in a sample comprising blood urine, CSF, or cancerous tissue; determining a subsequent level of ICAM4+ MDSC in the subject, g., in a first sample from the subject, e.g., in a sample comprising blood or cancerous tissue; comparing the first and subsequent levels of ICAM4+ MDSC, and identifying a treatment as increasing MDSC when the subsequent level of ICAM4+ MDSC is above the first level of ICAM4+ MDSC, or identifying a treatment as decreasing MDSC when the subsequent level of ICAM4+ MDSC is below the first level of ICAM4+ MDSC.

In some embodiments, the treatment is a treatment for cancer.

In some embodiments, the treatment specifically or non-specifically depletes ICAM4+ MDSC in the subject.

In an additional aspect, the invention provides methods for determining a presence or level of MDSC in a subject. The methods include optionally obtaining a sample from the subject, e.g., a sample comprising blood urine, CSF, or cancerous tissue or tumor lysate; optionally enriching the sample in early myeloid progenitor cells (e.g., HLA-DR lo, CD33+ cells), e.g., using flow cytometry; contacting the sample with an antibody that binds to ICAM4; detecting binding of the antibody to the sample; and determining a level of MDSC in the sample based on binding of the antibody to the sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 10A-F. Comparison of frequency of ICAM4+ NOS2+ cells from BM-derived mouse MDSCs and PBMC-derived human MDSCs. Top: BM-MDSC generated from mouse BM cells with GM-CSF and IL-6 were stained for NOS2 expression alone (A) or co-expression with and Gr1 (B) and ICAM4 (C). Bottom: CD33$^+$ cells were isolated from PBMC treated for 4 d with GM-CSF and IL-6 and then stained with ICAM4 (D), NOS2 (E) or ICAM4-PE and NOS2-FITC (F). Similar results were obtained in three separate experiments.

FIG. 18. An exemplary sequence of human ICAM4 showing the extracellular domain and alignment scores showing identity with ICAM4 sequences from other species.

DETAILED DESCRIPTION

Figure 1A:
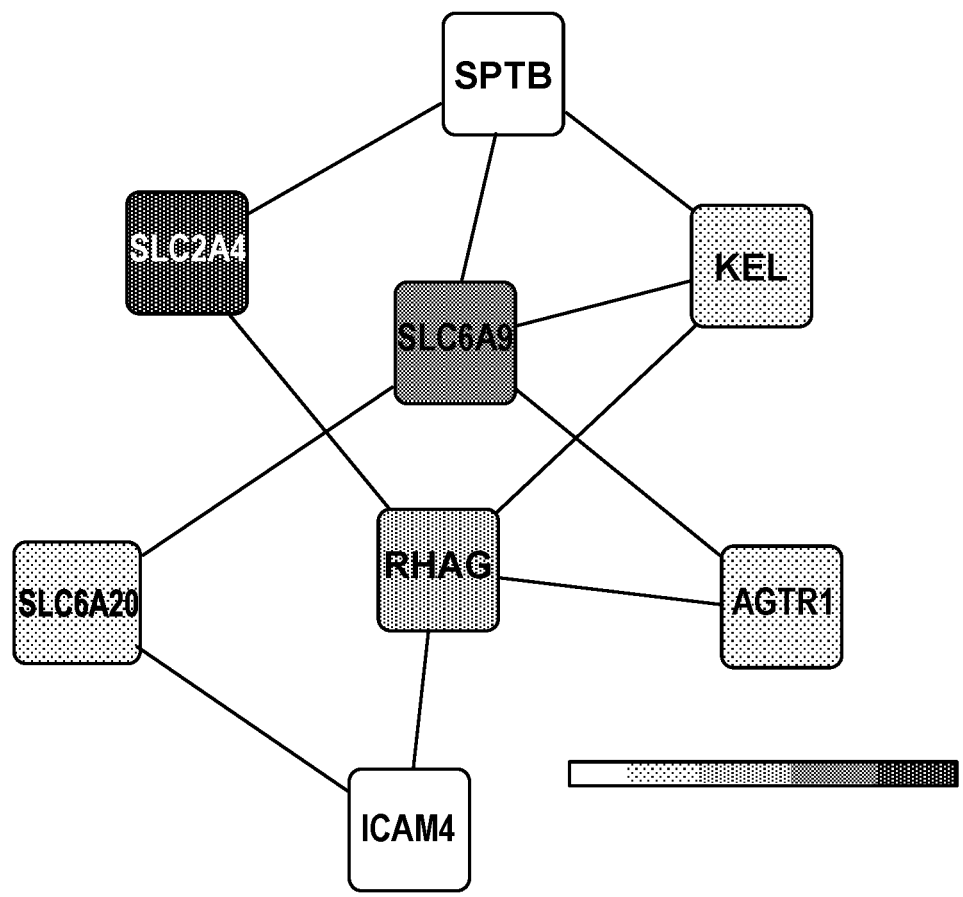
FIGS. 1A-C. Microarray analysis of gene expression in spleens of Pan02 tumor-bearing mice. (A) Interactive network of the top 8 genes that are i) differentially expressed ii) cell surface expressed and iii) minimally expressed in normal tissues. Nodes represent genes and edges represent biological interactions (e.g. co-expression, shared domain, pathways, biological process). Node color depicts the log ratio of wild type vs. mutant. (B) Fold differences in expression levels of ICAM4 RNA in MDSCs from two different tumors and in bone marrow derived MDSCs. (C) Fold differences in expression of a panel of genes that are differentially expressed in MDSCs from Pan02 or E0771 tumor-bearing mice. Representative data from three separate experiments.

Bone marrow suppressor cells were described in cancer more than 25 years ago (1), but received relatively minimal attention. However, pioneering work in a few laboratories has highlighted the importance of MDSCs as regulators of the immune system responsible for escape of tumors from immune surveillance (2-4). MDSCs are a heterogeneous population of myeloid cells made up of monocytes/macrophages, granulocytes and dendritic cells that are dramatically increased in the blood of cancer patients and in tumor-bearing mice (5). MDSCs are present at the tumor site (or in pre-neoplastic lesions) and in spleens before appearance of full-blown cancer in genetic models and in transplanted syngeneic mouse tumors (6, 7). MDSCs have received less attention than Tregs but interest in them is growing rapidly (as evidenced by papers published in recent times (8, 9). A key barrier to their study in humans has been a lack of specific cell-surface markers that can be used for identification and for specific targeting (10). In mice, MDSCs are commonly characterized as CD11b$^+$Gr-1$^+$. Furthermore, CD11b$^{hi}$, Gr-1$^{lo}$ cells are designated as monocytic and CD11b$^{lo}$, Gr-1$^{hi}$ cells are classified as granulocytic MDSC (11). Human MDSCs have an immature phenotype and were initially defined in lung, breast and head and neck cancers as HLA-DR$^-$Lin$^-$ cells (12). More recently, they have been described in renal cancer and melanoma as CD33$^+$ and HLA-DR$^-$Lin$^-$ cells (13, 14); in breast cancer as HLA-DR$^-$Lin$^-$CD33$^+$CD11b$^+$ cells (15); in advanced non-small cell lung cancer as CD14$^-$CD33$^+$CD11b$^+$CD15$^+$ (16) and as HLA-DR$^-$CD14$^+$ cells in melanoma, prostate, renal and hepatocellular carcinoma (17-19). There is thus a need to better define an MDSC population relevant in cancer patients bearing different tumors in order to compare treatment outcomes.

Moreover, MDSC employ a variety of mechanisms to target T cell function including production of arginase 1, nitric oxide (NO) via iNOS and reactive oxygen species (ROS) (20). Developing tumors secrete a wide variety of factors including vascular endothelial growth factor (VEGF), transforming growth factor-b (TGFb), granulocyte-macrophage colony-stimulating factor (GM-CSF), IL-10 and prostaglandin E2 that promote accumulation of MDSCs (21, 22). Recent studies (23, 24, 25) and the present inventors' unpublished data support the fact that tumor-derived lactate also affects innate immune function and results in arrested differentiation of APC from myeloid progenitors. MDSCs mediate immunosuppression by utilizing a number of mechanisms including two enzymes involved in arginine metabolism (ARG and NOS) as well as through TGFb, prostaglandin E2 (PGE2) production, and depletion of cysteine (5, 26). MDSCs also suppress immune effector function by modulating generation of regulatory T cells (27-29). This makes it even more critical to identify MDSC subsets that are relevant in immune function and therapeutic targeting and to define markers applicable across species.

It is worth noting that Treg-specific therapy has become a reality with the development of anti-GITR monoclonal antibody (TRX518) for cancer treatment (Schaer et al., Curr Opin Investig Drugs. 2010 December; 11(12):1378-86; Rosenzweig et al., J Clin Oncol 28, 2010 (suppl; abstr e13028)), now in Phase I trials (TRX518-001). Other treatments that deplete or reduce Treg activity are also known, e.g., cyclophosphamide (metronomic doses), arsenic trioxide, paclitaxel, sunitinib, oxaliplatin, PLX4720, anthracycline-based chemotherapy, and agents that selectively target the VEGF-VEGFR signaling axis, such as VEGF blocking antibodies (e.g., bevacizumab), or inhibitors of VEGFR tyrosine kinase activity (e.g., lenvatinib). Since MDSC appear early and can induce Tregs, an anti-MDSC therapy might be effective as a therapeutic agent in cancer. Inhibition of MDSC activity or depletion of MDSC number can overcome tumor growth in animal transplant models which can be achieved by a number of mechanisms including: MDSC depletion by use of anti-Gr-1 antibody; decreasing MDSC number with non-specific inhibitors such as 5-FU, docetaxel, and gemcitabine; altering conversion of MDSC to non-suppressive myeloid cells or by modulating function of MDSCs, e.g., using paclitaxel (30, 31). Use of anti-Gr-1 treatments to deplete MDSC in tumor-bearing mice led to decreased tumor burden and increased lifespan (32). In vitro depletion of CD11b$^+$, CD14$^-$ MDSCs isolated from renal cancer patients, restored function to anergic T cells (33). However, side effects such as neutrophil depletion and lack of Gr-1$^+$ on MDSCs in humans have precluded translation of these interesting findings to the clinic. The few studies that have been carried out to reduce MDSC with drugs, including use of sunitinib (34) or all-trans-retinoic acid (ATRA) followed by IL-2 therapy in renal cancer patients (13-14) have shown some efficacy. A major problem with some of these drugs is their lack of specificity: they impact cells in other immune compartments (e.g. ATRA promotes Tregs and cox-2 inhibitors can suppress DC maturation, both undesirable results in the context of cancer immunotherapy).

Murine MDSC are further defined as granulocytic CD11b$^+$Gr-1$^{hi}$ (Ly6G$^{hi}$Ly6C$^{lo/int}$) and monocytic CD11b$^+$Gr-1$^{lo}$ (Ly6G$^-$Ly6C$^{hi}$) MDSC. Greifenberg et al. (43) used LPS and IFNg induced-MDSCs to further subdivide into five different subtypes of MDSC and such finer characterizations will likely continue based on new markers that are identified (34, 44). A number of recent papers have reported novel markers for phenotypic characterization of (mostly murine) MDSC populations. Such classifiers include use of CD49d as a marker to distinguish immunosuppressive 'monocytic' CD11b$^+$CD49d$^+$ and 'granulocytic' CD11$^+$CD49d$^-$ MDSC in mice (45). A number of other markers for suppressive MDSC have also been reported in mice including CD80 (46), CD115 (47, 48), CD124/IL-4Ra (48), and the recently reported S100A9, which is reportedly present in both human and murine MDSC (49). S100A9 was identified as an MDSC marker associated with suppressive monocytic cells based on expression array analysis of CD14$^+$HLA-DR$^{-/lo}$ myeloid cells. Mouse MDSCs have been further characterized as CD11b$^+$Ly6G$^{lo}$ Ly6C$^{hi}$ monocytic-MDSCs (Mo-MDSC) that express nitric oxide synthase (NOS$_2$) and CD11b$^+$Ly6G$^{hi}$Ly6C$^{lo}$ granulocytic MDSCs (G-MDSC) that express arginase 1 (ARG1) (9). In mouse tumors, G-MDSCs have been more commonly characterized as the predominant population collecting in the spleens with a smaller number of mouse tumors where Mo-MDSCs are dominant (11). However, despite the more prevalent presence of G-MDSCs, Mo-MDSCs are considered to be more potent immunosuppressors (50).

Over two decades, human cancer studies have demonstrated the presence of myeloid cells with T cell suppressor function (9, 51-53). After several years of confusion in nomenclature, recent acceptable human MDSC markers include Lin$^-$, HLA-DR$^{lo}$, CD11b+, CD33+, CD14+ cells. Further subset definition has included use of CD14+ for Mo-MDSC and CD15+ for G-MDSC (9, 54). While MDSC plasticity has been attributed to this diversity in MDSC populations, both functional analysis and therapeutic targeting are impeded due to lack of overlap between murine and human MDSCs. All animal data pertaining to MDSC generation in disease and subsequent manipulation has been mostly based on following CD11b$^+$Gr-1$^+$ MDSCs and correlated with human MDSCs of multiple phenotypic characterizations. An aim of the present study was to find a common marker for MDSCs that not only identified murine and human MDSCs, but also identified the functional nature of these cells (viz. NO-based T cell suppressive function and NK cell cytotoxicity). As more and more clinical studies are considering the importance of inhibiting MDSCs to improve antitumor response whether in conjunction with standard chemotherapy or immunotherapies such as cancer vaccines or adoptive T cell therapy (30, 54), following clinical outcome with appropriate MDSC frequency monitoring will become critical.

Following gene expression profiling, ICAM4 expression was observed in MDSC from a number of different transplant tumor models as well as from a spontaneous pancreatic cancer model (24). The present data suggests that CD11b$^+$Gr-1$^+$ cells express ICAM4, and the ICAM4$^+$ cells obtained from different sources are also functionally similar in their immunosuppressive capacities. Thus, ICAM4+ cells isolated from spleens of tumor-bearing mice or from bone marrow cell derived MDSC were equally effective in suppressing CD4 proliferation, antigen-independent CD8 function as well as NK cell cytotoxicity. Since these ICAM4+ cells expressed NOS2 and ARG1 similar to commonly described MDSCs from mice, we characterize ICAM4+ cells as representing immunosuppressive MDSC. Moreover, ICAM4+ cells are also generated from PBMC by combined treatment with GM-CSF and IL-6 (as demonstrated by Lechner et al. [39]) and these cells (expressing CD33) express NOS2, TGFbeta, IL-6 and VEGF suggesting that cytokine-induced MDSCs are also represented by a population of ICAM4+ cells thereby lending support to the role of ICAM4 expression in this immunosuppressive population.

The present inventors have characterized the heterogeneous population of myeloid cells that can be observed in spleens and in tumor-infiltrating cells of multiple cancer types and shown that these cells can also be classified based on their cell-surface expression of ICAM4. Mouse BM cells can be made to differentiate into MDSCs that express conventional CD11b, Gr-1 markers; as shown herein, CD11b+Gr-1$^{hi}$ (Ly6G$^{hi}$Ly6C$^{lo/int}$) G-MDSC and CD11b+Gr-1$^{lo}$ (Ly6G−Ly6C$^{hi}$) Mo-MDSC can be further classified into ICAM4+ myeloid cells that are Mo-MDSCs. These ICAM4+ MDSCs express NOS2 and are T cell suppressive and inhibit NK cytolytic activity. Importantly, ICAM4+ myeloid cells are also generated in vitro when PBMC are treated with GM-CSF and IL-6 or when they are cultured in presence of CM from multiple cancer cell lines. These results support ICAM4+ myeloid cells as truly immunosuppressive Mo-MDSC that are present in murine cancers and in human PBMC-derived MDSC populations generated in vitro.

While depletion or inhibition of MDSCs has demonstrated improved immune profiles and proved to be beneficial in several recent attempts to develop effective cancer vaccines (54, 58), all these studies have used multiple drugs to decrease MDSC frequency, function or cause their differentiation. Selective targeted MDSC depletion, however, is still not available. While anti-Gr-1 antibodies have been used to deplete MDSC and have shown efficacious outcome in animal tumor models (eg. 59, 60), expression of Gr-1 in different cell types that include subpopulations of monocytes and dendritic cells (61) makes use of such antibody-based definition of MDSC of limited clinical value. Also, depletion of Gr-1+ cells with neutralizing antibody has also been shown to have no anti-tumor effect (62, 63) again, possibly because of the broad effect on other cell types. While human MDSC lack expression of Gr-1, those studies demonstrating improved outcome with Gr-1 antibody-mediated MDSC depletion in animals again highlight the need for targeted anti-MDSC therapy.

ICAM4

As described herein, ICAM4 is a new surface marker that recognizes MDSCs from tumor-bearing mice, from mouse bone marrow cells, and from human PBMC converted to immunosuppressive cells by GM-CSF and IL-6 or cancer cell conditioned media. These cells express genes associated with T cell suppression (Arg1, NOS2), and also express IL-6, VEGF, EP2 and EP4. ICAM4+ cells are present in the spleens and tumor infiltrates of mice in genetic models of murine breast and pancreatic ductal adenocarcinoma. ICAM4 is the first phenotypic marker that identifies a functional population of mouse MDSC and human PBMC-derived immunosuppressive cells and is relevant for clinical applications.

ICAM4 encodes the Landsteiner-Wiener (LW) blood group antigen(s) that belongs to the immunoglobulin (Ig) superfamily, and shares similarity with the intercellular adhesion molecule (ICAM) protein family. The ICAM4 protein contains 2 Ig-like C2-type domains and is a ligand for the leukocyte adhesion protein LFA-1 (integrin alpha-L/beta-2). ICAM4 is also a ligand for alpha-4/beta-1 and alpha-V integrins. While ICAM4 expression has been reported to be localized solely to erythrocytes (55), it has been reported to be upregulated in mesenchymal stem cells following IL1b treatment (56). ICAM4 has been reported to be located in a breast and prostate cancer susceptibility locus (19q13.2) (57).

FIG. 18 shows an exemplary human ICAM4 protein sequence. In humans, alternative splicing results in multiple transcript variants encoding distinct isoforms, the GenBank accession numbers for which are shown below in Table A. The Genomic sequence is at NC_000019.10.

TABLE A

| ICAM4 Sequences: GenBank Accession Numbers | | |
| --- | --- | --- |
| Isoform | Nucleic acid | Protein |
| isoform 1 precursor | NM_001544.4 | NP_001535.1 |
| isoform 2 precursor | N_022377.3 | NP_071772.1 |
| isoform 3 precursor | NM_001039132.2 | NP_001034221.1 |

ICAM4 is also described in U.S. Pat. No. 5,773,293.

Methods of Treatment

As demonstrated herein, MDSCs in human tumors can be identified by the expression of ICAM4, and optionally other markers such as Lin−, HLA-DR$^{lo}$, CD11b+, CD33+, CD14+ cells; in some embodiments, expression of ICAM4, plus one or more of CD33, CD14, and low expression of HLA-DR are used to identify MDSCs. Thus, the methods described herein include methods for the treatment of a cancer. Generally, the methods include administering a therapeutically effective amount of a molecule targeting ICAM4 as described herein, e.g., an anti-ICAM4 antibody, to a subject who is in need of, or who has been determined to be in need of, such treatment. In some embodiments, the methods include detecting the presence of ICAM4+ cells, i.e., ICAM4+ MDSCs (and optionally based on the presence of other markers such as Lin−, HLA-DRlo, CD11b+, CD33+, CD14+ cells; in some embodiments, expression of ICAM4, plus one or more of CD33, CD14, and low expression of HLA-DR are used to identify MDSCs), in a sample from the subject (e.g., a sample from the subject's tumor (e.g., from a primary tumor, lymph node, or metastatic site) or a sample of peripheral blood, CSF, urine, or bone marrow), and selecting a subject who has ICAM4+ MDSCs present in their tumor or blood for treatment with a therapy that depletes ICAM4+ MDSCs.

As used in this context, to "treat" means to ameliorate at least one clinical parameter of the cancer. In some embodiments, the parameter is tumor size, tumor growth rate, recurrence, or metastasis, and an improvement would be a reduction in tumor size or no change in a normally fast growing tumor; a reduction or cessation of tumor growth; a reduction in, delayed, or no recurrence, or a reduction in, delayed, or no metastasis. Administration of a therapeutically effective amount of a compound described herein for the treatment of a cancer would result in one or more of a reduction in tumor size or no change in a normally fast growing tumor; a reduction or cessation of tumor growth; or a reduction in, delayed, or no metastasis. In some embodiments, e.g., a treatment designed to prevent recurrence of cancer, the treatment would be given occur after a localized tumor has been removed, e.g., surgically, or treated with radiation therapy or with targeted therapy with or without other therapies such as standard chemotherapy. Without wishing to be bound by theory, such a treatment may work by keeping micrometastases dormant, e.g., by preventing them from being released from dormancy.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth. The methods described herein can be used to treat cancer, e.g., solid tumors of epithelial origin, e.g., as defined by the ICD-O (International Classification of Diseases—Oncology) code (revision 3), section (8010-8790), e.g., early stage cancer, is associated with the presence of a massive levels of satellite due to increase in transcription and processing of satellite repeats in epithelial cancer cells. Thus the methods can include the interference of satellite repeats in a sample comprising cells known or suspected of being tumor cells, e.g., cells from solid tumors of epithelial origin, e.g., pancreatic, lung, breast, prostate, renal, ovarian or colon/colorectal cancer cells.

Cancers of epithelial origin can include pancreatic cancer (e.g., pancreatic adenocarcinoma), lung cancer (e.g., non-small cell lung carcinoma or small cell lung carcinoma), prostate cancer, breast cancer, renal cancer, ovarian cancer, or colon cancer. Leukemia may include AML, CML or CLL and in some embodiments comprises cancerous MDSC. The methods can also be used to treat early preneoplastic cancers as a means to prevent the development of invasive cancer.

Subject Selection for Therapy

The identification of ICAM4+ cells as MDSCs allows the identification of certain patients as more likely to benefit from a therapy to deplete MDSC (also referred to herein as MDSC depletion therapy) than others. Thus, for example, the methods can include determining a level of ICAM4+ MDSCs in a sample from a subject, e.g., in a biopsy sample of cancerous tissue, or a peripheral blood sample, or a bone marrow sample, and comparing that level to a reference level. When a subject has levels of ICAM4+ MDSCs above the reference level, then that subject is more likely to benefit from a MDSC depletion therapy, and should be selected for (and optionally administered) a MDSC depletion therapy. In some embodiments, when a subject has levels of ICAM4+ MDSCs below the reference level, then that subject is more likely to benefit from a therapy, e.g., an immunotherapy, that is not an MDSC depletion therapy, and should be selected for (and optionally administered) a therapy that does not specifically delete MDSCs.

Suitable reference levels can be determined using routine statistical analysis of populations of subjects, and can represent, for example, a cutoff level for a percentile of a population of subjects stratified by response to MDSC depletion therapy and ICAM4+ MDSC levels at initiation of the immunotherapy, e.g., the lowest quintile, quartile, or tertile of subjects stratified by ICAM4+ MDSC level, or other threshold above which subjects are less likely to respond to immunotherapy. Other reference levels can also be used. MDSC depletion therapies can include those therapies targeted specifically to deplete ICAM4+ MDSC as described herein, as well as immunotherapy and other immune-depleting therapies.

Anti-Cancer Therapies

In some embodiments, the methods include administering an anti-cancer therapy to a subject, e.g., a subject who is treated using an ICAM4+ MDSC-depleting therapy as described herein (e.g., administration of a molecule targeting ICAM4 as described herein), or who is selected using a method described herein, i.e., identified as having a level of ICAM4+ cells above below a threshold. Cancer treatments include those known in the art, e.g., surgical resection with cold instruments or lasers, radiotherapy, phototherapy, biologic therapy (e.g., with tyrosine kinase inhibitors), radiofrequency ablation (RFA), radioembolisation (e.g., with 90Y spheres), chemotherapy, and immunotherapy. Non-limiting examples of chemotherapeutic agents include: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, axathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab (or an antigen-binding fragment thereof). Additional examples of anti-cancer treatments are known in the art; see, e.g. the guidelines for therapy from the American Society of Clinical Oncology (ASCO), European Society for Medical Oncology (ESMO), or National Comprehensive Cancer Network (NCCN).

In some embodiments, the methods include administering an immunotherapy to a subject, e.g., a subject who is treated using an MDSC-depleting therapy, or who is selected using a method described herein, i.e., identified as having a level of ICAM4+ cells below a threshold. Immunotherapies include those therapies that target tumor-induced immune suppression; see, e.g., Stewart and Smyth, Cancer Metastasis Rev. 2011 March; 30(1):125-40. Immunotherapies useful in the methods described herein include those therapies that specifically deplete ICAM4+ MDSC, e.g., that include the administration of a molecule targeting ICAM4 as described herein; therapies that non-specifically deplete ICAM4+ MDSC, e.g., that may not specifically target the ICAM4+ MDSC population but still result in depletion, altered localization, or reduced activity of ICAM4+ MDSC (referred to generically herein as "non-specific MDSC depletion immunotherapy"); and therapies that do not deplete MDSCs (referred to herein as "non-MDSC depleting immunotherapy"). In some embodiments, the methods include co-administering an immunotherapy, e.g., a non-specific MDSC depleting immunotherapy or a non-MDSC depleting immunotherapy, to the subject concurrently with or subsequent to the administration of a molecule targeting ICAM4. In some embodiments the methods include administering the molecule targeting ICAM4 for a time sufficient to substantially deplete the numbers of MDSCs present in the tumor or in the subject (e.g., in the bone marrow, spleen, or peripheral blood), e.g., to a level less than 50% of the pre-treatment level, e.g., to less than 40%, 30%, 20%, or 10% of the pre-treatment level, e.g., for at least one week, two weeks, three weeks, or a month or more, and then administering an immunotherapy; the molecule targeting ICAM4 can continue to be administered with the immunotherapy, or the two treatment modalities can be alternated.

Non-MDSC Depleting Immunotherapy

A number of immunotherapies that promote anti-cancer immunity but that don't specifically deplete MDSC (or that are not known to or designed to specifically deplete MDSC) are known in the art. In some embodiments, these therapies may primarily target other immunoregulatory cell types such as regulatory T cells (Tregs) or M2 polarized macrophages, e.g., by reducing number, altering function, or preventing tumor localization of the immunoregulatory cell types. For example, Treg-targeted therapy includes anti-GITR monoclonal antibody (TRX518), cyclophosphamide (e.g., metronomic doses), arsenic trioxide, paclitaxel, sunitinib, oxaliplatin, PLX4720, anthracycline-based chemotherapy, Daclizumab (anti-CD25); Immunotoxin eg. Ontak (denileukin diftitox); lymphoablation (e.g., chemical or radiation lymphoablation) and agents that selectively target the VEGF-VEGFR signaling axis, such as VEGF blocking antibodies (e.g., bevacizumab), or inhibitors of VEGFR tyrosine kinase activity (e.g., lenvatinib) or ATP hydrolysis (e.g., using ectonucleotidase inhibitors, e.g., ARL67156 (6-N,N-Diethyl-D-β,γ-dibromomethyleneATP trisodium salt), 8-(4-chlorophenylthio) cAMP (pCPT-cAMP) and a related cyclic nucleotide analog (8-[4-chlorophenylthio] cGMP; pCPT-cGMP) and those described in WO 2007135195, as well as mAbs against CD73 or CD39). Docetaxel also has effects on M2 macrophages. See, e.g., Zitvogel et al., Immunity 39:74-88 (2013). In another example, M2 macrophage targeted therapy includes clodronate-liposomes (Zeisberger, et al., Br J Cancer. 95:272-281 (2006)), DNA based vaccines (Luo, et al., J Clin Invest. 116(8): 2132-2141 (2006)), and M2 macrophage targeted pro-apoptotic peptides (Cieslewicz, et al., PNAS. 110(40): 15919-15924 (2013)). Immnotherapies that target Natural Killer T (NKT) cells can also be used, e.g., that support type I NKT over type II NKT (e.g., CD1d type I agonist ligands) or that inhibit the immune-suppressive functions of NKT, e.g., that antagonize TGF-beta or neutralize CD1d.

Some useful immunotherapies target the metabolic processes of immunity, and include adenosine receptor antagonists and small molecule inhibitors, e.g., istradefylline (KW-6002) and SCH-58261; indoleamine 2,3-dioxygenase (IDO) inhibitors, e.g., Small molecule inhibitors (e.g., 1-methyl-tryptophan (1MT), 1-methyl-d-tryptophan (D1MT), and Toho-1) or IDO-specific siRNAs, or natural products (e.g., Brassinin or exiguamine) (see, e.g., Munn, Front Biosci (Elite Ed). 2012 Jan. 1; 4:734-45) or monoclonal antibodies that neutralize the metabolites of IDO, e.g., mAbs against N-formyl-kynurenine.

In some embodiments, the immunotherapies may antagonize the action of cytokines and chemokines such as IL-10, TGF-beta, IL-6, CCL2 and others that are associated with immunosuppression in cancer. For example, TGF-beta neutralizing therapies include anti-TGF-beta antibodies (e.g. fresolimumab, Infliximab, Lerdelimumab, GC-1008), antisense oligodeoxynucleotides (e.g., Trabedersen), and small molecule inhibitors of TGF-beta (e.g. LY2157299), (Wojtowicz-Praga, Invest New Drugs. 21(1): 21-32 (2003)). Another example of therapies that antagonize immunosuppression cytokines can include anti-IL-6 antibodies (e.g. siltuximab) (Guo, et al., Cancer Treat Rev. 38(7):904-910 (2012). mAbs against IL-10 or its receptor can also be used, e.g., humanized versions of those described in Llorente et al., Arthritis & Rheumatism, 43(8): 1790-1800, 2000 (anti-IL-10 mAb), or Newton et al., Clin Exp Immunol. 2014 July; 177(1):261-8 (Anti-interleukin-10R1 monoclonal antibody).

mAbs against CCL2 or its receptors can also be used. In some embodiments, the cytokine immunotherapy is combined with a commonly used chemotherapeutic agent (e.g., gemcitabine, docetaxel, cisplatin, tamoxifen) as described in U.S. Pat. No. 8,476,246.

In some embodiments, immunotherapies can include agents that are believed to elicit "danger" signals, e.g., "PAMPs" (pathogen-associated molecular patterns) or "DAMPs" (damage-associated molecular patterns) that stimulate an immune response against the cancer. See, e.g., Pradeu and Cooper, Front Immunol. 2012, 3:287; Escamilla-Tilch et al., Immunol Cell Biol. 2013 November-December; 91(10):601-10. In some embodiments, immunotherapies can agonize toll-like receptors (TLRs) to stimulate an immune response. For example, TLR agonists include vaccine adjuvants (e.g., 3M-052) and small molecules (e.g., Imiquimod, muramyl dipeptide, CpG, and mifamurtide (muramyl tripeptide)) as well as polysaccharide krestin and endotoxin. See, Galluzi et al., Oncoimmunol. 1(5): 699-716 (2012), Lu et al., Clin Cancer Res. Jan. 1, 2011; 17(1): 67-76, U.S. Pat. Nos. 8,795,678 and 8,790,655. In some embodiments, immunotherapies can involve administration of cytokines that elicit an anti-cancer immune response, see Lee & Margolin, Cancers. 3: 3856-3893 (2011). For example, the cytokine IL-12 can be administered (Portielje, et al., Cancer Immunol Immunother. 52: 133-144 (2003)) or as gene therapy (Melero, et al., Trends Immunol. 22(3): 113-115 (2001)). In another example, interferons (IFNs), e.g., IFNgamma, can be administered as adjuvant therapy (Dunn et al., Nat Rev Immunol. 6: 836-848 (2006)).

In some embodiments, immunotherapies can antagonize cell surface receptors to enhance the anti-cancer immune response. For example, antagonistic monoclonal antibodies that boost the anti-cancer immune response can include antibodies that target CTLA-4 (ipilimumab, see Tarhini and Iqbal, Onco Targets Ther. 3:15-25 (2010) and U.S. Pat. No. 7,741,345 or Tremelimumab) or antibodies that target PD-1 (nivolumab, see Topalian, et al., NEJM. 366(26): 2443-2454 (2012) and WO2013/173223A1, pembrolizumab/MK-3475, Pidilizumab (CT-011)).

Some immunotherapies enhance T cell recruitment to the tumor site (such as Endothelin receptor-A/B (ETRA/B) blockade, e.g., with macitentan or the combination of the ETRA and ETRB antagonists BQ123 and BQ788, see Coffman et al., Cancer Biol Ther. 2013 February; 14(2):184-92), or enhance CD8 T-cell memory cell formation (e.g., using rapamycin and metformin, see, e.g., Pearce et al., Nature. 2009 Jul. 2; 460(7251):103-7; Mineharu et al., Mol Cancer Ther. 2014 Sep. 25. pii: molcanther.0400.2014; and Berezhnoy et al., Oncoimmunology. 2014 May 14; 3:e28811). Immunotherapies can also include administering one or more of: adoptive cell transfer (ACT) involving transfer of ex vivo expanded autologous or allogeneic tumor-reactive lymphocytes, e.g., dendritic cells or peptides with adjuvant; cancer vaccines such as DNA-based vaccines, cytokines (e.g., IL-2), cyclophosphamide, anti-interleukin-2R immunotoxins, Prostaglandin E2 Inhibitors (e.g., using SC-50) and/or checkpoint inhibitors including antibodies such as anti-CD137 (BMS-663513), anti-PD1 (e.g., Nivolumab, pembrolizumab/MK-3475, Pidilizumab (CT-011)), anti-PDL1 (e.g., BMS-936559, MPDL3280A), or anti-CTLA-4 (e.g., ipilumimab; see, e.g., Krüger et al., "Immune based therapies in cancer," Histol Histopathol. 2007 June; 22(6): 687-96; Eggermont et al., "Anti-CTLA-4 antibody adjuvant therapy in melanoma," Semin Oncol. 2010 October; 37(5): 455-9; Klinke D J 2nd, "A multiscale systems perspective on cancer, immunotherapy, and Interleukin-12," Mol Cancer.

2010 Sep. 15; 9:242; Alexandrescu et al., "Immunotherapy for melanoma: current status and perspectives," J Immunother. 2010 July-August; 33(6):570-90; Moschella et al., "Combination strategies for enhancing the efficacy of immunotherapy in cancer patients," Ann N Y Acad Sci. 2010 April; 1194:169-78; Ganesan and Bakhshi, "Systemic therapy for melanoma," Natl Med J India. 2010 January-February; 23(1):21-7; Golovina and Vonderheide, "Regulatory T cells: overcoming suppression of T-cell immunity," Cancer J. 2010 July-August; 16(4):342-7. In some embodiments, the methods include administering a composition comprising tumor-pulsed dendritic cells, e.g., as described in WO2009/114547 and references cited therein. See also Shiao et al., Genes & Dev. 2011. 25: 2559-2572.

MDSC Depletion Therapies

The methods described herein can also include administering a treatment that depletes, alters localization, or reduces activity of MDSCs. In some embodiments, the treatment will specifically target MDSCs, e.g., will include administration of a molecule targeting ICAM as described herein. In some embodiments, the treatment may not specifically target the ICAM4+ MDSC population but still result in depletion, altered localization, or reduced activity of ICAM4+ MDSC (referred to generically herein as "nonspecific MDSC depletion immunotherapy"). For example, a number of cancer treatments have been shown to decrease levels of MDSC, including Phosphodiesterase-5 (PDE-5) inhibitors such as sildenafil and tadalafil; Nitroaspirin (NO-aspirin); Synthetic triterpenoids such as Bardoxolone methyl (CDDO-Me), Cyclooxygenase 2 (COX2) inhibitors such as celecoxib and rofecoxib; arginase inhibitors such as N-hydroxy-L-Arginine (NOHA), nor-NOHA, nitroaspirin, or N(G)-Nitro-L-Arginine Methyl Ester (L-NAME); NF-κB inhibitors; inhibitors of Nitric oxide synthase, e.g., 1-NMMA, nitroaspirin; inhibitors of colony stimulating factors and their receptors, e.g., Monoclonal antibodies that block the CSF-1R (e.g. IMC-CS4) as well as small molecule inhibitors of CSF-1R (e.g. PLX3397) or cFMS kinase (e.g., GW 2580); histamine or H2 blockers such as cimetidine; IL-17; all-trans retinoic acid (ATRA); Vitamin D3 or Vitamin A; TLR9 ligand agonists such as CpG oligodeoxynucleotides (ODN); Nitro-Bisphosphonates (N-Bisphosphonates) such as zoledronic acid; inhibitors of STAT3 activation such as peptidomimetics, small molecule inhibitors (e.g., derivatives of curcurmin such as cucurbitacin B (CuB)), and platinum agents such as cisplatin; Sunitinib; Gemcitabine; 5-Fluorouracil (5-FU); paclitaxel; heat shock protein 90 (HSP90) inhibitors such as 17-DMAG (17-Dimethylamino-ethylamino-17-demethoxygeldanamycin); IL-13 linked to *Pseudomonas* exotoxin (IL-13-PE); and anti-Gr1+ antibodies. See, e.g., Wesolowski et al., J Immunother Cancer. 1:10 (2013) doi: 10.1186/2051-1426-1-10. eCollection 2013.

Monitoring Levels of ICAM4+ MDSC

Described herein are methods that can be used to monitor MDSC levels in a subject, e.g., to monitor the efficacy of a therapy (e.g., an immunotherapy, a treatment intended to deplete ICAM4+ MDSC as described herein, or another cancer therapy that may or may not be known or suspected to affect MDSC levels). In these embodiments, levels of ICAM4+ cells are detected (e.g., in a sample from a tumor such as a biopsy sample, or in circulation, e.g., in a blood sample) multiple times; changes in ICAM4+ levels indicate efficacy of therapy. For example, a decrease in ICAM4+ cells in a tumor indicates a reduction in immune suppression, e.g., that a therapy is effective in depleting MDSC; although this is particularly relevant to therapies such as an immunotherapy or a treatment intended to deplete ICAM4+ MDSC as described herein, a decrease in ICAM4+ MDSC also indicates that other types of therapy deplete MDSC by mechanisms that may include removal of factors that allow generation/migration of MDSCs. In addition, monitoring levels of ICAM4+ MDSC in a subject can be used to determine when to begin a therapy; for example, these monitoring methods can be used to determine when to administer an immunotherapy in a subject who is treated (e.g., using a method described herein) to deplete ICAM4+ cells before an immunotherapy is administered. For conditions in which depletion of MDSC is not desirable, e.g., in autoimmune diseases, levels of MDSC can be monitored as well; in these cases, an increase in MDSC is correlated with improved response to therapy.

Also described herein are methods that can be used to determine or monitor effects of cancer therapies on MDSC levels in a subject. Similar to the methods described above, levels of ICAM4+ cells are detected (e.g., in a sample from a tumor such as a biopsy sample, or in circulation, e.g., in a blood sample) multiple times; changes in ICAM4+ levels indicate that the therapy has an effect on MDSC levels (i.e., an increase in ICAM4+ levels indicates that the therapy increases MDSC levels, and a decrease in ICAM4+ levels indicates that the therapy decreases MDSC levels). In some embodiments, this information can be used to determine whether an additional therapy should be used, e.g., whether an additional therapy that targets MDSCs should be added to the initial therapy. Thus the methods can be used to select multiple therapeutic modalities; when an increase in ICAM4+ MDSCs is detected after administration of an initial therapy, an additional therapy can be selected (and optionally administered) that reduces MDSC levels, as described herein.

In addition, described herein are methods for predicting efficacy of therapy. A direct relationship between tumor burden and MDSC frequency has been demonstrated in several mouse models (Younos et al., Int. Immunopharmacol. 13:245-256 (2012); Donkor et al., Int. Immunopharmacol. 9:937-948 (2009)) and in human clinical studies of pancreatic cancer (Porembka et al., Cancer Immunol. Immunother. 61:1373-1385 (2012)); glioma (Kohanbash and Okada, Immunol Invest. 41(6-7):658-79 (2012)); gastric cancer (Wang et al., J. Immunol. 190, 794-804 (2013)); colorectal carcinoma (Zhang et al., PLoS One. 8(2):e57114 (2013)); breast cancer (Markowitz et al., Breast Cancer Res Treat. 140(1):13-21 (2013)); Gabitass et al., Cancer Immunol Immunother. 60(10):1419-30 (2011)); and solid tumors including breast cancer (Diaz-Montero et al., Cancer Immunol. Immunother. 58:49-59 (2009)). Thus, a reduction in MDSC levels (as determined herein by a decrease in ICAM4+ levels) is correlated with tumor shrinkage; higher levels of MDSC (as indicated by an increase in ICAM4+ levels, or by the presence of ICAM4+ levels over a threshold, e.g., a threshold that represents a level in a subject who is likely to respond) predicts a poorer or no response to therapy.

The monitoring methods can include determining a first or baseline level of ICAM4+ cells, and then determining one or more subsequent levels over time, e.g., after or during administration of one or more treatments, e.g., treatments intended to deplete ICAM4+ cells or immunotherapies. Methods known in the art can be used to detect and optionally quantify ICAM4+ cells in a sample, e.g., immunoassays (e.g., using detectable first or second antibodies, e.g., fluorescently labeled or enzymatically detectable antibodies) in solid or liquid samples; or cell sorting (e.g., fluorescence activated cell sorting in fluid samples) or by western blots or RNA-based expression analysis.

Although in most embodiments detection of ICAM4 protein will be used, detection of ICAM4 mRNA can also be used, e.g., using RNA in situ hybridization or other methods known in the art.

Secondary Markers of MDSC

In some circumstances, it may be desirable to use a secondary marker in addition to ICAM4 to identify MDSC. As one example, for cells expanded in vitro, ICAM4 alone can be used. In some embodiments, e.g., where mixed populations of hematopoietic cells are present in the sample, e,g., wherein ICAM4 may be expressed on certain other cell types in the sample, use of a secondary marker may be desirable; in these cases, detection of CD33 or CD14 may also be used, i.e., detection of ICAM4+CD33+, ICAM4+ CD14+, or ICAM4+CD33+CD14+ cells can be used in any of the methods described herein. Alternatively or in addition, a secondary marker can be used to exclude non-MDSCs; for example, a marker such as antigens of the ABO blood group or Glycophorin A positive RBC, or Diego antigen, can be used to exclude red blood cells. Other exclusionary secondary markers can include HLA-DR high and Lin positive populations.

Molecules Targeting ICAM 4

Also described herein are molecules that target ICAM4 and are useful in MDSC depletion therapy, prognosis, and diagnosis, and methods for identifying those molecules. The methods described herein can include administering a molecule that targets ICAM4, to thereby deplete ICAM4+ MDSC. Such molecules can include antibodies or other therapeutic compounds, e.g., small molecules, polypeptides, peptides, or inhibitory nucleic acids.

Anti-ICAM4 Antibodies

The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume* 1 (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010). Any of these methods can be used to make an anti-ICAM antibody. In addition, antibodies that bind to human ICAM4 are known in the art and commercially available, e.g., from Abbexa; Abcam; Abnova Corporation; Acris Antibodies GmbH; antibodies-online; Biorbyt; Bioss Inc.; Creative Biomart; LifeSpan BioSciences; Novus Biologicals; R&D Systems; Santa Cruz Biotechnology, Inc.; and St John's Laboratory. Anti-ICAM4 antibodies are also described in U.S. Pat. No. 5,773,293 A, e.g., secreted by hybridomas 127A, 127H, and 173E, designated A.T.C.C. Accession Numbers HB11905, HB11911, and HB11912, respectively. Table 1 shows a partial list of available commercially available anti-ICAM4 antibodies.

TABLE 1

| Antibody | Type | Antigen | Ordering Information | Notes |
|---|---|---|---|---|
| 127H | Mouse Monoclonal | Rat recombinant ECD | ATCC HB-11911 | ICOS Patent 5,773,293 |
| 173E | Mouse Monoclonal | Rat recombinant ECD | ATCC-HB-11912 | ICOS Patent 5,773,293 |
| 127A | Mouse Monoclonal | Rat Recombinant ECD | ATCC-HB-11905 | ICOS Patent 5,773,293 |
| B01P | Mouse Polyclonal | Full length human ICAM4, aa1-272 | Abnova-H00003386-B01P | Sold by multiple suppliers |
| Anti-ICAM4 polyclonal | Rabbit Polyclonal | Full length human ICAM4, aa1-272 | US Biologicals-128188 | |
| Anti-ICAM4 polyclonal | Goat Polyclonal | Peptide RHGSRVTYSESLER | Novus Biologicals-NBP2-26177 | |
| Human ICAM-4 Affinity Purified Polyclonal Ab | Sheep Polyclonal | | R&D-AF7179 | |
| ICAM-4 Antibody M-20 IgG | Goat polyclonal | epitope near the C-terminus of ICAM-4 of mouse origin | Santa Cruz sc-27686 | Blocking peptide available |

As used herein, the term "chimeric antibody" refers to an antibody that has been engineered to comprise at least one human constant region. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, U.S. Pat. Nos. 4,816,567; 4,978,775; 4,975,369; and 4,816,397.

"Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized antibodies are known in the art, and suitable techniques for generating humanized antibodies are also known. See for example, Hwang et al.,

*Methods* 36:35, 2005; Queen et al., *Proc. Natl. Acad. Sci. U.S.A.* 86:10029-10033, 1989; Jones et al., *Nature* 321:522-25, 1986; Riechmann et al., *Nature* 332:323-27, 1988; Verhoeyen et al., *Science* 239:1534-36, 1988; Orlandi et al., *Proc. Natl. Acad. Sci. U.S.A.* 86:3833-3837, 1989; U.S. Pat. Nos. 5,225,539; 5,530,101; 5,585,089; 5,693,761; 5,693,762; and 6,180,370; and WO 90/07861.

As used herein, the term "fully human antibodies" are antibodies or antigen binding fragments of antibodies that contain only human-derived amino acid sequences. For example, a fully human antibody may be produced from a human B-cell or a human hybridoma cell. In additional embodiments, the antibody may be produced from a transgenic animal that contains the locus for a human heavy chain immunoglobulin and a human light chain immunoglobulin, or contains a nucleic acid that encodes the heavy and light chains of a specific human antibody.

"Complementarity-determining region" or "CDR" as the terms are used herein refer to short polypeptide sequences within the variable region of both heavy and light chain polypeptides that are primarily responsible for mediating specific antigen recognition. CDRs have been described by Kabat, et al., *J. Biol. Chem.* 252, 6609-6616, 1977; Chothia et al., *J. Mol. Biol.* 196:901-917, 1987; and MacCallum et al., *J. Mol. Biol.* 262:732-745, 1996. There are three CDRs (termed CDR1, CDR2, and CDR3) within each VL and each VH.

"Fragment" or "antibody fragment" as the terms are used herein refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments can include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

"Framework region" as the term is used herein refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

In some embodiments, the anti-ICAM4 antibodies are bispecific antibodies, e.g., antibodies that have dual specificities in their binding arms and thus bind to two antigens at the same time. In some embodiments, the bispecific antibody binds to two antigens present on the same cell, e.g., both on MDSCs, e.g., to ICAM4 and CD33 or CD14. In some embodiments, the bispecific antibody binds antigens present on two different cells (i.e., cells of two types), such as ICAM4 on MDSC plus an antigen that may be present on a different type of cell, e.g., PD-1, PDL1, GITR, CTLA4, or CD16A. Thus, the methods can include the use of bispecific antibodies that bind to ICAM4 and CD33, CD14, PDL1, PD1, GITR, CTLA4, or CD16A. Methods for making bispecific antibodies are known in the art; see, e.g., Kufer et al., TRENDS in Biotechnology 22(5):238-244 (2004); Reusch et al., mAbs 6(3):727-738 (2014); Kudo et al., Tohuko J. Exp. Med. 188:275-288 (1999); Das and Suresh, Methods Mol Med. 109:329-46 (2005); Nolan and O'Kennedy, Biochim Biophys Acta. 1040(1):1-11 (1990); Compte et al., Oncoimmunology. 2014 May 23; 3:e28810. eCollection 2014; Jost and Plückthun, Curr Opin Struct Biol. 27C:102-112 (2014); and Byrne et al., Trends Biotechnol. 31(11):621-32 (2013).

The Anti-ICAM4 antibodies as described herein can be used to deliver a variety of anti-cancer therapeutic agents, e.g., a radioisotope; an anticancer drug such as a genotoxin; or any other cytotoxic moiety, e.g., molecules of plant, fungal, or bacterial origin, or biological proteins (e.g., protein toxins) or particles (e.g., a recombinant viral particles, e.g., via a viral coat protein), or mixtures thereof, to kill tumor cells or the MDSC themselves. The therapeutic agent can be an intracellularly active drug or other agent, such as short-range radiation emitters, including, for example, short-range, high-energy α-emitters, as described herein. In some embodiments, the anti-ICAM4 antibodies can be coupled to a molecule of plant or bacterial origin (or derivative thereof), e.g., a maytansinoid (e.g., maytansinol or the DM1 maytansinoid). DM1 is a sulfhydryl-containing derivative of maytansine that can be linked to the peptide, e.g., via a disulfide linker that releases DM1 when inside target cells. The disulfide linkers display greater stability in storage and in serum than other linkers. Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. Alternatively, the Anti-ICAM4 antibodies as described herein can be coupled to a taxane, a calicheamicin, a proteosome inhibitor, or a topoisomerase inhibitor. [(1R)-3-methyl-1-[[(2S)-1-oxo-3-phenyl-2-[(3-mercaptoacetyl) amino]propyl]amino]butyl] Boronic acid is a suitable proteosome inhibitor. N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In some embodiments, the Anti-ICAM4 antibodies is conjugated to maytansinoids, e.g., maytansinol (see U.S. Pat. No. 5,208,020), CC-1065 (see U.S. Pat. Nos. 5,475,092, 5,585,499, 5,846,545). Procedures for preparing enzymatically active polypeptides of the immunotoxins are described in WO84/03508 and WO85/03508, which are hereby incorporated by reference. Examples of cytotoxic moieties that can be conjugated to the antibodies include adriamycin, chlorambucil, daunomycin, methotrexate, neocarzinostatin, and platinum.

To kill or ablate cancer cells or MDSC, anti-ICAM4 antibodies can be conjugated with a prodrug that is activated only when in close proximity with a prodrug activator. The prodrug activator is conjugated with a second anti-ICAM4 antibody, preferably one that binds to a non-competing site on the same receptor (e.g., ICAM4) or cell (e.g., CD33). Whether two Anti-ICAM4 antibodies bind to competing or non-competing binding sites can be determined by conventional competitive binding assays. Drug-prodrug pairs suitable for use are known in the art, see, e.g., in Blakely et al., Cancer Research 56:3287-3292 (1996).

A drug attached to an anti-ICAM4 antibodies as described herein can also include agents that are derived from, or that beneficially modulate host biological processes, such as interferons, tumor growth factors, tumor necrosis factors, growth factors such as GM-CSF and G-CSF and interleukins, for example, interleukin-2, interleukin-6, interleukin-7 and interleukin-12, and the like. A drug attached to an anti-ICAM4 antibody as described herein may comprise an agent which damages DNA and/or prevent cells from multiplying, such as genotoxins. A genotoxin includes but is not limited to alkylating agents, antimetabolites, DNA cutters, DNA binders, topoisomerase poisons and spindle poisons. Examples of alkylating agents are lomustine, carmustine, streptozocin, mechlorethamine, melphalan, uracil nitrogen mustard, chlorambucil, cyclophosphamide, iphosphamide, cisplatin, carboplatin, mitomycin, thiotepa, dacarbazin, procarbazine, hexamethyl melamine, triethylene melamine, busulfan, pipobroman, mitotane and other platine derivatives.

Alternatively, the anti-ICAM4 antibodies can be coupled to high energy radiation emitters, for example, a radioisotope, such as $^{131}$I, a γ-emitter, which, when localized at the tumor site, results in a killing of several cell diameters. See, e.g., Order, "Analysis, Results, and Future Prospective of the Therapeutic Use of Radiolabeled Antibody in Cancer Therapy", in *Monoclonal Antibodies for Cancer Detection and Therapy*, R. W. Baldwin et al. (eds.), pp 303-316 (Academic Press 1985). Other suitable radioisotopes include α-emitters, such as $^{212}$Bi, $^{213}$Bi, and $^{211}$At, and β-emitters, such as $^{186}$Re and $^{90}$Y. Lu$^{117}$ may also be used as both an imaging and cytotoxic agent.

Radioimmunotherapy (RIT) using anti-ICAM4 antibodies labeled with $^{131}$I, $^{90}$Y, and $^{177}$Lu can also be used. There are significant differences in the physical characteristics of these three nuclides and as a result, the choice of radionuclide can be important to deliver maximum radiation dose to the tumor. The higher beta energy particles of $^{90}$Y may be good for bulky tumors, but it may not be necessary for small tumors and especially bone metastases, (e.g., those common to prostate cancer). The relatively low energy beta particles of $^{131}$I are ideal, but in vivo dehalogenation of radioiodinated molecules is a major disadvantage for internalizing Anti-ICAM4 antibodies. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers (see, e.g., Mulligan et al., Clin Cancer Res. 1: 1447-1454 (1995); Meredith et al., J Nucl Med 37:1491-1496 (1996); Alvarez et al., Gynecologic Oncology 65: 94-101 (1997)).

The Anti-ICAM4 antibodies can also be conjugated or fused to viral surface proteins present on viral particles. For example, an anti-ICAM4 antibodies could be fused (e.g., to form a fusion protein) to a viral surface protein. Alternatively, an anti-ICAM4 antibodies could be chemically conjugated (e.g., via a chemical linker) to a viral surface protein. Preferably, the virus is one that fuses with endocytic membranes, e.g., an influenza virus, such that the virus is internalized along with the anti-ICAM4 antibodies and thereby enters and kills the MDSC. The virus can be genetically engineered as a cellular toxin. For example, the virus could express or induce the expression of genes that are toxic to cells, e.g., cell death promoting genes. Preferably, such viruses would be incapable of viral replication.

Additional examples of cytotoxic peptides or proteins include Idarubicin; CRM9 (e.g., FN18-CRM9, Knechtle et al., Transplantation 1997; 63:1-6); or pokeweed antiviral protein. In some embodiments, the cytotoxic protein is a bacterial toxin, e.g., diphtheria toxin (DT) or portions or variants thereof, e.g., Met1-Thr387, e.g., as described in Aullo et al., EMBO J. 11(2):575-83 (1992); Abi-Habib et al., Blood. 104(7):2143-2148 (2004); Perentesis et al., Proc. Nati. Acad. Sci. USA 85:8386-8390 (1988); Zettlemeissl et al., Gene. 41(1):103-111 (1986); US 2009/0010966; US20090041797; U.S. Pat. Nos. 5,843,711; 7,585,942; 7,696,338; or US20080166375; monomethyl auristatin E; or *Pseudomonas* exotoxin (PE), or portions or variants thereof, e.g., as described in U.S. Pat. Nos. 4,545,985; 4,892,827; 5,458,878; 7,314,632; Song et al., Protein Expression and Purification 44(1):52-57 (2005); Theuer et al., J. Biol. Chem. 267(24):16872-16877 (1992); Heimbrook et al., Proc Natl Acad Sci USA. 87(12):4697-4701 (1990); Debinski et al., Mol Cell Biol. 11(3):1751-1753 (1991); Chaudhary et al., Proc. Nadl. Acad. Sci. USA 87:308-312 (1990). In some embodiments, the cytotoxic protein is a plant toxin, e.g., a plant holotoxin (e.g., class II ribosome-inactivating proteins such as ricin (e.g., deglycosylated ricin A chain (dgA)), abrin, mistletoe lectin, or modeccin) or hemitoxin (class I ribosome-inactivating proteins, e.g., PAP, saporin, bryodin 1, bouganin, or gelonin), or fragments or variants thereof that retain cytotoxic activity. See, e.g., Neville et al., J Contr Rel 1993; 24:133-141; Vallera, Blood 1994; 83:309-317; Vitetta et al., Immunology Today 1993; 14:252-259; Kreitman et al., AAPS Journal. 2006; 8(3):E532-E551). Suitable sequences are known in the art.

The anti-cancer agent can be coupled to the antibody using any known means to create a stable link, e.g., a chemical or peptide linker; cleavable (disulfides, hydrazones or peptides) or noncleavable (thioethers) linkers can be used. Peptide linkers, e.g., flexible or rigid peptide linkers, are used in some embodiments. In some embodiments, a cathepsin cleavable linker (valine-citrulline) and one or more spacers, e.g., para-aminobenzylcarbamate spacers are included. Crosslinking reagents such as succinimidyl trans-4-(maleimidylmethyl)cyclohexane-1-carboxylate (SMCC) can also be used.

In the above examples, wherein the anti-ICAM4 antibodies are linked to a therapeutic agent that acts intracellularly (i.e., antibody-drug conjugates), it is desirable to use an antibody that undergoes internalization after binding to an MDSC. In some embodiments, antibodies that are not internalized, but that allow complement to bind and elicit antibody-dependent cytotoxicity, can be used to actively deplete MDSC. In some embodiments, antibodies that bind tightly and are not internalized are preferred, e.g., for detection and monitoring of ICAM4+ MDSC levels, or for plasmapharesis. In some embodiments, antibodies that bind to ICAM4 and prevent binding to its receptor, e.g., by a physical mechanism such as steric inhibition, can also be used.

The anti-ICAM4 antibodies can also be used to physically deplete ICAM4+ MDSC from a subject, e.g., using immunoadsorption/plasmapharesis (or therapeutic plasma exchange) with an ICAM4-binding exchange membrane or resin. See, e.g., Reeves and Winters, Br J Haematol. 2014 February; 164(3):342-51.

In some embodiments, in place of a traditional immunoglobulin or monoclonal antibody, a phagebody is used, e.g., as described in Petrenko and Smith, Protein Eng. 13(8):589-92 (2000).

Small Molecules

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da). Included herein are methods for screening test compounds, e.g., small molecule test compounds, to identify agents that target ICAM4 and deplete numbers and/or activity of ICAM4+ MDSCs and are useful in the treatment of cancer as described herein. As used herein, an activity of ICAM4+ MDSC can include expression of NOS2, suppression of T cell function, eg. IFNg production, and inhibition of NK cytolytic activity. Assays for each of these activities are known in the art. For example, to determine whether a compound, e.g., an antibody or small molecule, is neutralizing, the compound is added to ICAM4+ MDSC, T cells are added, and the T cells are stimulated, e.g., using anti-CD3 and anti-CD28 antibodies, and T cell proliferation or secretion of IFNgamma is detected, as shown herein. An increase in T cell proliferation and IFNg secretion indicates that the compound neutralized the MDSC; see, e.g., Example 4. Alternatively or in addition, an NK cell lysis assay can be used, and the ability of a compound (e.g., small molecule or antibody) to inhibit ICAM4+ MDSC-mediated suppression of NK cell lysis activity is evaluated, e.g., the ability to lyse K562 cells. An increase in NK-cell lysis in the presence of the compound indicates that the compound inhibits MDSC activity. See, e.g., Example 4.

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries to be screened can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cancer cell or living cancer tissue or organ, e.g., a tumor explant, and one or more effects of the test compound is evaluated. In a cultured or primary cell for example, the ability of the test compound to reduce ICAM4 expression, and/or ICAM4+ MDSC numbers or activity, can be evaluated.

In some embodiments, the test sample is, or is derived from (e.g., a sample taken from) an in vivo model of a disorder as described herein. For example, an animal model, e.g., a xenograft model in a rodent such as a rat or mouse, can be used, and the ability of the test compound to inhibit ICAM4 expression, and/or ICAM4+ MDSC numbers or activity, can be evaluated.

Methods for evaluating these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on ICAM4 expression.

A test compound that has been screened by a method described herein and determined to reduce ICAM4 expression, and/or ICAM4+ MDSC numbers or activity, can be considered a candidate compound. A candidate compound that has been screened, e.g., in an in vivo model of a disorder, e.g., an animal tumor model, e.g., a tumor xenograft model, and determined to have a desirable effect on the disorder, e.g., on one or more symptoms of the disorder (e.g., on tumor growth or metastasis), can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that reduce ICAM4 expression, and/or ICAM4+ MDSC numbers or activity) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating cancers as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a cancer. The animal can be monitored for a change in the disorder, e.g., for an improvement in a parameter of the disorder, e.g., a parameter related to clinical outcome. In some embodiments, the parameter is tumor size, tumor growth rate, recurrence, or metastasis, and an improvement would be a reduction in tumor size or no change in a normally fast growing tumor; a reduction or cessation of tumor growth; a reduction in, delayed, or no recurrence; or a reduction in, delayed, or no metastasis. In some embodiments, the parameter is lifespan, or survival time after diagnosis, and an improvement would be an increase in lifespan or survival time after diagnosis.

The methods described above for small molecules can also be used to identify peptides, polypeptides, or nucleic acids that target ICAM4 and inhibit activity or reduce numbers of ICAM4+ MDSCs.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics that hybridize to at least a portion of the target nucleic acid, i.e., ICAM4, and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241; 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a target RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to an RNA are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60

(2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

siRNA/shRNA

In some embodiments, the nucleic acid sequence that is complementary to an RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $\text{min}^{-1}$ in the presence of saturating (10 rnM) concentrations of $\text{Mg}^{2+}$ cofactor. An artificial "RNA ligase" ribozyme has been shown to catalyze the corresponding self-modification reaction with a rate of about 100 $\text{min}^{-1}$. In addition, it is known that certain modified hammerhead ribozymes that have substrate binding arms made of DNA catalyze RNA cleavage with multiple turn-over rates that approach 100 $\text{min}^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising molecules that target ICAM4 as active reagents, e.g., an anti-ICAM4 antibody, small molecule, or inhibitory nucleic acid targeting ICAM4 as described herein.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy,* 21st ed., 2005.

The active compounds can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of these compositions can include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the compounds can be co-administered with drugs for treating or reducing risk of a disorder described herein, e.g., other immunotherapies or anti-cancer treatments.

Aptamers

Aptamers are short oligonucleotide sequences that can tightly and discreetly bind to specific target molecules, e.g., proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al (1992) Nature 355: 564 566 and U.S. Pat. No. 5,582,981 (1996) Toole et al).

Aptameric species can be generated by incubating randomly-generated oligonucleotide sequences with a target molecule, selecting for oligonucleotide sequences competent for binding the target, amplifying to generate a new pool, and repeating the process until the desirable phenotype is observed and/or sequence diversity is significantly minimized (see Tuerk and Gold, Science 249:505-510 (1990); Ellington and Szostak, Nature 346:818-822 (1990)). Specificity can be increased by introduction of a negative selection step in which oligonucleotide sequences are incubated with non-target molecules and bound oligonucleotides are removed from the pool of remaining potential aptamers (Yan and Levy, RNA Bio. 6(3): 316-320 (2009)). The final remaining sequences can be cloned and sequenced to characterize the aptamers after the iterative selection process. Methods for selection and preparation of such RNA aptamers are known in the art (see, e.g., Feigon et al., Chem. Biol. 3: 611 (1996); Kelly et al., J. Mol. Biol. 256:417 (1996); Famulok, Curr. Opin. Struct. Biol. 9:324 (1999); Herman and Patel, J. Science 287:820-825 (2000)); Santosh and Yadava, Biomed Res Int. 2014:540451 (2014); Szeitner et al., J Pharm Biomed Anal. pii: S0731-7085(14)00209-X (2014); Kong and Byun, Biomol Ther (Seoul). 21(6):423-34 (2013).

EXAMPLES

The invention is further described in the following examples, which do not limit the scope of the invention described in the claims.

Materials and Methods

The following materials and methods were used in the Examples set forth below.

Mice and In Vivo Studies

C57Bl/6 mice were purchased from Charles River (Wilmington, Mass.) and housed in the animal facility at BIDMC. Six to 8-week-old female C57/BL6 mice weighing approximately 17 gm were maintained for 1 week before use. Mice were housed 5 per cage in a limited access area at a mean room temperature of 20±1° C. and a humidity of 50%±10% with free access to food and water. All experiments were approved by the institutional animal review board. Mice were inoculated s.c with Pan02, E0771, RM-9 or B16 cells ($1\times10^6$ cells per mice). Tumor volume was determined as described before.

Cell Isolation and Analysis

Spleens collected from tumor bearing and non-tumor bearing mice were used to isolate T cells, NK cells and MDSCs. For isolation of tumor infiltrating lymphocytes, tumor specimens were washed with PBS, minced with scissors and digested 30 minutes at 37° C. with 0.1% collagenase type IV, 0.2 mg/ml hyaluronidase type V and 0.01% DNase I (from Sigma-Aldrich). The digestion was stopped by the addition of an excess of RPMI 1640 media containing heat inactivated 10% FCS. Cell suspensions was then sequentially passed through 100 mm, 70 mm and 40 mm cell strainers (BD Falcon) washing 3 times with RPMI 1640 media containing 10% FCS. Lymphocytes were purified by density gradient (Ficoll-Hypaque PLUS, GE Healthcare), and stained for analytical flow cytometry, preparative FACS sorting or isolation with magnetic beads. For cytotoxicity assays, tumor infiltrating NK cells were isolated with magnetic beads by depletion of $CD3^+$ cells and subsequent isolation of $NK1.1^+$ cells. The purity of populations determined by flow cytometric analysis was routinely >93%.

Isolation of Myeloid Derived Suppressor Cells

To purify $CD11b^+Gr-1^+$ cells, erythrocyte-depleted splenocytes were first depleted of CD11b Gr-1 cells via magnetic selection using anti-CD19 and anti-CD11c microbeads and LD columns following the manufacturer's instructions (Miltenyi Biotec, Auburn, Calif.). The purity of the total MDSC population or the MDSC sub fractions was typically higher than 90%.

Patients, Analysis of MDSCs

Blood samples were collected from prostate cancer patients according to prior-approved IRB protocol. PBMCs were isolated from freshly drawn blood by Ficoll-Paque Plus (GE Healthcare, Uppsala, Sweden) density gradient centrifugation and cryopreserved. PBMCs were thawed by incubation at 37° C. (1-2 min) followed by re-suspension in RPMI 1640 and centrifugation. Cell pellets were assessed for viability with trypan blue and evaluated immediately using multicolor flow cytometry following staining with appropriate antibodies as described in the following section "Monoclonal Abs and flow cytometry".

Monoclonal Abs and Flow Cytometry

Cell surface staining with fluorescent dye-conjugated antibodies and intracytoplasmic staining experiments were carried out following standard procedures (35). The following antibodies were used: PE, FITC, APC-conjugated anti-Gr1 and anti-CD11b, PE-conjugated CD4, CD8; PE, APC, PE-Cy5.5 conjugated Ly6C and Ly6G; and FITC-conjugated NOS2. All were purchased from BD Biosciences (San Diego, Calif.), or from BioLegend (San Diego, Calif.). PE, FITC conjugation of ICAM4 was carried out with mouse ICAM4 antibody (clone M-20) from Santa Cruz (Santa Cruz, Calif.), a polyclonal ICAM4 antibody (11918-1-AP) from Proteintech (Chicago, Ill.), or mouse polyclonal antibody (B01P) from Abnova (Walnut, Calif.). FITC and PE-linking of ICAM4 antibodies were carried out with Lightning-Link antibody labeling kits (Novus, Littleton, Colo.). Human CD33+ cells were isolated using CD33 MicroBeads (Miltenyi, Auburn, Calif.) as described by the manufacturer. Anti-human CD4, CD8, HLA-DR, CD14, CD33 antibodies were purchased from BD Biosciences and eBioscience (San Diego, Calif.). Cell sorting was done with a FACSAria II sorter (Becton Dickinson, San Jose, Calif.) and analytical measurements were done with a BD FACSCanto flow cytometer. Data analysis was performed using FloJo software (Tree Star, Ashland, Oreg.).

MDSC Suppression Assay

MDSC suppression of T cells was carried out against splenic T cells isolated from C57Bl/6 mice without tumors. T cells were isolated using a T cell-enrichment column (R&D Systems). Isolated T cells ($2 \times 10^4$), at different ratios, were activated with α-CD3/α-CD28 cultured with irradiated MDSC ($5 \times 10^4$). CD4 T cell proliferation was analyzed using Alamar blue or with CFSE staining. Human T cell proliferation assays were performed as described before (24).

Microarray Analysis

Splenocytes were isolated from mice with subcutaneous Pan02 tumors after three weeks. MDSC isolated from splenocytes of control and tumor-bearing animals (as described in previous section) were used for RNA isolation (NucleoSpin RNA II, Machery-Nagel, Duren, Germany) followed by linear T7 amplification and hybridization to Agilent Whole Mouse Genome Oligo Microarray. Scanned array images were analyzed using a customized R language script developed for quality control analysis and normalization. The raw probe level data was normalized using Loess and quantile normalization routines of the linear model microarray analysis software package (limma) from bioconductor to adjust for dye bias and variation among arrays. To identify differentially expressed genes, a linear model was implemented using limma (36). Limma estimates the differences between tumor and control MDSC by fitting a linear model and using an empirical Bayes method to moderate standard errors of the estimated log-fold changes for expression values from each probe set. The differentially expressed probes were identified on the basis of absolute fold change and Benjamini and Hochberg corrected P value (37).

Interactive Network Analysis

To decipher the interaction among genes, we performed interactive network analysis. The interactive network was generated using known Protein-Protein, Protein-DNA, co-expression and Protein-RNA interactions. The interaction information was obtained using literature search and publically available databases.

Cytotoxicity Assays

NK cells were isolated using an NK Cell Isolation Kit (Miltenyi Biotec, Auburn, Calif.). NK cytotoxic activity was measured as described earlier (24). In some experiments, NK cytotoxicity was measured using aCellaTox non-radioactive assay (Cell Technology, Mountain View, Calif.) and targeted cell lysis was calculated according to the manufacturer's instructions.

In Vitro Cytokine-Induced MDSC

Human PBMC were isolated from blood obtained from healthy volunteers by Ficoll density gradient centrifugation (Sigma-Aldrich, St. Louis, Mo.). PBMC were cultured ($5 \times 10^5$ cells/ml) in RPMI media with 10% FCS, 2 mM L-glutamine, 100 U/penicillin and 100 ug/ml streptomycin supplemented with GM-CSF (10 ng/ml; R&D Systems, Minneapolis, Minn.) and IL-6 (R&D Systems).

Confocal Microscopy

Tumors from mice were harvested at appropriate time, fixed and prepared for cryostat sections. Tissue sections (5 um) were incubated with rat anti-mouse mAbs specific to Gr1, ICAM4. Sections were labeled with Alexa Fluor 555 anti-rat or Alexa Fluor 488 anti-rabbit IgG. DAPI (Sigma, St. Louis, Mo.) was used for nuclear staining. Confocal microscopy was performed on a Zeiss LSM510 Upright Confocal System.

Statistical Analyses

Statistical analyses for differences between groups were performed by using the unpaired Student's t test. Values were considered statistically significant for $p<0.05$.

Example 1. ICAM4 Gene Expression is Associated with Mouse MDSC

A small population of CD11b+Gr1+ cells can be isolated from spleens of healthy mice and this population expands dramatically in tumor-bearing animals. We have used these cells to perform transcriptional profiling and determine gene expression in MDSCs isolated from spleens of transplanted pancreatic tumor-bearing mice. Microarray analysis of gene expression in CD11b$^+$Gr-1$^+$ cells isolated from spleens of normal and pancreatic cancer (Pan02) bearing mice revealed significant differential expression of 56 genes with absolute fold change (>7 folds) and P value<.0001. Since one of our major goals was to identify potential MDSC markers that could be used for isolation/therapeutic targeting of MDSC, we focused on genes that: (1) were likely to encode cell surface antigens (based upon presence of leader sequence and transmembrane region(s), (2) had likely mouse human orthologues, (3) were tissue restricted in expression, (4) were also differentially expressed in MDSCs in 2 other tumor models, (5) were expressed in in vitro developed MDSC cultures and (6) marked an immunosuppressive population in an in vitro assay. To select genes with potential cell surface expression, we performed subcellular localization analysis using the UniProt database (38) and identified 20 genes with transmembrane domains indicating plasma membrane associated expression. To eliminate the genes highly expressed in various tissues and cell types, we performed restricted expression analysis using gene expression data from the BioGPS Gene Atlas Portal. This analysis identified 8 unique genes with mean absolute value of expression <15 in various cells and tissues. The interactive network of these 8 genes is shown in FIG. 1A. Representative barplots demonstrating tissue-restricted expression of genes in various cell types and tissues is shown FIG. 12. The mRNA expression of these genes was validated using RTPCR (some of which is shown as FIG. 1B, C). From this analysis emerged the identification of ICAM4 as a novel candidate MDSC marker.

Figure 1B:
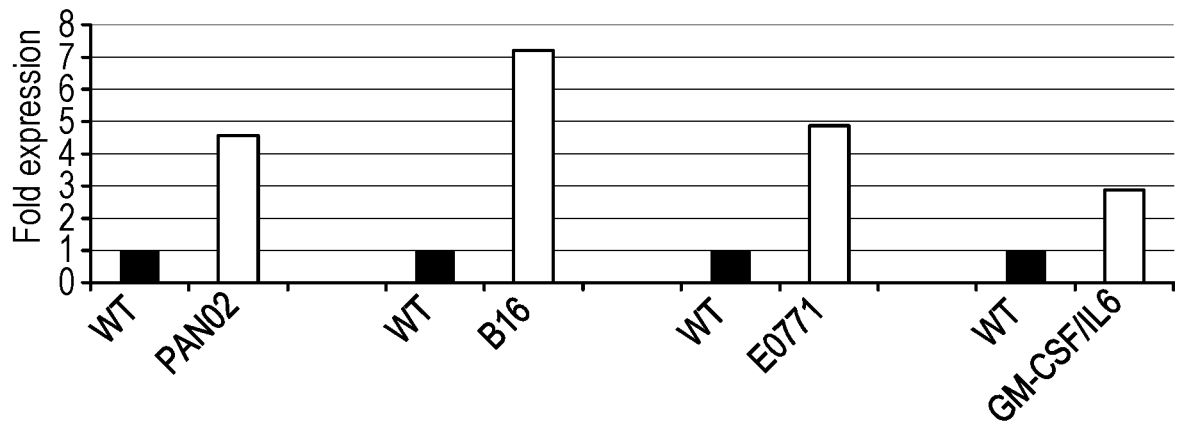
Figure 1C:
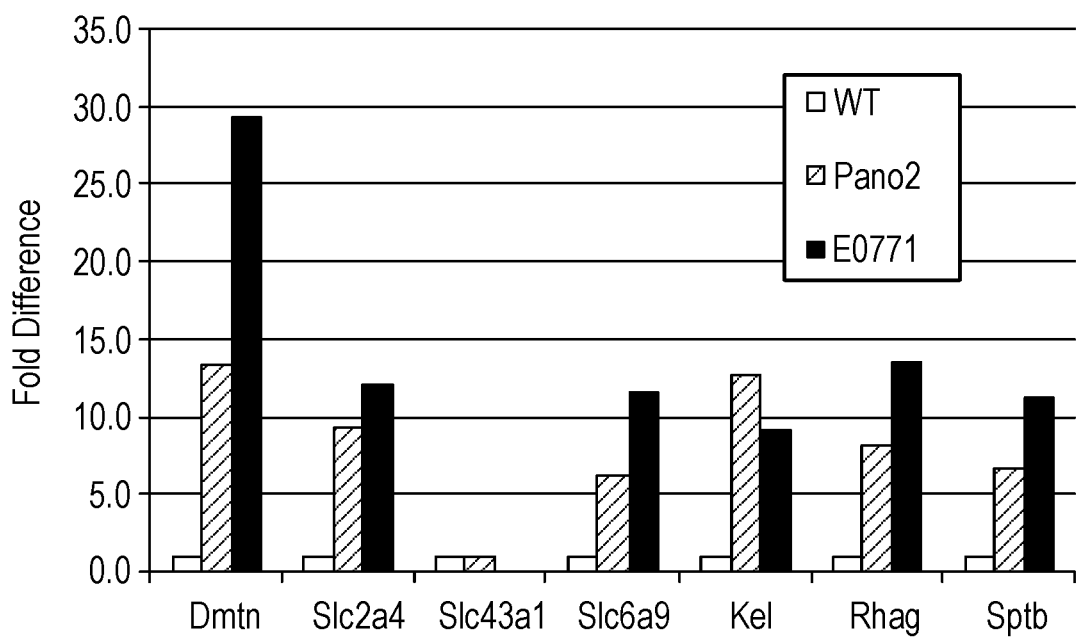
Figure 2A:
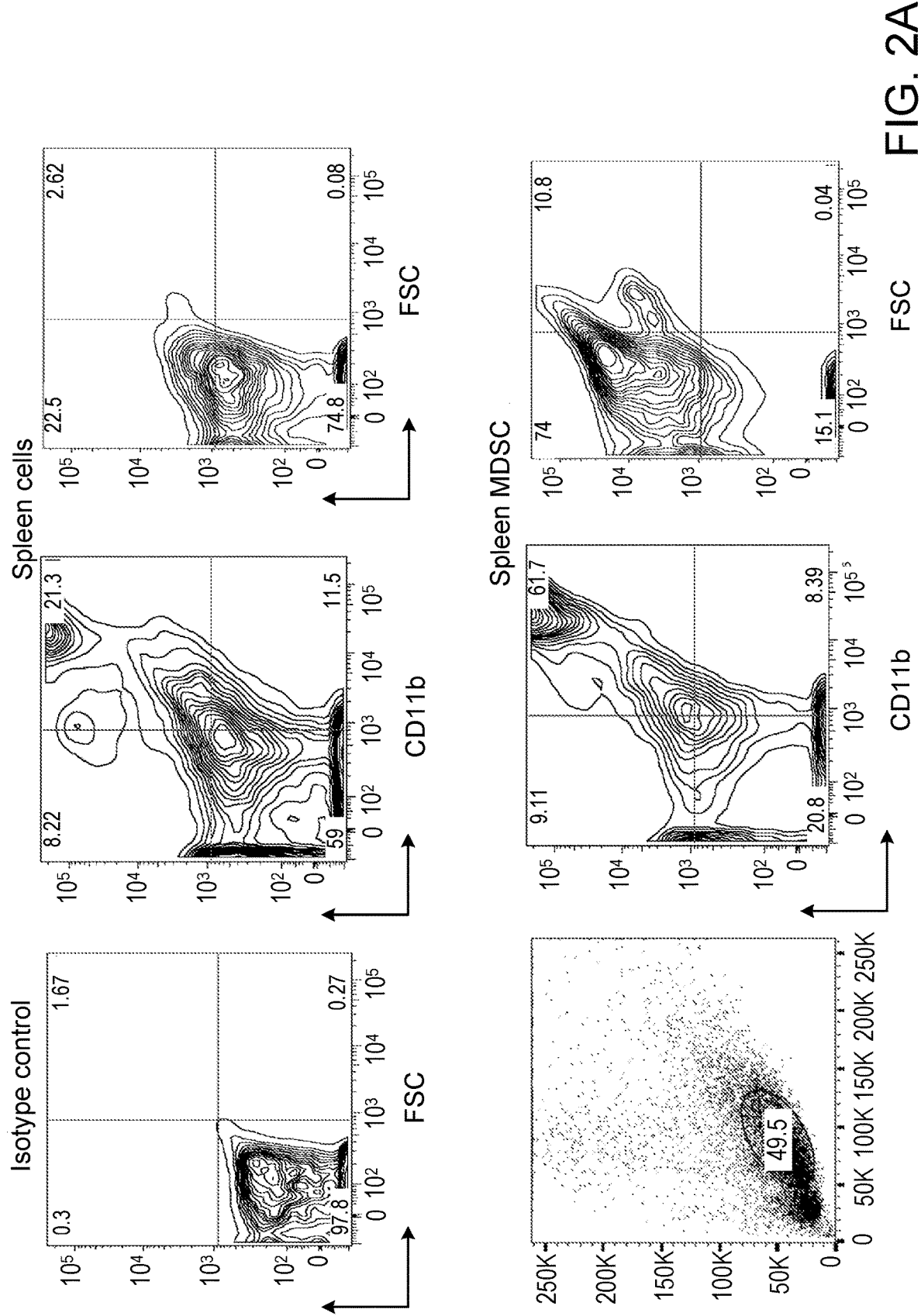
FIGS. 2A-B. MDSCs in Pan02 tumor-bearing mice. Expression of ICAM4 and CD11b$^+$Gr-1$^+$ in cells isolated from spleens and tumors of Pan02 injected mice after three weeks. A, Isotype control staining of spleen cells (left); CD11$^+$Gr-1$^+$ and ICAM4$^+$ cells in spleen (top) and in MDSC isolated from spleens of tumor-bearing mice (middle). B, CD11b$^+$Gr-1$^+$ and ICAM4$^+$ cells from intratumoral MDSC isolated from Pan02 injected tumor-bearing mice (bottom). Intratumoral cells were isolated following digestion of tumors, followed by isolation of MDSCs as described in Materials & Methods. Spleens and tumors were collected from mice after three weeks post tumor implantation. Data shows ICAM4 expression in either total spleen cells or in cells following MDSC isolation. Representative examples of flow cytometric analyses are presented from five separate experiments.
Figure 2B:
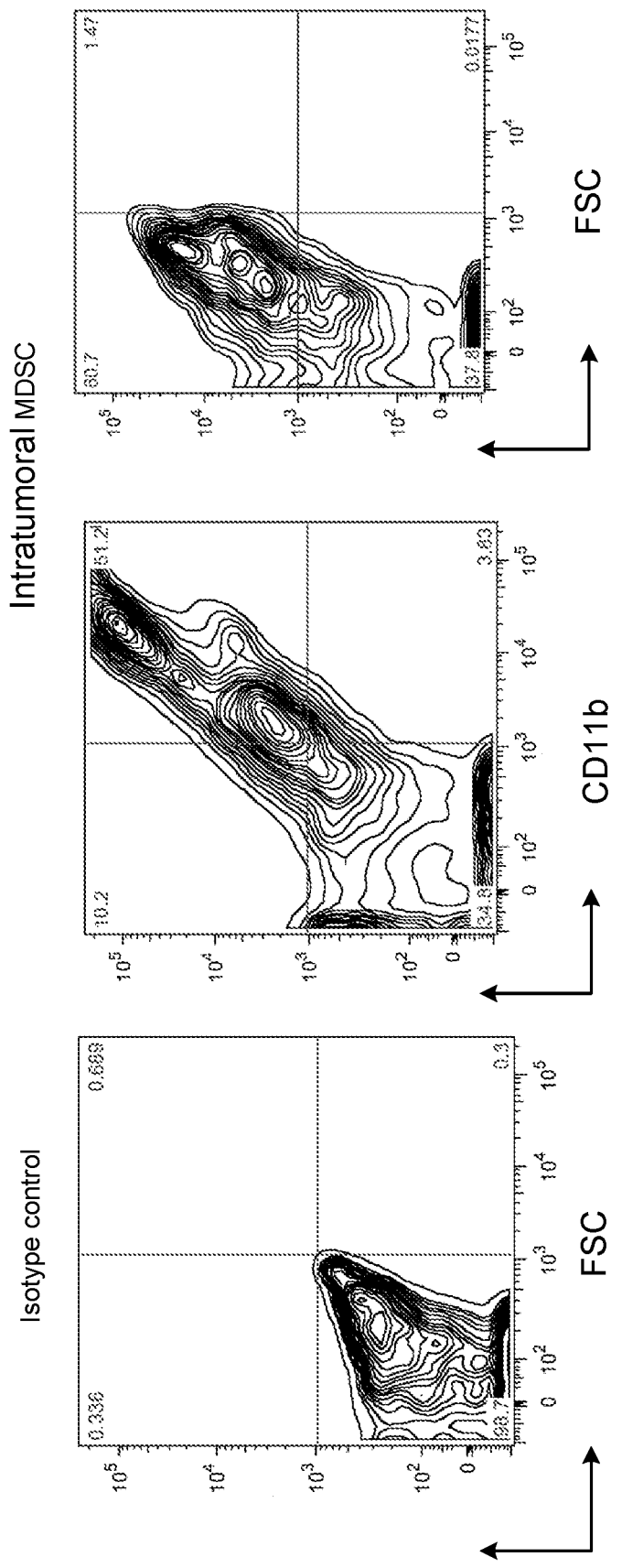
Figure 13:
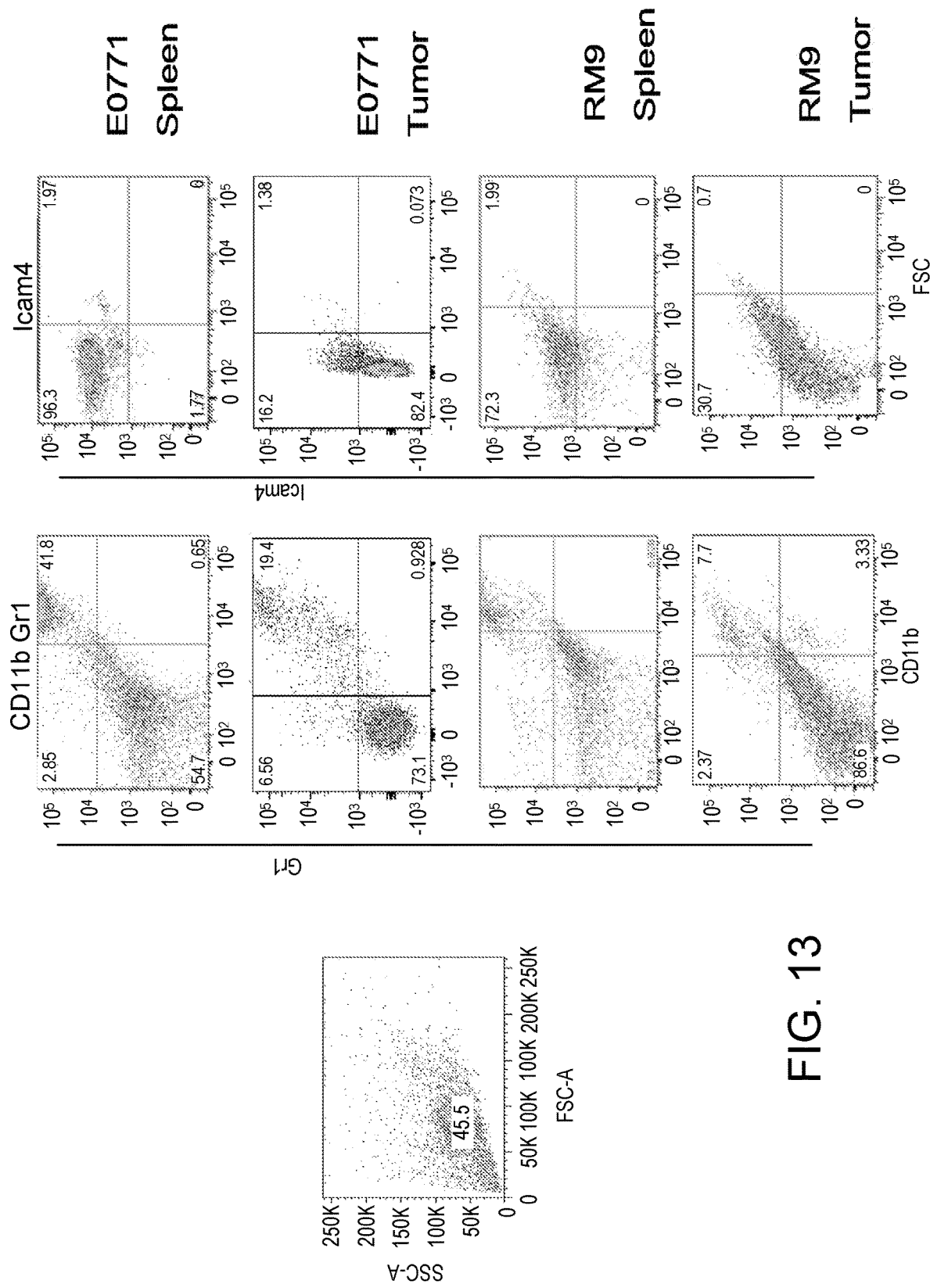
FIG. 13. Expression of ICAM4 in MDSCs isolated from spleens and tumor infiltrating cells (TIC) from E0771 (top) and RM9 (bottom) cells injected mice after three weeks. Left, gating strategy of isolated MDSCs. CD11$^+$Gr-1$^+$ staining of cells (middle) and ICAM4$^+$ (right) staining of cells.

Example 2. ICAM4 Protein Expression is Detected in MDSCs from Multiple Mouse Tumor Models It has been demonstrated that MDSCs accumulate in human tumors and in various animal tumor models. We validated microarray data that demonstrated differential expression of ICAM4 RNA in 3 tumor models, viz. pancreatic and breast cancer (E0771), and in B16 melanoma (FIG. 1B). We now wished to assess protein expression in these models and to extend our analysis to an additional tumor model (RM-9, a prostate cancer model), and to assess ICAM4 expression cells infiltrating the tumor. C57Bl/6 mice injected with Pan02, E0771 (breast cancer) and RM-9 cells developed tumors that grew at varying rates but were always associated with increased immunosuppressive cell infiltrates in the tumors and in spleens (FIG. 2 and FIG. 13). Spleens isolated from Pan02 tumor-bearing animals were found to have significantly higher frequencies of MDSCs (as demonstrated by staining with CD11b and Gr-1 antibodies) when observations were made three weeks after subcutaneous injection of cells (FIG. 2A). While most of the MDSCs were Gr-$1^{hi}$ CD11$b^{lo}$, a population of Gr-$1^{lo}$CD11$b^{hi}$ is also evident in the MDSC population. Similarly, comparable higher frequencies of ICAM4 positive cells could be demonstrated in these splenocytes (21.3% CD11$b^+$Gr-$1^+$ cells and 25.1% ICAM$4^+$ cells). Staining of MDSC following isolation from splenocytes demonstrated (FIG. 2, middle panel) that most of the CD11$b^+$Gr-$1^+$ cells were ICAM4+ (~85%). A similar pattern of MDSC accumulation was observed in mice transplanted with E0771 cells, where the frequencies of CD11$b^+$ Gr-$1^+$ cells was 41.8% of isolated MDSC, and 96.3% of ICAM4+ cells in purified MDSCs (FIG. 13). Animals transplanted with RM-9 tumors, demonstrated similarly frequencies of 19.4% CD11$b^+$Gr-$1^+$ cells in the spleen that were about 74% ICAM$4^+$ (FIG. 13).

It has been reported previously that MDSC accumulate at multiple sites in tumor-bearing animals including in spleens, livers and tumors. Tumors (Pan02, E0771) were excised after 3 weeks post-injection and subjected to digestion with collagenase and hyaluronidase to isolate infiltrating cells. MDSC (determined by staining for CD11$b^+$Gr-$1^+$ cells) were found to be present as tumor infiltrates (51.2%) in the Pan02 tumors (FIG. 2). A distinct sub-population of CD11$b^{hi}$ cells was observed in this population as opposed to the splenic MDSC where this population was less distinguishable. Staining of tumor infiltrating MDSC revealed a distinct population of ICAM$4^+$ cells (62.1%) suggesting that ICAM4 is a marker for tumor infiltrating MDSC. Interestingly, the ICAM$4^+$ positive cells had $^{hi}$ and $^{lo}$ subsets that could represent separate populations of tumor-infiltrating cells. Analysis of tumor infiltrating cells in other tumor models revealed similar but lower frequency of CD11$b^+$Gr-$1^+$ cells (23.4% for E0771 and 7.7% for RM-9). Staining of the infiltrating cells showed that they were also positive for ICAM$4^+$. Again, the frequency of ICAM$4^+$ cells in the tumor infiltrate was much lower than in Pan02 tumor infiltrates (17.5% for E0771 and 31.4% for RM-9) (FIG. 13).

Figure 3:
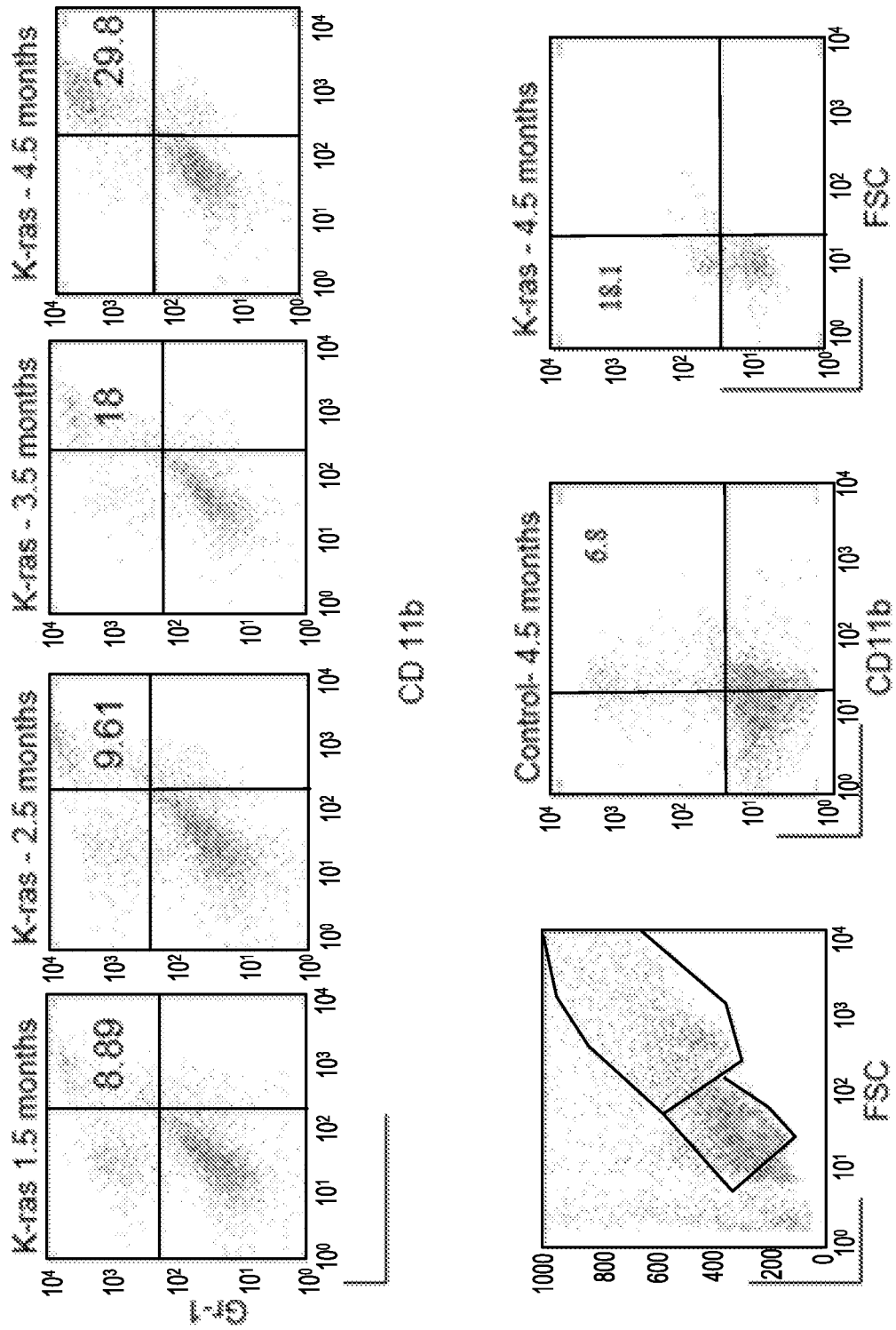
FIG. 3. Appearance of MDSCs in Kras$^{G12D}$x PDX-1-Cre mice. Animals were sacrificed at different ages and observed for appearance of PanINs and adenocarcinomas. (Top): spleens isolated from mouse at different ages were used for staining of cells for CD11b$^+$Gr-1$^+$ and analyzed by FACS. (Bottom): gating strategy (left), spleen cells from control (Cre$^+$) mice stained with CD11b and Gr-1 antibodies (middle), spleen cells from PDXCre/K-ras mice at 4.5 months stained for ICAM4 expression (right). Data representative of FACS staining of spleen cells from three animals in one experiment.
Figure 4A:
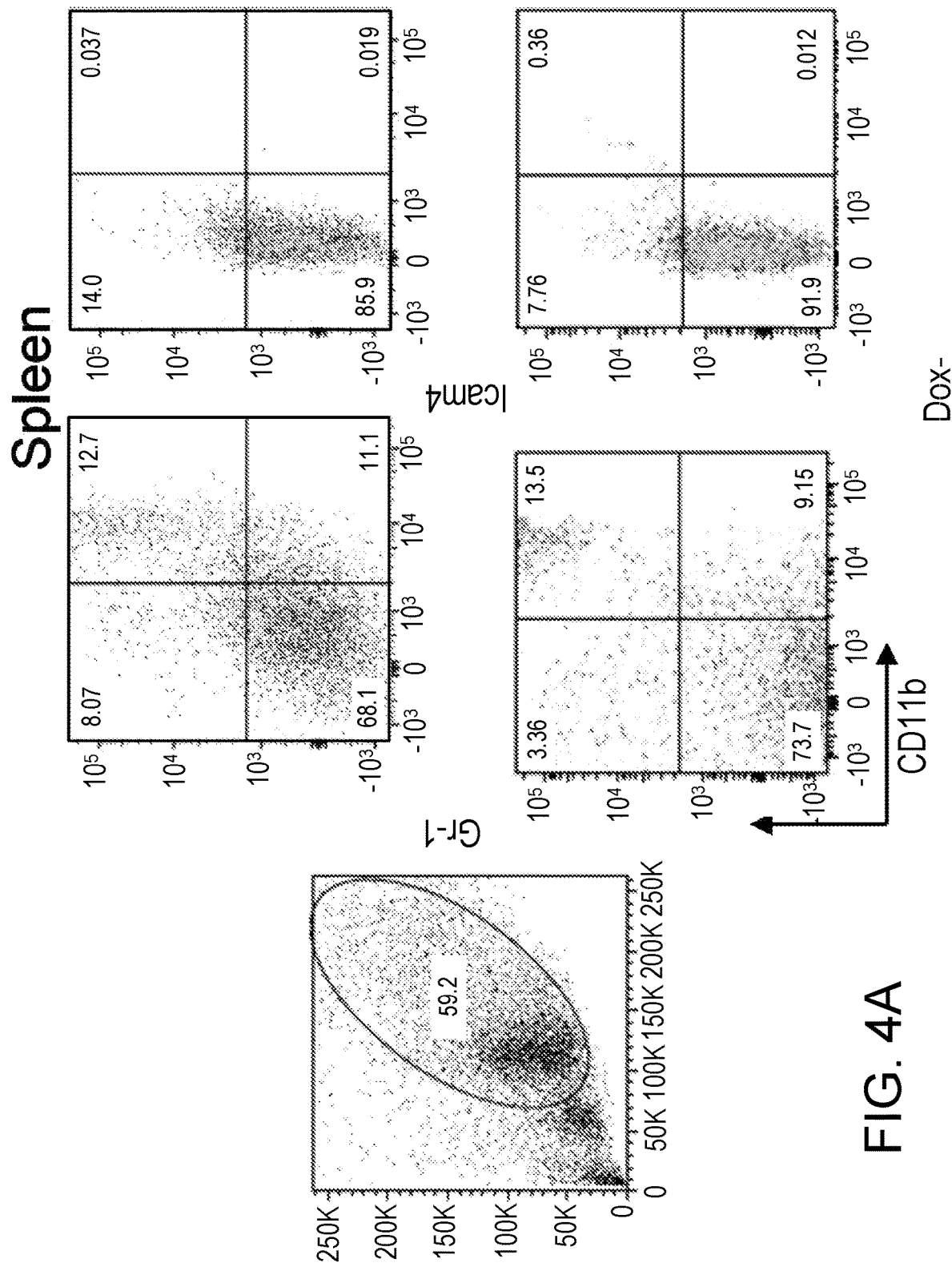
FIGS. 4A-C. ICAM4 expression in conditional activated MMTV-rtTA/TetO-NeuNT mammary tumors. Gating strategy for spleen cells (left). Staining of spleen (A) and tumor-infiltrating (B) cells from tumor-bearing mice with CD11b and Gr-1 and ICAM4 antibodies. (C) Frequency of lymphocytes infiltrating dox+ and dox− spleens and tumors following staining with CD11b and Gr-1 or ICAM4 specific antibodies (p value<0.05). Results are representative of three separate experiments.
Figure 4B:
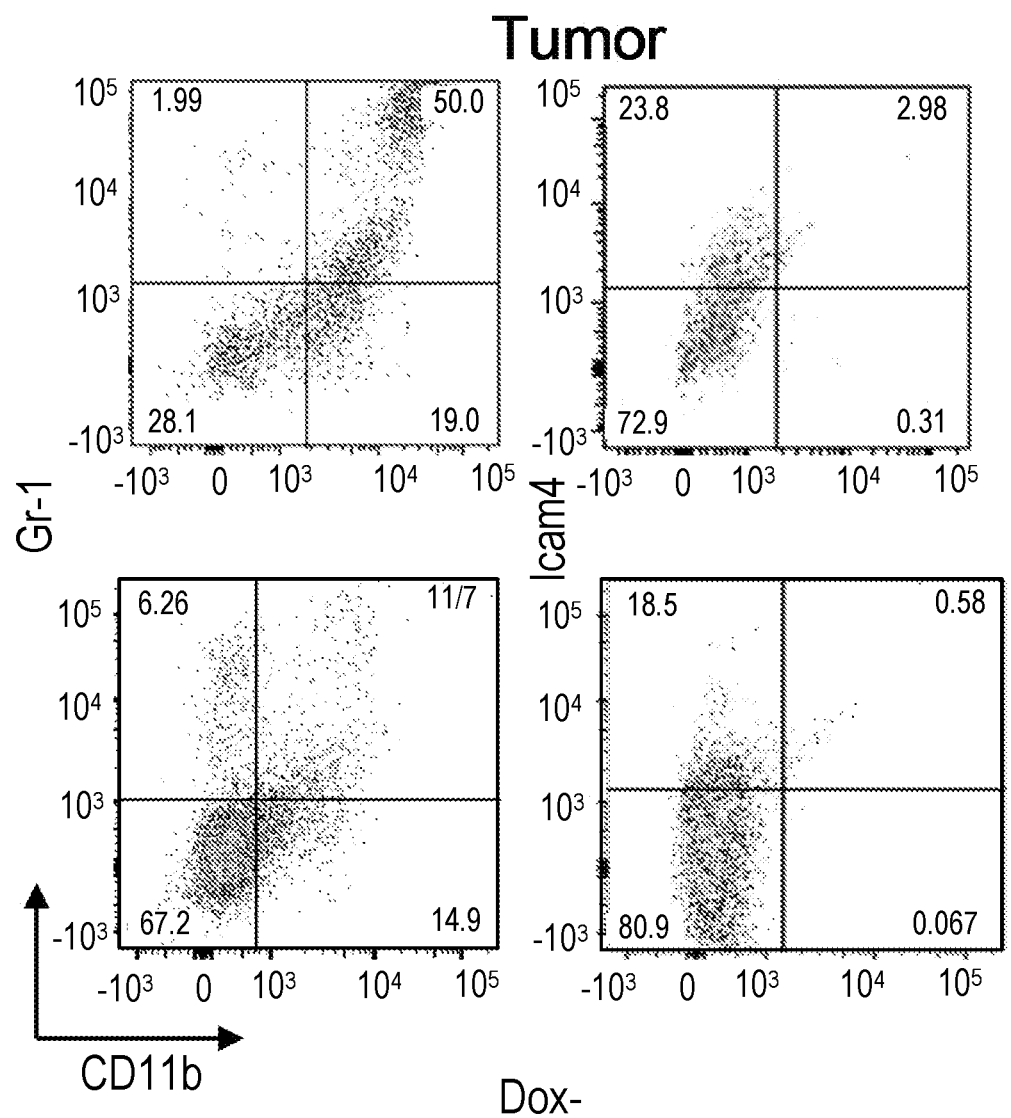
Figure 4C:
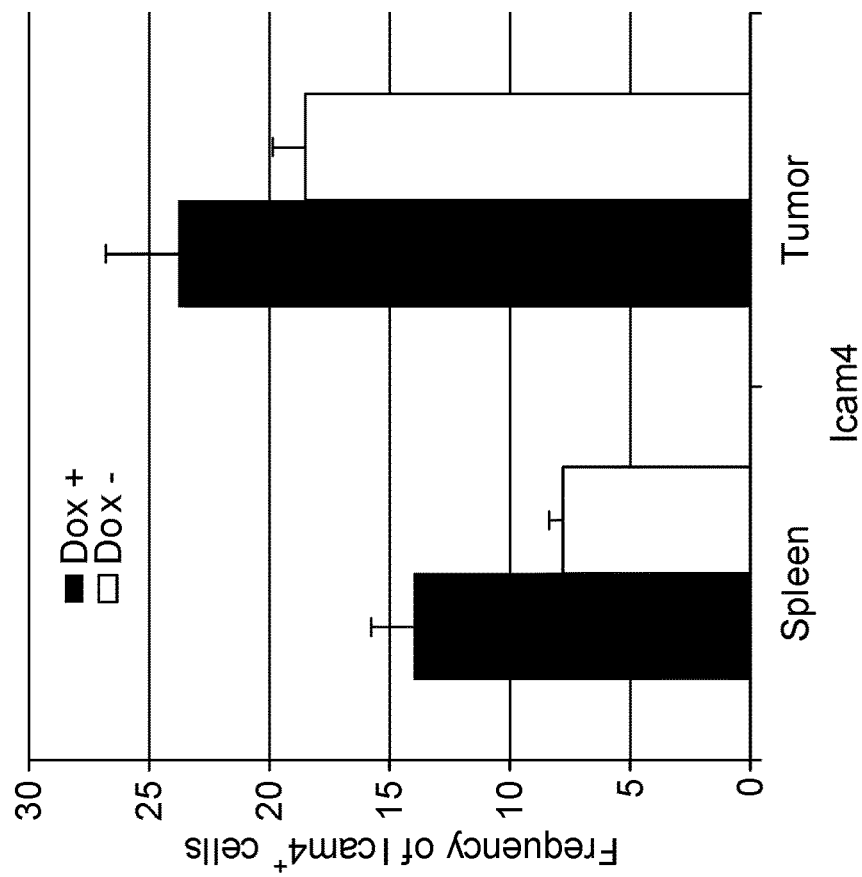
Figure 4C:
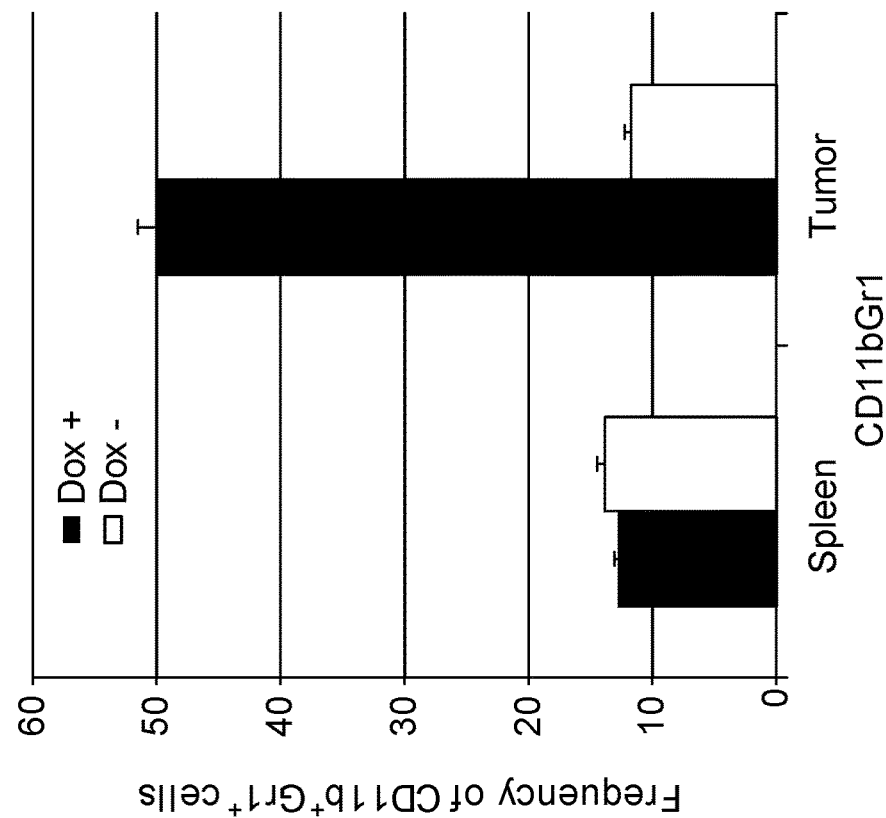

Example 3. Pancreatic and Breast Tumors in Genetically Engineered Mouse Models Carry ICAM$4^+$ MDSC We have also examined ICAM4 expression in myeloid-derived suppressor cells isolated in a genetic model of pancreatic cancer (LSL-KrasG12D, Pdx-1-Cre mice). In this model CD11$b^+$Gr-$1^+$ positive cells make up a population of large, granular cells that appear in animals with tumors and these CD11$b^+$Gr-$1^+$ cells express ICAM4 as was observed in the transplant tumor models. Results presented in FIG. 3 show that the KrasG12D, Pdx-1-Cre mice had a large infiltration of MDSCs that could be monitored as CD11$b^+$ Gr-$1^+$ cells (29.8%) or ICAM4+ cells (21.5%).

Figure 5:
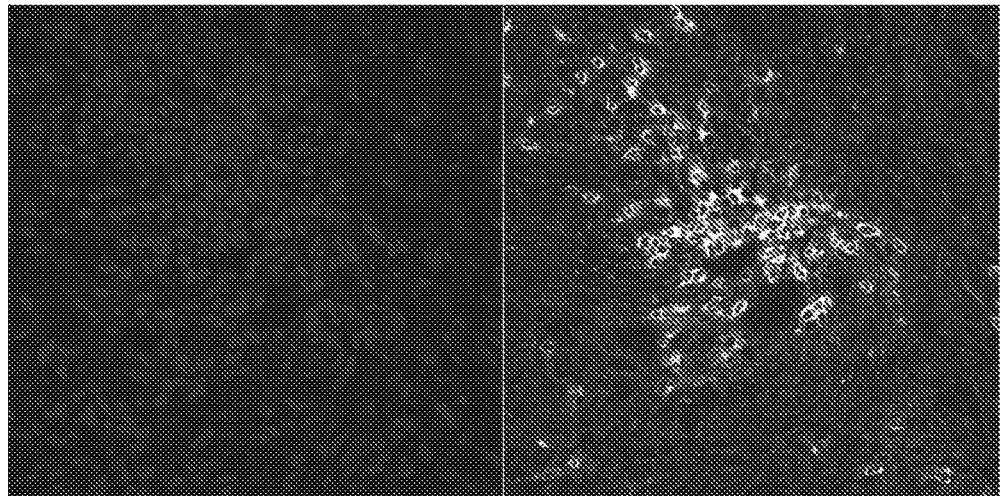
FIG. 5. ICAM4 expression in tumor infiltrating cells following Her2 activation (Top) and de-induction (Bottom). Tumors were isolated from animals receiving doxycycline treatment as described in Methods section and tumor sections were stained with appropriate antibodies. In case of Her2 de-induction, animals with significant tumors were withdrawn from doxycycline treatment and regressing tumors were flash frozen and subjected to IF staining. Figures represent similar data obtained from two separate experiments.
Figure 5:
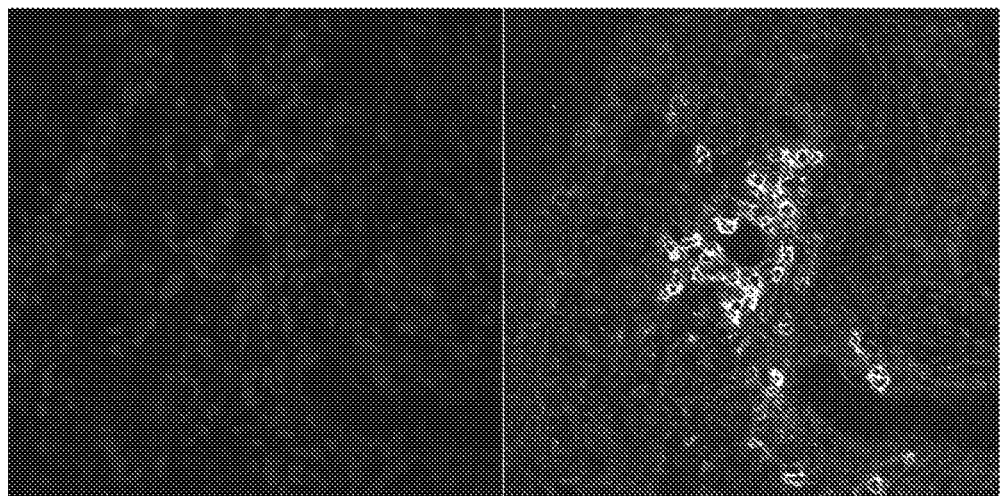

As a separate genetic model, we have generated a colony of bitransgenic MMTV-rtTA/TetO-NeuNT mice that express mammary-specific activated Neu in a doxycycline-dependent manner. Following chronic induction of Neu, animals develop invasive nodular carcinomas similar to human breast cancer within 2 months. Interestingly, upon dox withdrawal, tumors regress rapidly and, in only a small sub-population, recurrence takes place despite de-induction of Neu (data not shown). Tumors were harvested when they reached <200 mm$^2$ in chronically Neu-induced animals as well as from an independent set of animals that underwent doxycycline withdrawal for 72 h and showed signs of regression. Tumor tissue was digested with enzymes as described (24), and frequency of various subsets of tumor infiltrating lymphocytes was analyzed following staining with appropriate antibodies. It was observed that Neu-induced tumors had a large population of infiltrating cells made up of CD11$b^+$Gr1$^+$ cells that also stained for ICAM4 (FIG. 4). Interestingly, the TILs isolated from regressing tumors demonstrated a dramatic decrease in MDSCs from 44±3 to 12±6%. Immunofluorescence staining revealed expression of ICAM$4^+$ cells in tumor sections along with a trend towards decreased in this population in regressing tumors (FIG. 5).

Example 4. MDSC Generated In Vitro from Mouse Bone Marrow Express ICAM4

Figure 14B:
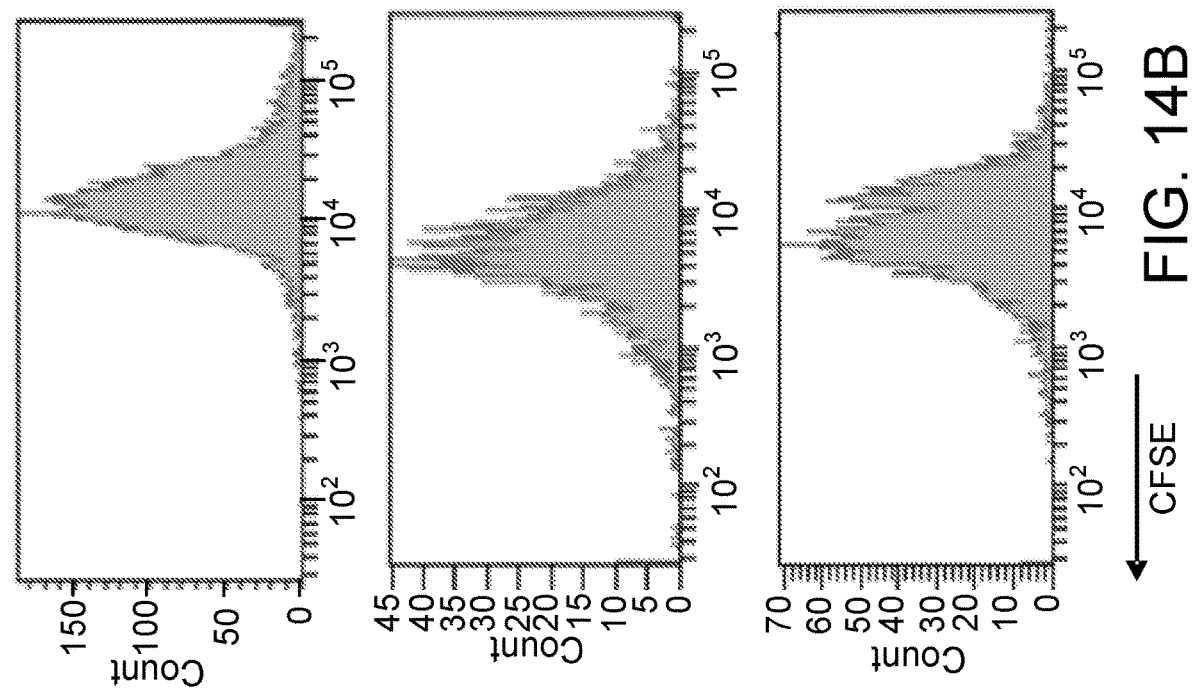
FIGS. 14A-D. Generation of mouse bone marrow-derived MDSC with immune suppressive function. A, Expression of iNOS and ArgI and ArgII genes in BM-MDSC; B, Inhibition of proliferation of CD4 cells by MDSC co-cultured with T cells for 5 d (1:1 ratio); C, Inhibition of perforin levels in CD8 T cells by MDSC following 24 h co-culture at 1:1 ratio; D, Inhibition of NK cell cytotoxicity against YAC-1 target in the presence of MDSC.
Figure 14A:
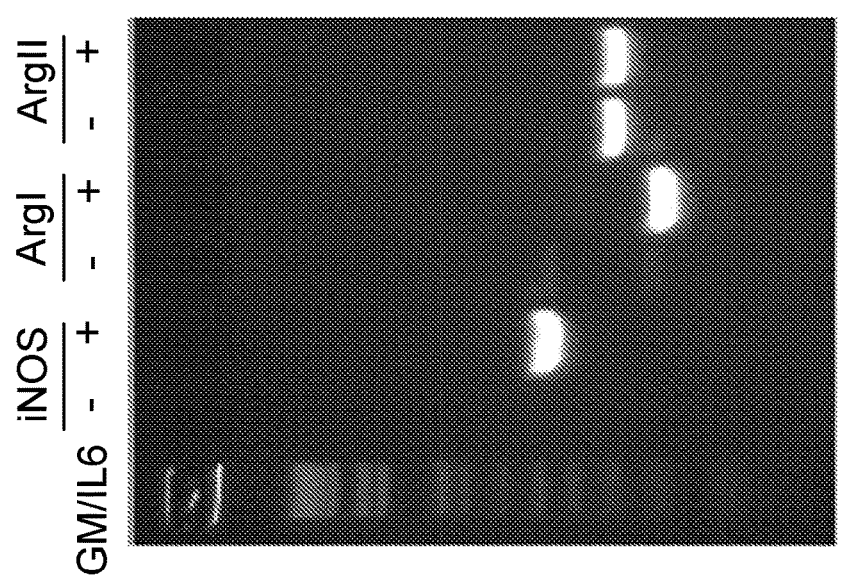
Figure 14C:
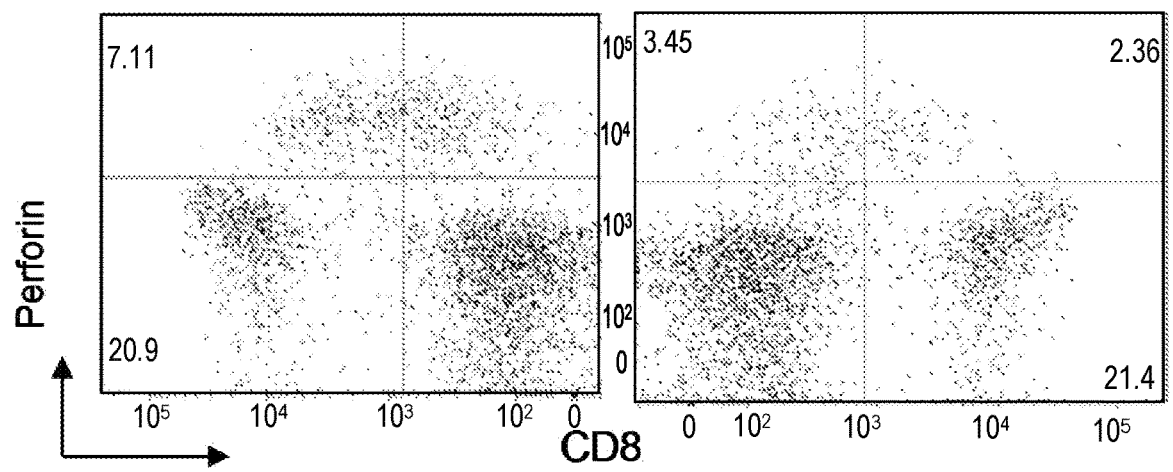
Figure 14D:
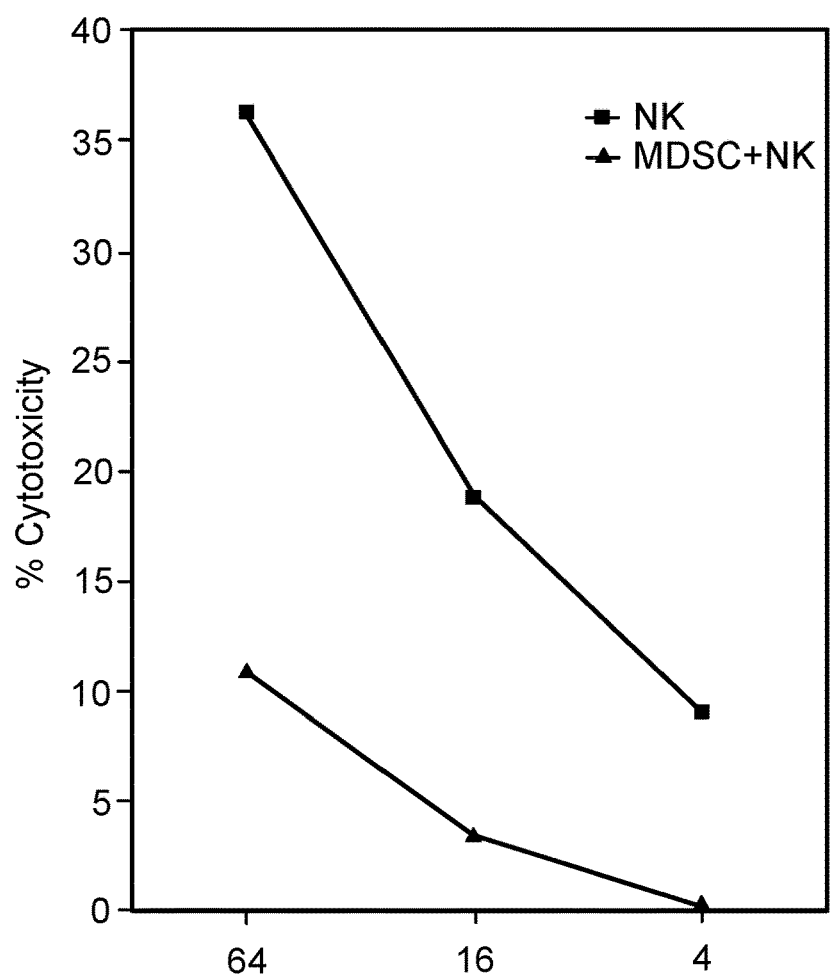

We have shown previously that mouse bone marrow cells could be converted to immunosuppressive cells in vitro. We have generated such MDSCs in vitro (designated BM-MDSC): we started with mouse bone marrow cells and incubated them with GM-CSF/IL-6 for 4 days and characterized these cells in a number of ways. BM-MDSC exhibited increased expression of NOS2 and Arg1 (FIG. 14A) and were highly immunosuppressive as demonstrated by their ability to inhibit proliferation of CD4 cells activated with anti-CD3 and anti-CD28 and inhibit IFNγ and perforin production in CD8 cells (FIG. 14B, C). They also inhibited NK cytotoxicity (FIG. 14D). Briefly, BM-MDSCs were co-cultured with CD4 T cells in anti-CD3/CD28 coated plates at different ratios. Proliferation was determined following staining of cells with Alamar Blue or by CFSE staining. CD8 cells were cultured with BM-MDSC for 24 h at a 1:1 ratio and then stained for IFNγ and perforin levels and analyzed by FACS.

Figure 6:
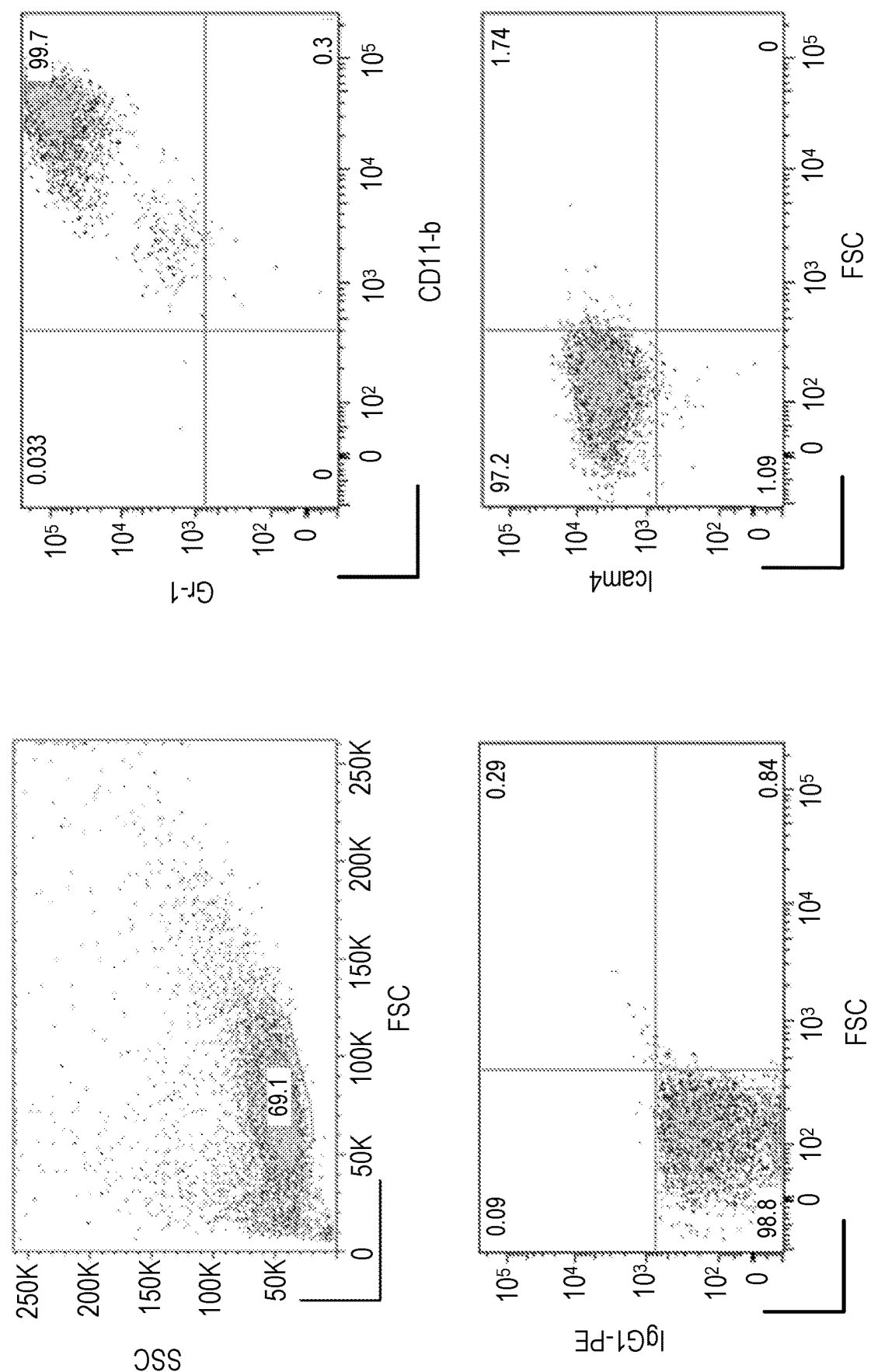
FIG. 6. Expression of markers on mouse bone marrow-derived MDSC generated in vitro. CD11b$^+$Gr-1$^+$ cells were isolated from BM cells after 4 d of culture in CM from Pan02 cells, stained with FITC or PE-conjugated appropriate antibodies and subjected to FACS analysis. Left, gating of cells (top) and isotype control (bottom). Right, CD11b, Gr-1 staining (top) and ICAM4 staining of cells following isolation of MDSCs. Data represents one of five such experiments.

Importantly, culturing BM cells in GM-CSF/IL-6 for 4 d, resulted in the generation of these immunosuppressive cells that could be defined either by CD11$b^+$Gr-$1^+$ staining or with ICAM4 (FIG. 6).

Example 5. Human PBMC-Derived Immunosuppressive Cells Express ICAM4

Figure 7:
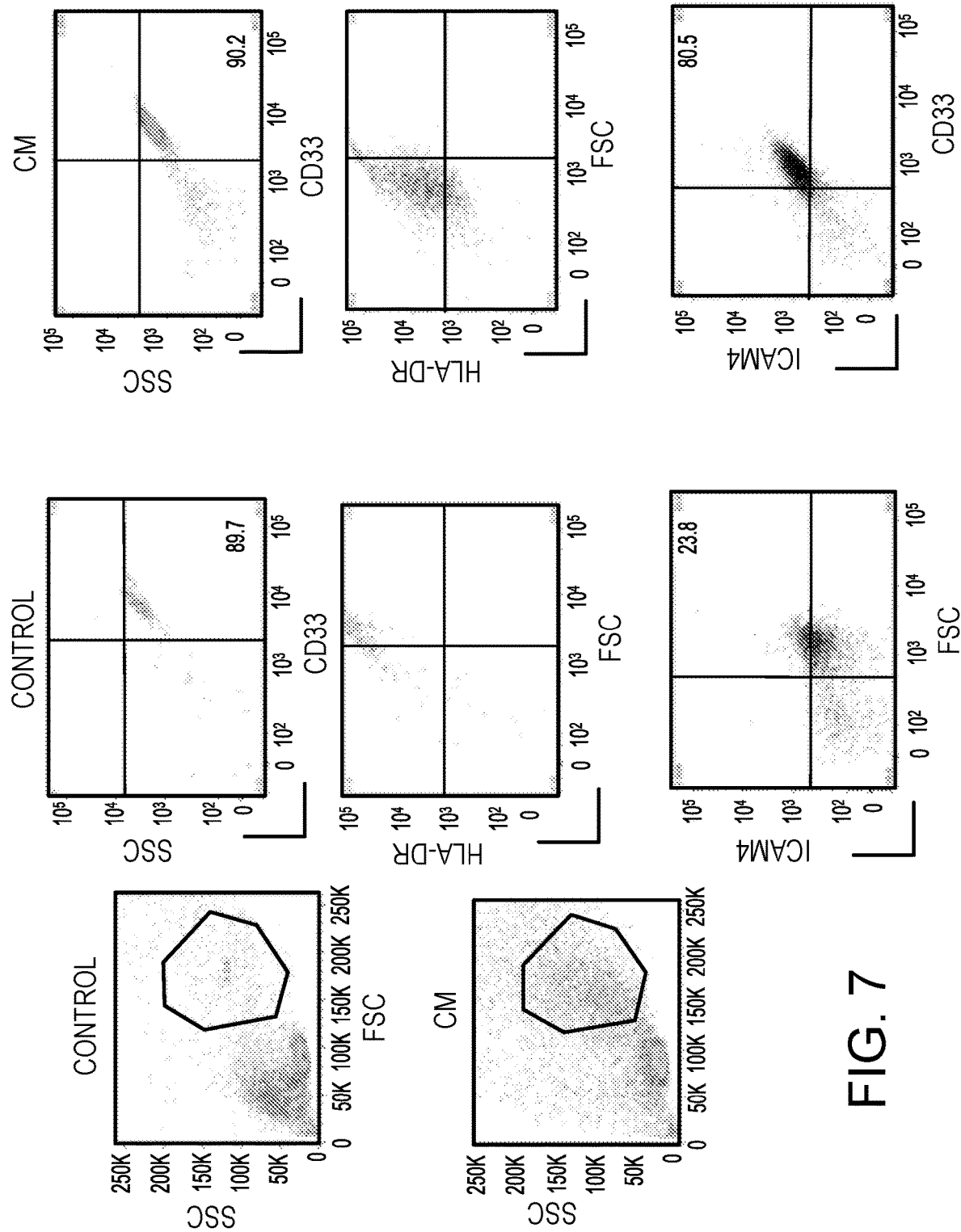
FIG. 7. Normal donor PBMC were cultured in the presence of CM from WM1617 melanoma cell culture for 4 d. Left, FSC/SSC plots to show gated MDSC population; Middle, PBMC cultured in media without CM (in complete RPMI media only); Right, PBMC cultured for 4 days in media with CM from WM1617 melanoma cell culture. In all cases cells were collected and stained with appropriate antibodies against CD33, HLA-DR and ICAM4 and analyzed by FACS. Results are representative of three separate experiments.
Figure 8A:
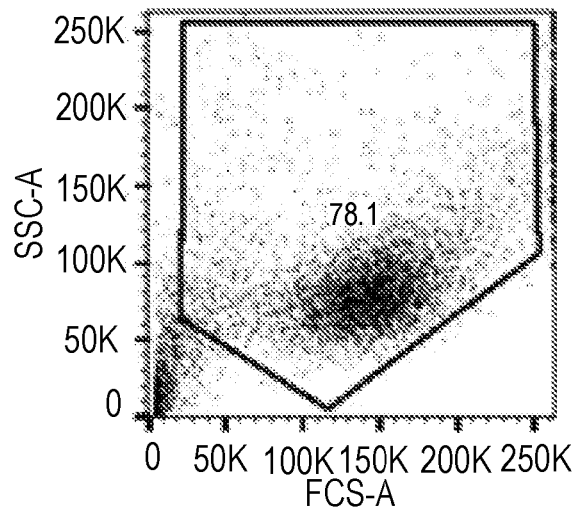
FIGS. 8A-C. Co-expression of ICAM4 with Ly6C or Ly6G in mouse MDSCs. A, expression of ICAM4 with Ly6C or Ly6G on mouse bone marrow-derived MDSC generated in vitro with GM-CSF and IL-6. B, expression of ICAM4 with Ly6C or Ly6G in MDSCs isolated from spleens of E0771 tumor-bearing mice. Three weeks following injection of E0771 cells, spleens were harvested and MDSC were isolated as described in Methods. Cells were stained with appropriate antibodies. C, expression of ICAM4 in spleen cells isolated from E0771 tumor-bearing mice after 3 weeks following injection of tumor cells. Spleen cells were isolated from mice and stained with appropriate antibodies. Data is representative for three separate animals.
Figure 8A:
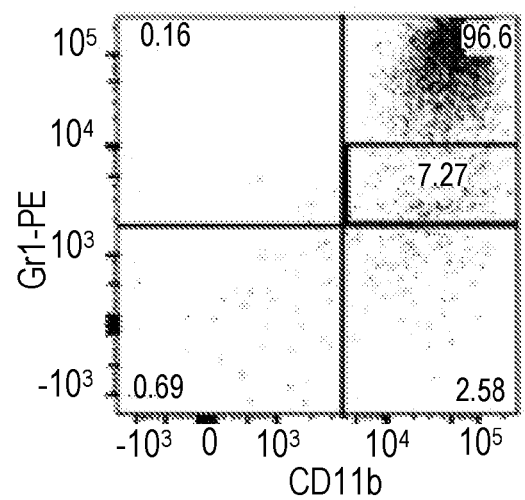
Figure 8A:
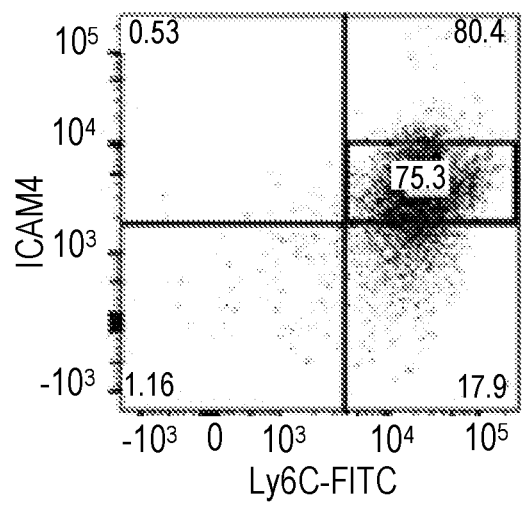
Figure 8A:
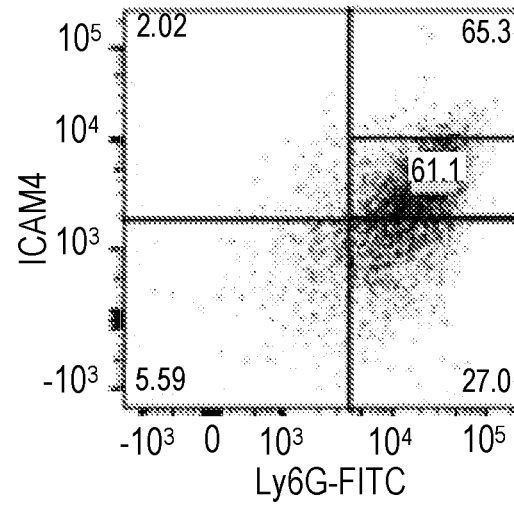
Figure 8B:
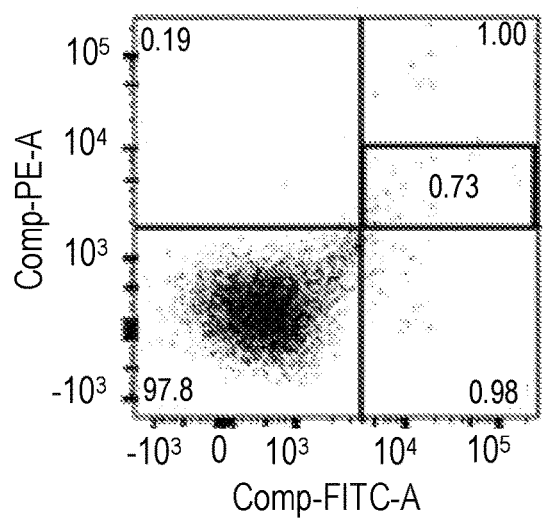
Figure 8B:
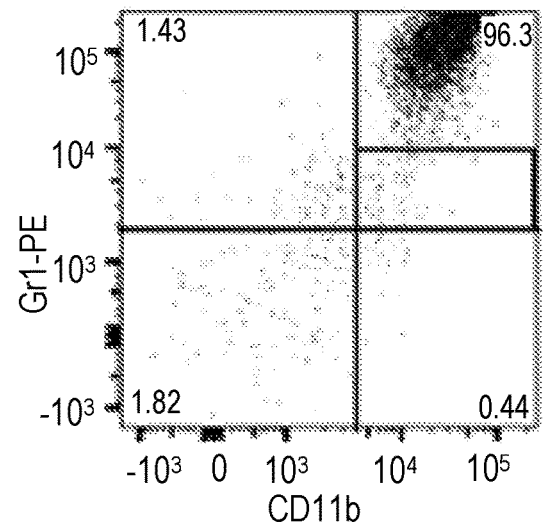
Figure 8B:
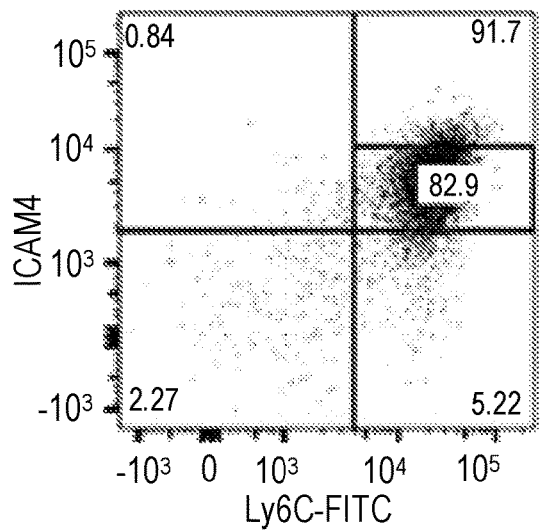
Figure 8B:
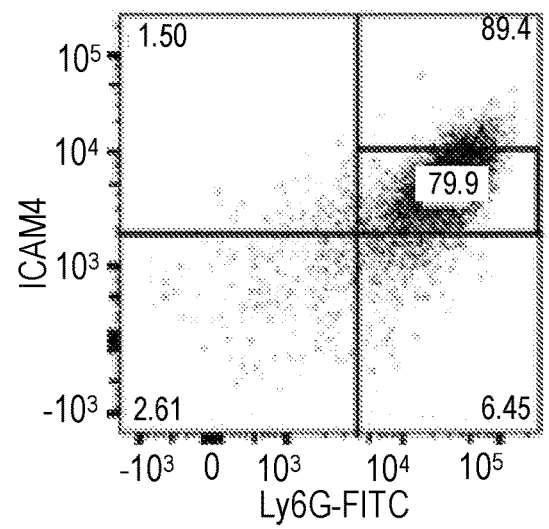
Figure 8C:
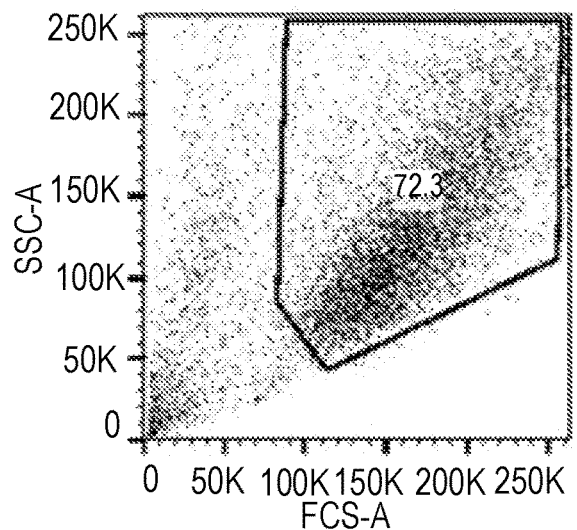
Figure 8C:
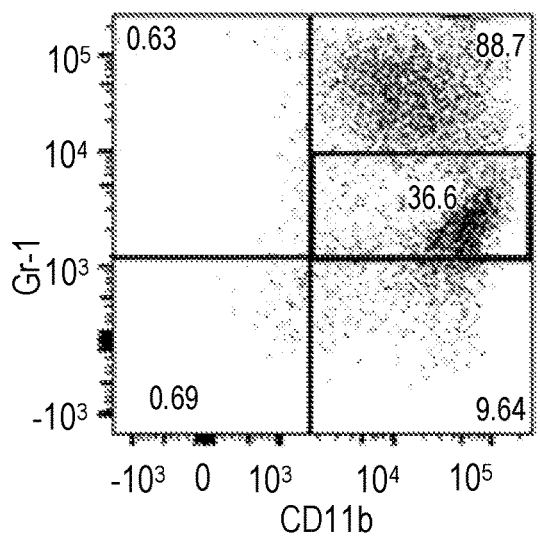
Figure 8C:
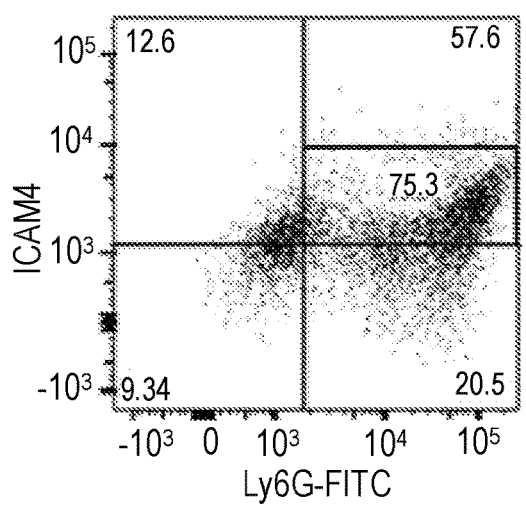
Figure 8C:
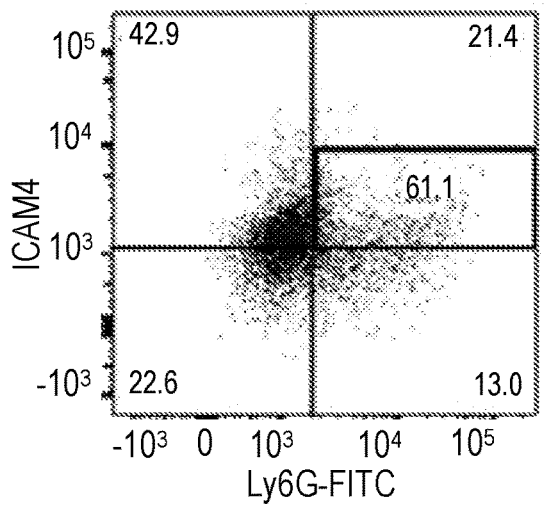
Figures 15A, 15B:
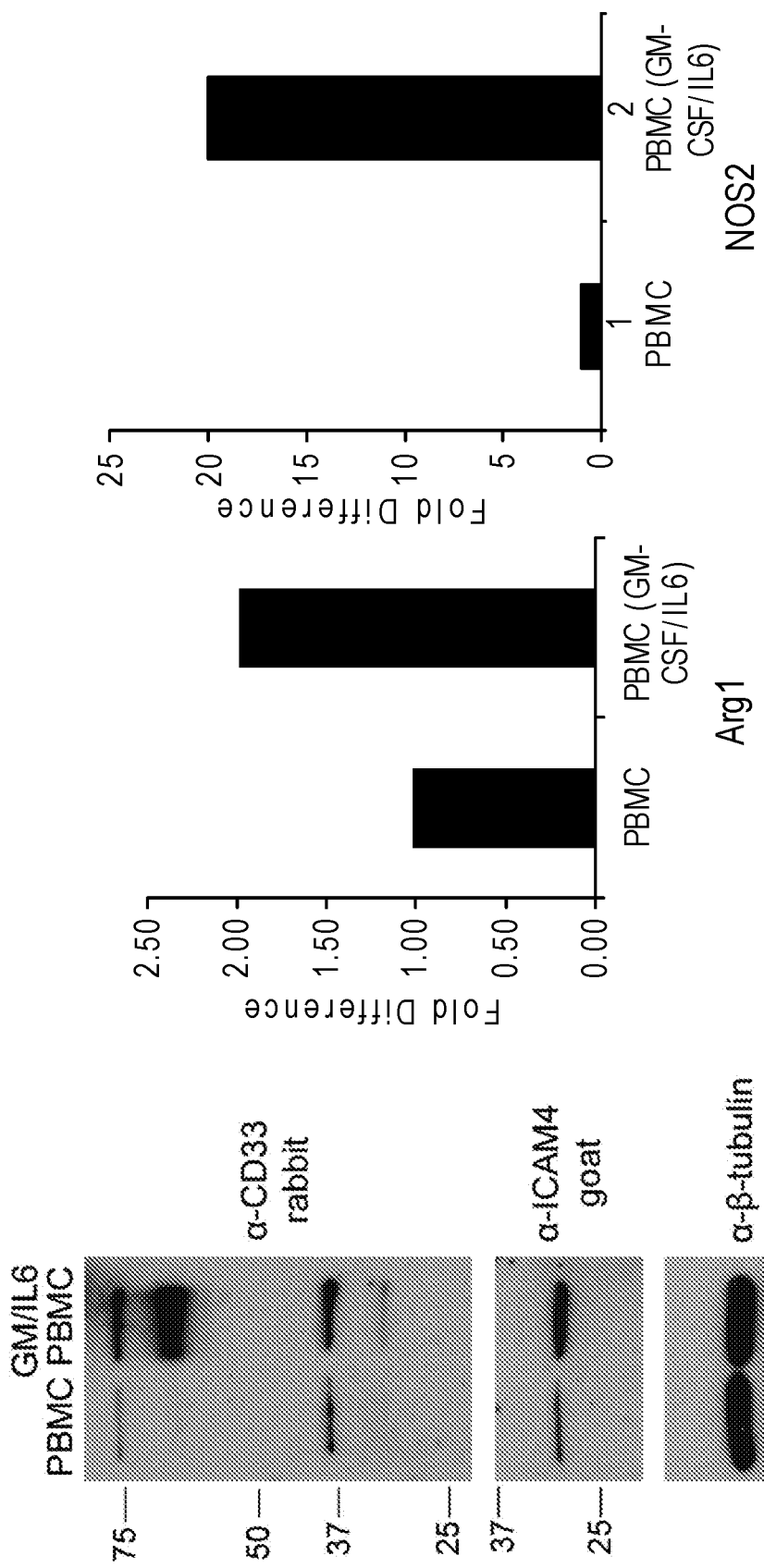
FIG. 15. ICAM4 expression in PBMC-derived MDSCs with immunosuppressive functions. PBMC isolated from healthy volunteers were cultured for 4 days with GM-CSF and IL-6. (A) PBMC-derived MDSC were subjected to Western blot analysis for expression of CD33 and ICAM4. (B) CD33$^+$ ICAM4$^+$ were tested for their ability to suppress proliferation of CD4 (1:1 ratio of MDSC:T cells) as determined by Alamar blue staining. Comparison is shown between MDSC generated by GM-CSF/IL-6, CM from WM1617 melanoma cells and CM from MDA-MB236 cells. (C) Expression of NOS2 and Arg1 in MDSCs differentiated with GM-CSF and IL-6 from PBMC in culture for 4 d. (D) Inhibition of NK cell cytotoxicity against K562 target in the presence of MDSC generated from PBMC treated with GM-CSF and IL-6.
Figure 15C:
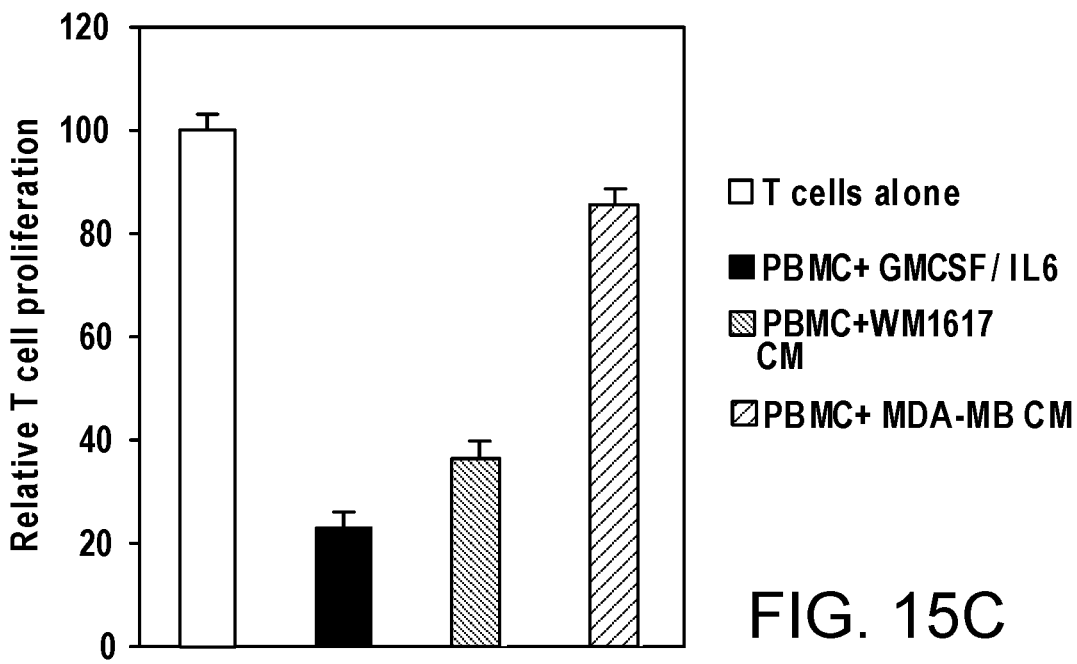
Figure 15D:
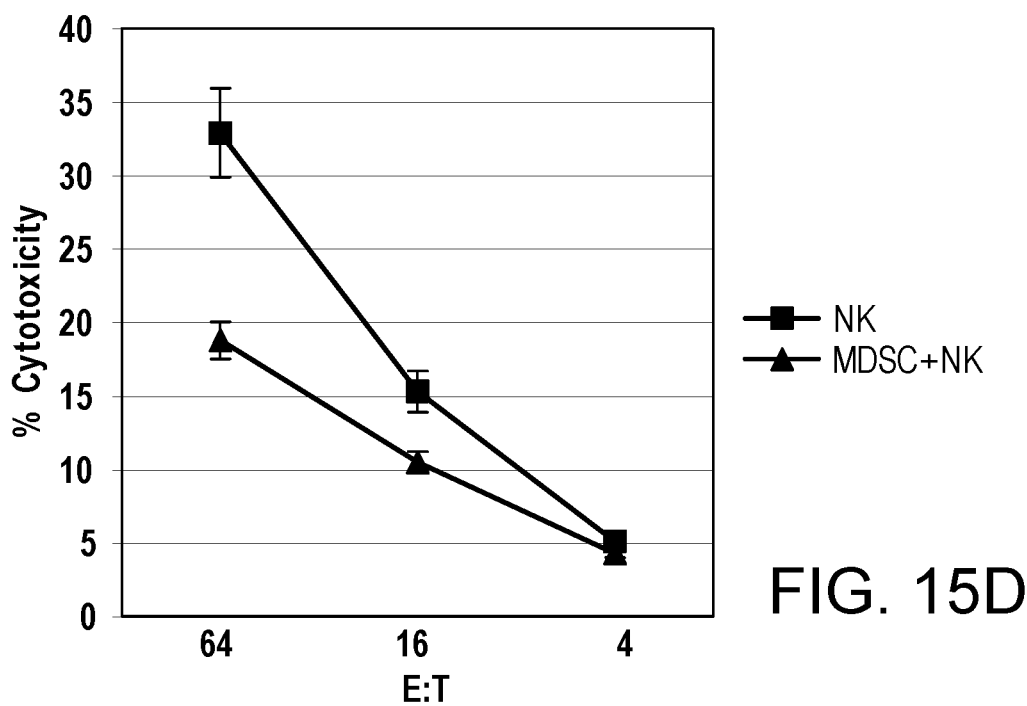

Less clearly defined in human cancer, polymorphonuclear (CD11$b^+$CD15$^+$CD14$^-$) or monocytic(CD11$b^+$CD14$^+$ HLA-DR$^{lo}$ populations of MDSCs have been described. Correlation of these markers to functional immunosuppressive activities has been limited. Also, it has been previously demonstrated that human PBMC treated with either conditioned media from cancer cells or individual cytokines and growth factors, generate an immunosuppressive phenotype and function (24, 39). We have determined expression of ICAM4 on MDSC generated from PBMC that were either cultured with GM-CSF and IL-6 or with conditioned media from human cancer cell lines. These cells behaved as MDSCs in that they were CD33$^+$, HLA-DR$^{lo}$ and were functionally immunosuppressive (based on inhibition of CD4 T cell proliferation and IFNg and perforin expression on CD8 T cells, similar to the mouse system). Interestingly, ICAM4 was expressed at high levels in these cells paralleling increased expression of CD33$^+$HLA-DR$^{lo}$ and serving as an independent marker of suppressive activity, similar to mouse MDSC and BM-MDSC (FIG. 7, FIG. 15).

In order to confirm that immunosuppressive function was associated with ICAM4$^+$ cells, we isolated ICAM4$^+$ cells by cell sorting and used these cells to assess whether they suppressed T cell function in vitro. ICAM4$^+$ cells isolated from GM-CSF and IL-6 mediated MDSC were able to suppress CD4 proliferation and suppressed autologous CD8 function in an Ag-nonspecific manner (data not shown).

Example 6. ICAM4+ Expression is Associated with a 'Monocytic' MDSC Population

In order to define ICAM4 association with a specific population of MDSCs, we isolated CD11b$^+$Gr-1$^+$ cells from both BM-derived MDSCs that were generated in culture using GM-CSF and IL-6 (as described earlier), as well from spleens of E0771 tumor-bearing mice (FIG. 8). We observed that most of these cells that were CD11b$^+$Gr-1$^+$ (~97%) were similarly positive for Ly6C$^+$ICAM4$^+$ (80.4%) and Ly6G$^+$ICAM4$^+$ (65.3%) (FIG. 8A, B). An almost similar trend was observed with MDSC isolated from E0771 tumor-bearing mice (FIG. 8B). This data suggested that either ICAM4 was co-expressed with both Ly6C and Ly6G antigens or that Ly6G antibody, used in sorting, was also binding to Ly6C$^+$ cells. To resolve this question, we sorted for Ly6G and Ly6C cells and then stained these populations with ICAM4 antibody. FACS analysis of such cells demonstrated equal frequencies of Ly6C$^+$ICAM4$^+$ and Ly6G$^+$ICAM4$^+$ cells (results not shown). Since, there exists a certain amount of controversy with RB6-8C5 reactivity to Ly6G and Ly6C antigens, we decided to stain MDSCs without prior sorting. As shown in FIG. 8C, unsorted BM-MDSC staining with the same antibodies gave different results. So, while GM-CSF/IL-6-derived BM-MDSCs were mostly CD11b$^+$Gr-1$^+$ (about 90% of the granular, myeloid population), a distinct sub-set of CD11b$^{hi}$Gr-1$^{lo}$ 'monocytic' population (36.6%) became evident and this population also co-stained with Ly6C (56.8%) but less so with Ly6G (18.7%), suggesting that ICAM4$^+$ cells represent the more 'monocytic' MDSC population (FIG. 8C).

Figure 9:
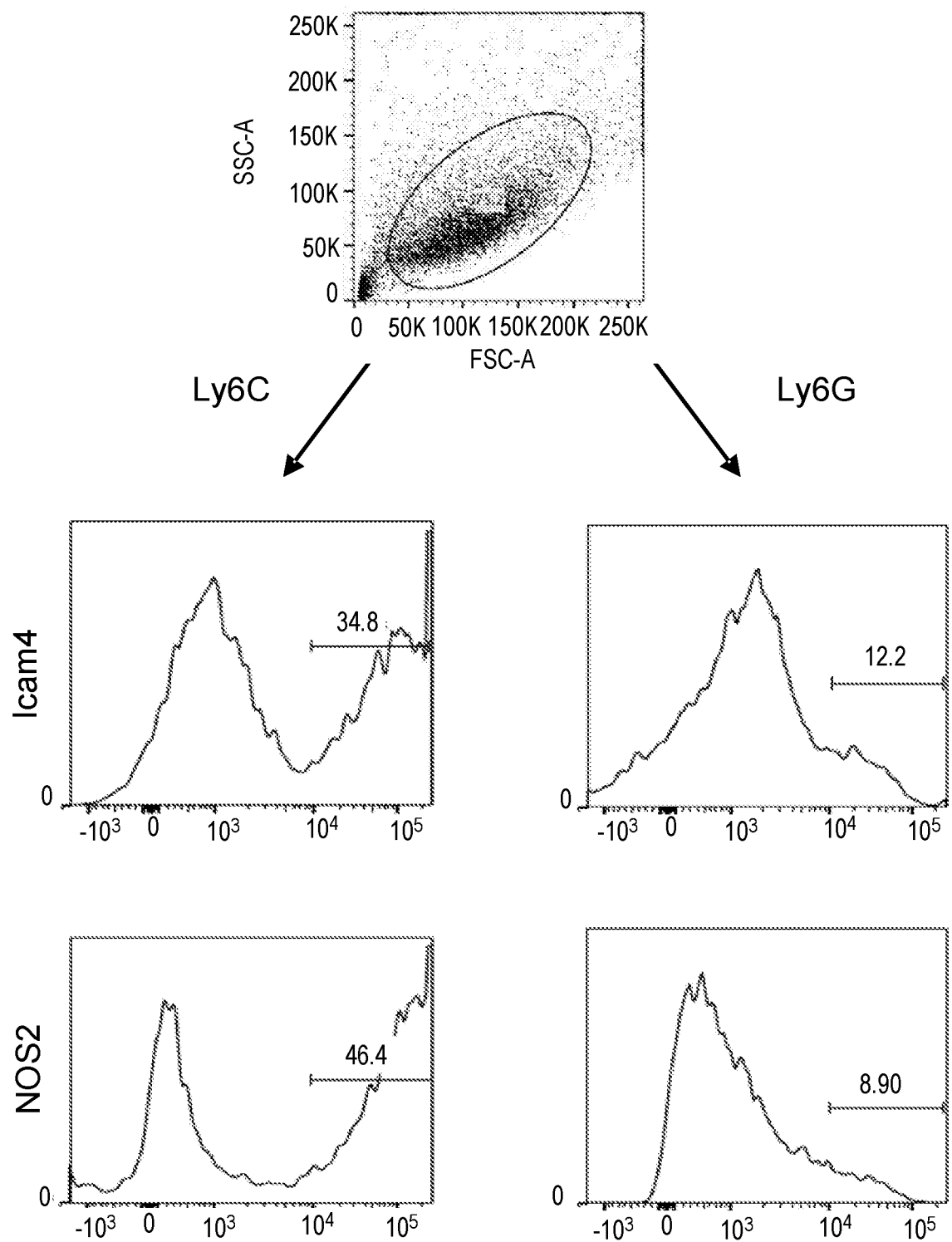
FIG. 9. Expression of ICAM4 and NOS2 in mouse MDSC. Expression of ICAM4 with Ly6C or Ly6G and NOS2 on mouse bone marrow-derived MDSC generated in vitro with GM-CSF and IL-6. MDSCs were generated from mouse BM cells as described before and then stained with antibodies to ICAM4, Ly6C, Ly6G and NOS2. Data is representative for three separate experiments.

Example 7. ICAM4$^+$ Defines a Functional Population of Immunosuppressive 'Monocytic' MDSCs While there is a lack of clear understanding on the heterogenous composition of MDSCs, there is agreement on the need for the MDSC population to be defined as immunosuppressive. A core nature of this function is the generation of reactive oxygen (ROS) or expression of arginase-1 and nitric oxide synthase (NOS2) to inactivate T cells. In order to further define the MDSC subset, we have characterized the ICAM4$^+$ MDSCs)(CD11b$^{hi}$Gr-1$^{lo}$ by staining for NOS2 expression. BM-MDSCs were generated using GM-CSF and IL-6 in culture and used for staining with antibodies to Ly6C, Ly6G, NOS2 and ICAM4. Results presented in FIG. 9 demonstrate that as shown before, ICAM4 is co-expressed mostly with Ly6C$^+$ as opposed to Ly6G$^+$ cells (34.8% and 12.2% respectively). Moreover, ICAM4 expression is associated with a population of MDSC that expresses NOS2 (48% of ICAM4$^+$NOS2$^+$) and can be classified as representing monocyte-like MDSCs (FIG. 9).

Example 8. Mouse and Human Mo-MDSCs Generated In Vitro are ICAM4$^+$NOS2$^+$

To confirm our findings on characterization of mouse Mo-MDSCs and demonstrate their equivalence to human Mo-MDSCs, we generated MDSCs from mouse BM cells and converted them into MDSCs with GM-CSF and IL-6 treatment as described earlier. Staining of these cells with antibodies to ICAM4, Gr1 and NOS2 demonstrated that the ICAM4 population co-expressed a population of NOS2 and represented a more discrete population than the heterogeneous (low, moderate to high expression) of Gr1+ cells that expressed NOS2 (FIGS. 10B and C). Similarly, we generated MDSCs from PBMC by culturing cells in the presence of GM-CSF and IL-6 and isolated CD33$^+$ cells by sorting. Staining of these cells with antibodies to ICAM4 and NOS2 revealed that ICAM4$^+$ cells also co-expressed NOS2 (FIG. 10 D-F).

Figure 11:
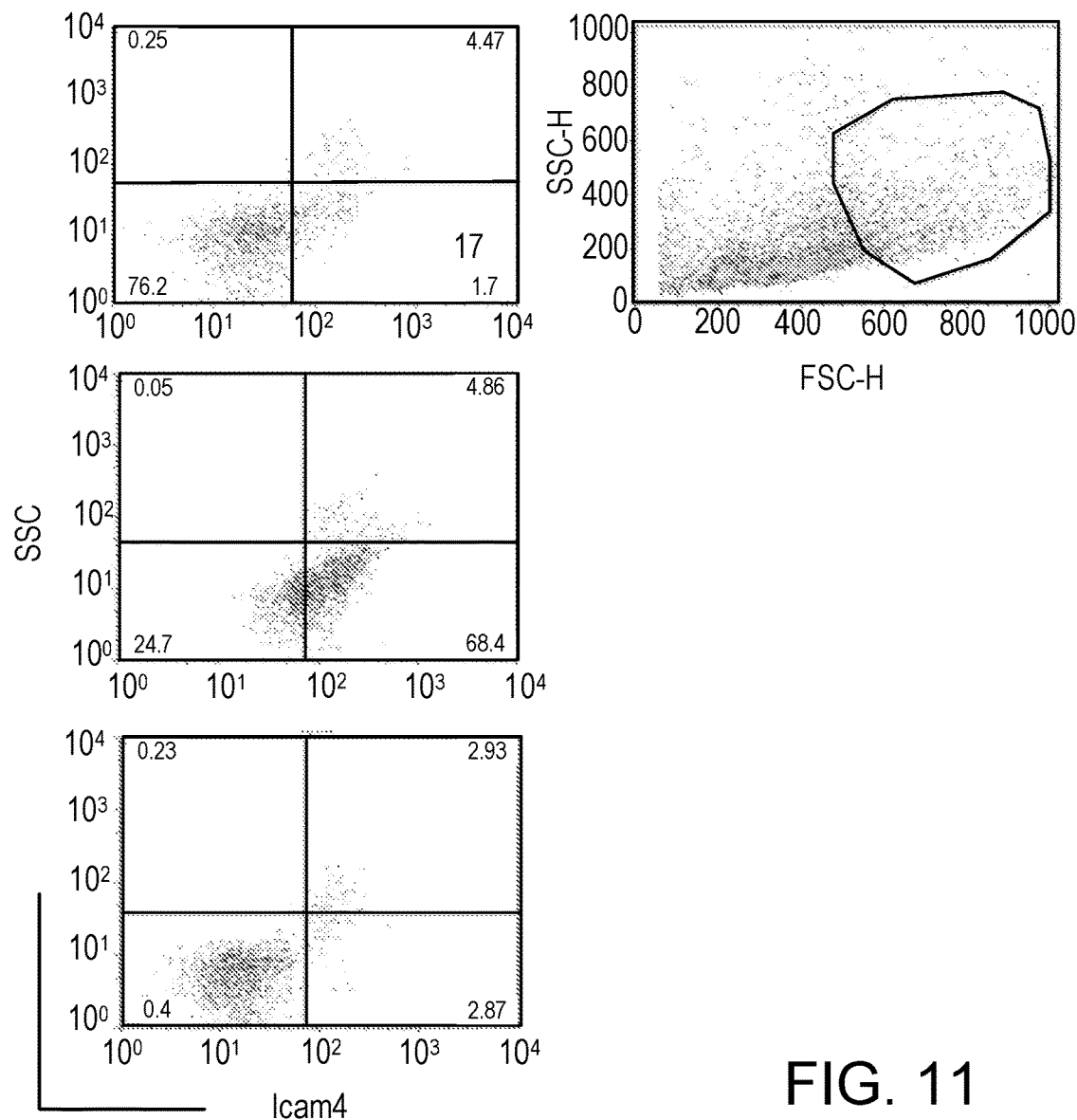
FIG. 11. Effect of combination 'metronomic' treatment of celecoxib and cyclophosphamide on outcome of Pan02 tumor growth and presence of ICAM4+ cells in spleens of tumor-bearing mice. 1×10$^6$ Pan02 cells were injected into C57Bl/6 mice s.c. and treated daily CTX+celecoxib as described in Methods. Spleen cells were harvested and stained for ICAM4 expression. Measurement of tumor volume was done at day 21. Data expressed as the mean±SEM of 5 mice per group and representative of two separate experiments.
Figure 11:
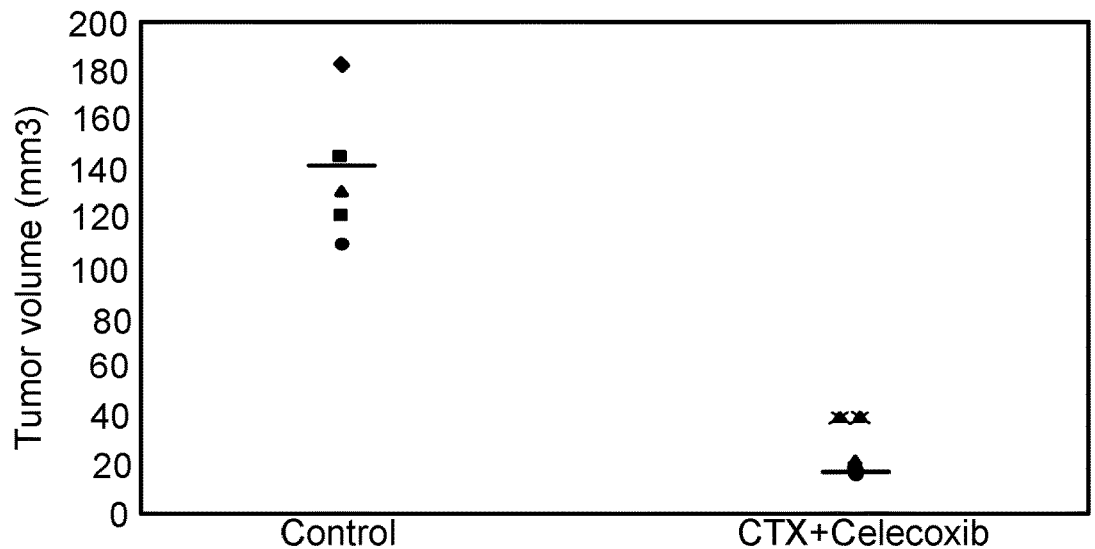
Figure 12A:
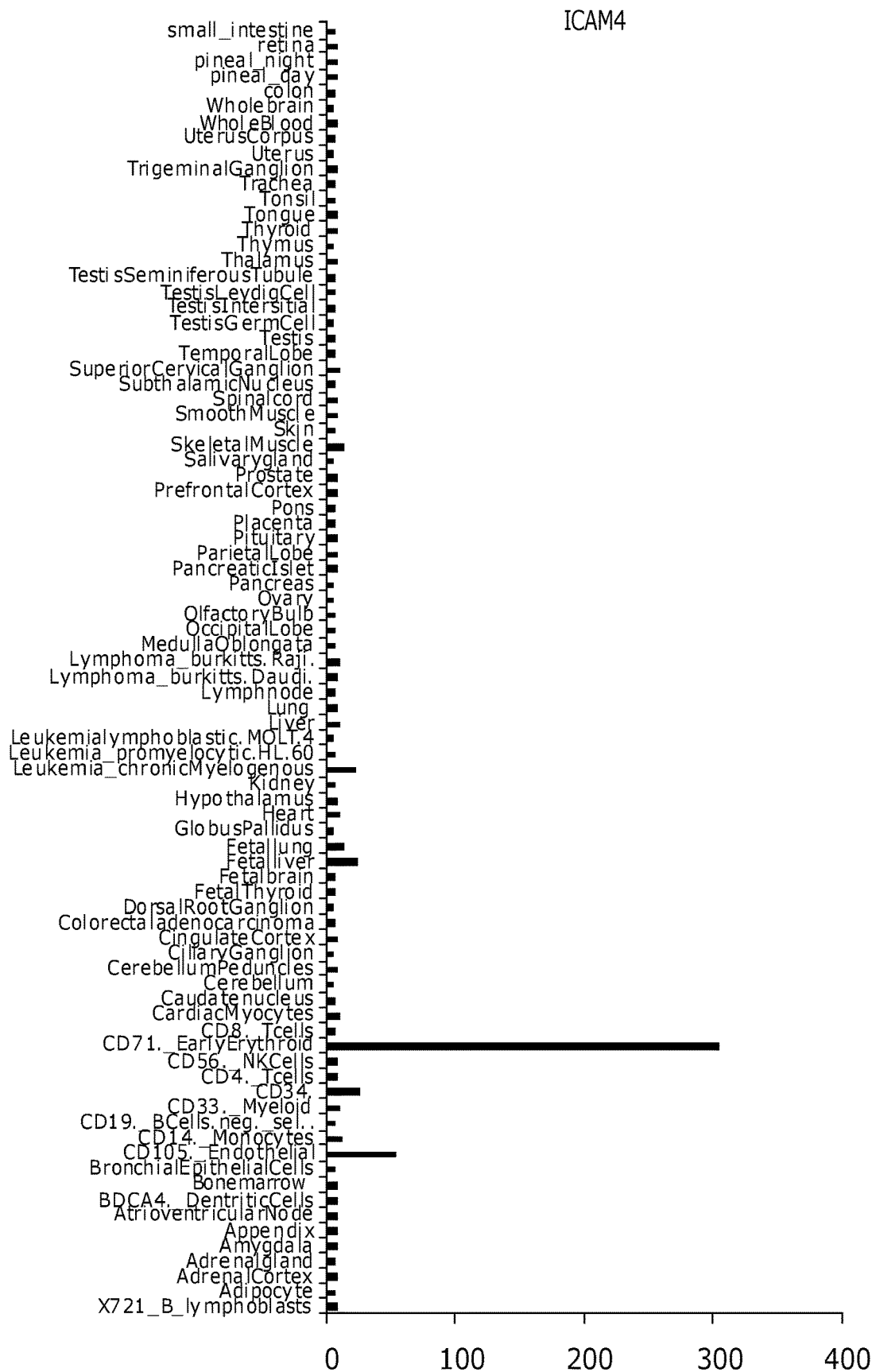
FIGS. 12A-C. Representative barplots demonstrating tissue-restricted expression of ICAM4, SPTB (FIG. 12A), RHAG, KEL (FIG. 12B), SLC2A4, SLC6A9 (FIG. 12C) genes from BioGPS Gene Atlas as described in Materials and Methods.
Figure 12A:
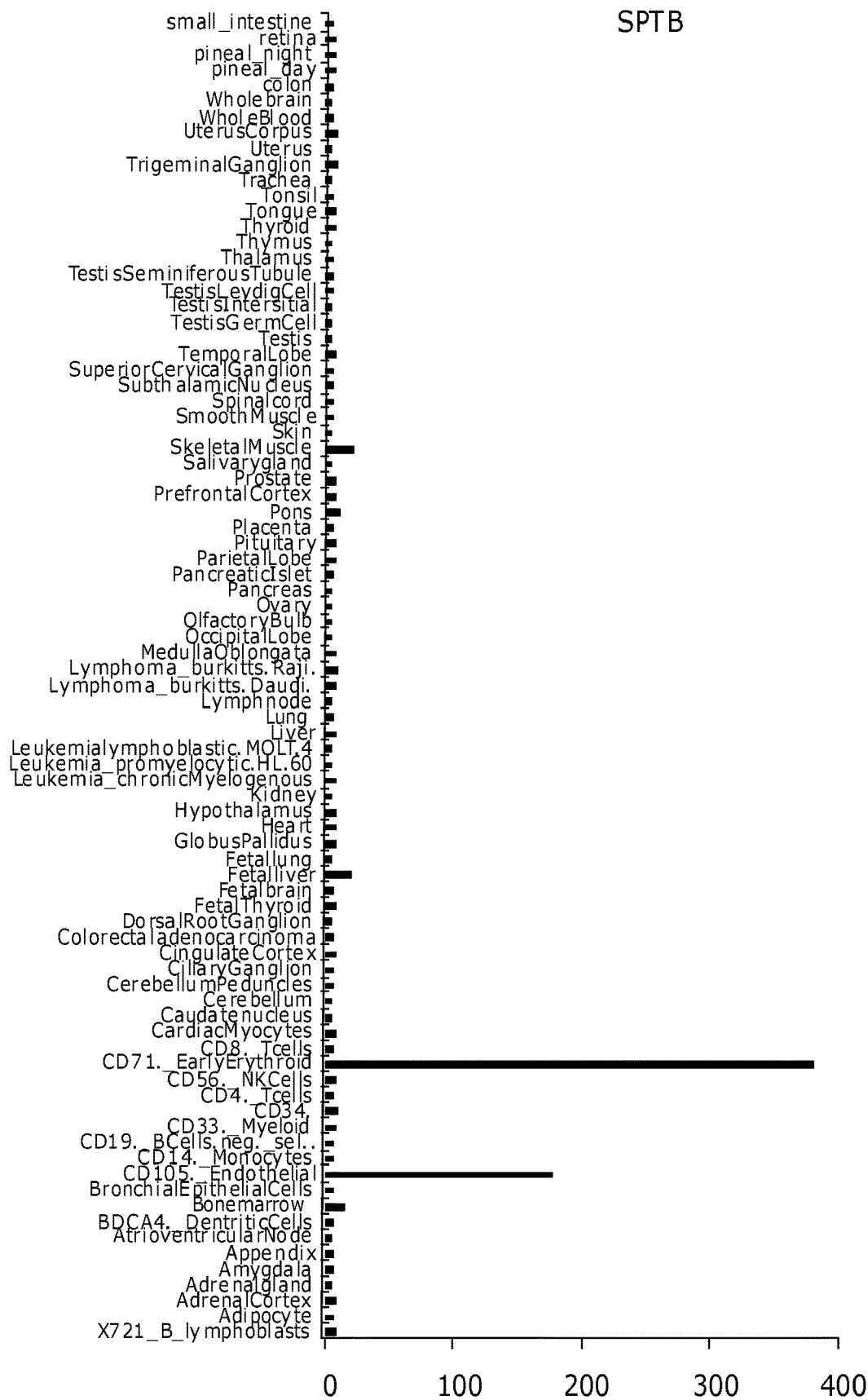
Figure 12B:
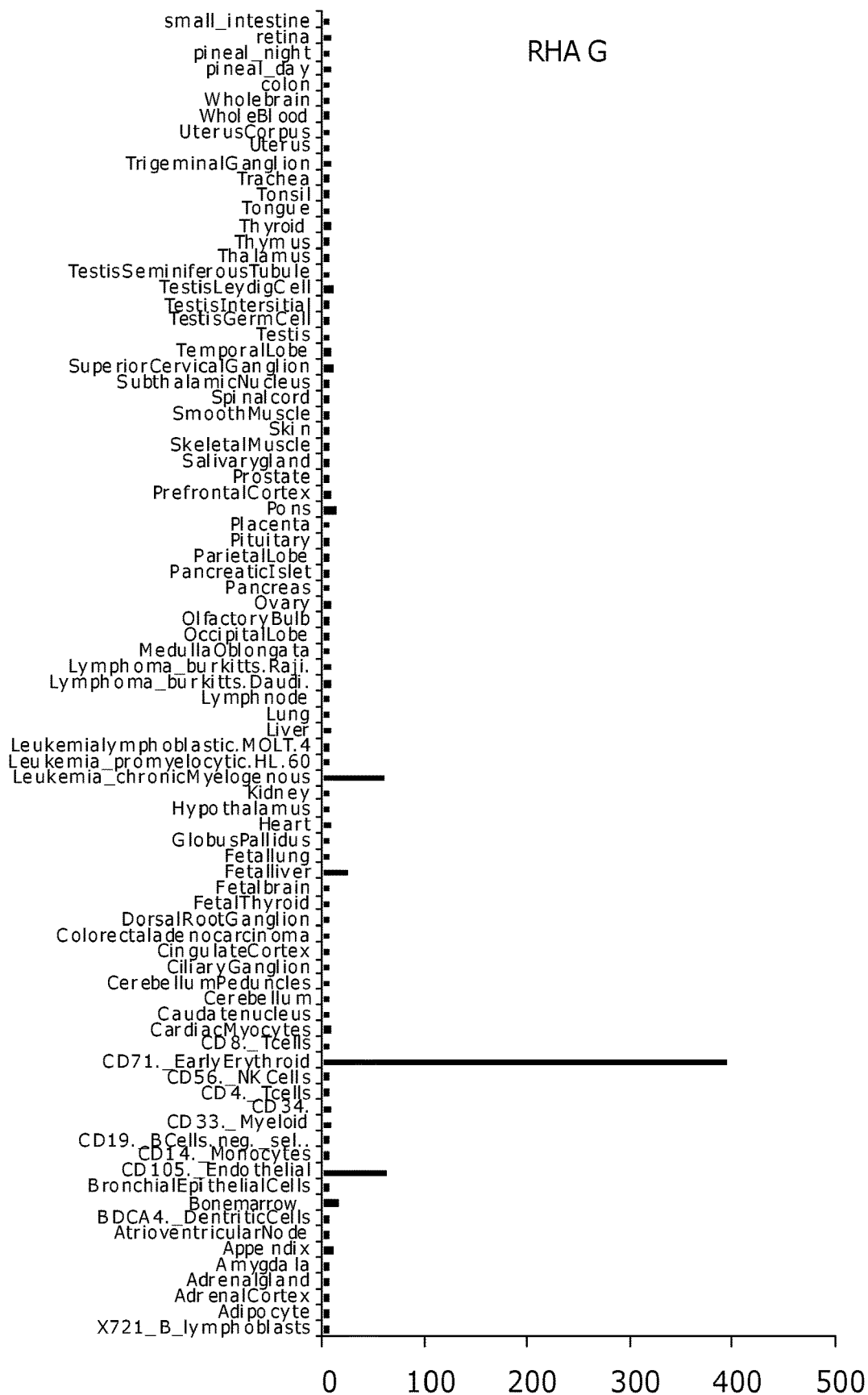
Figure 12B:
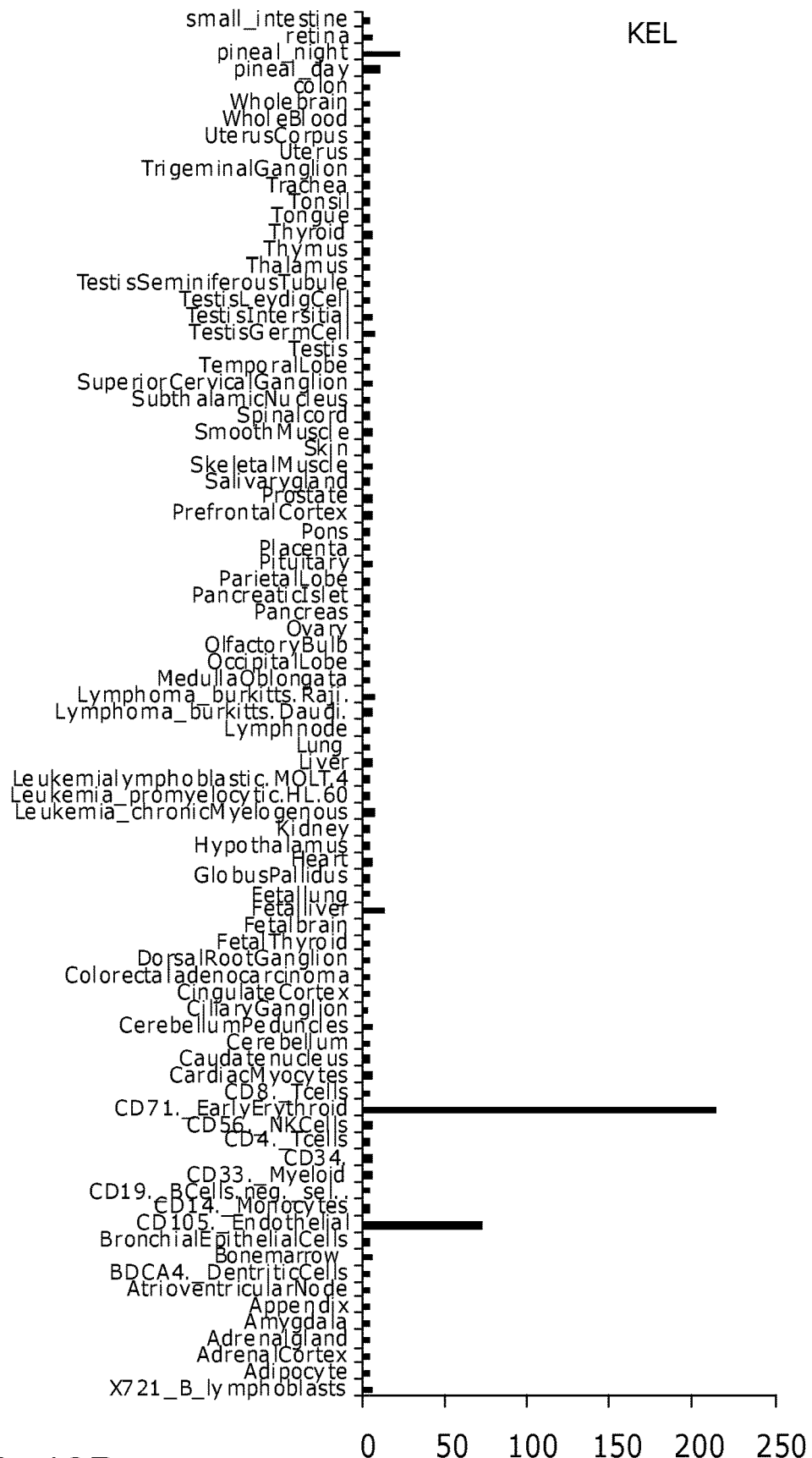
Figure 12C:
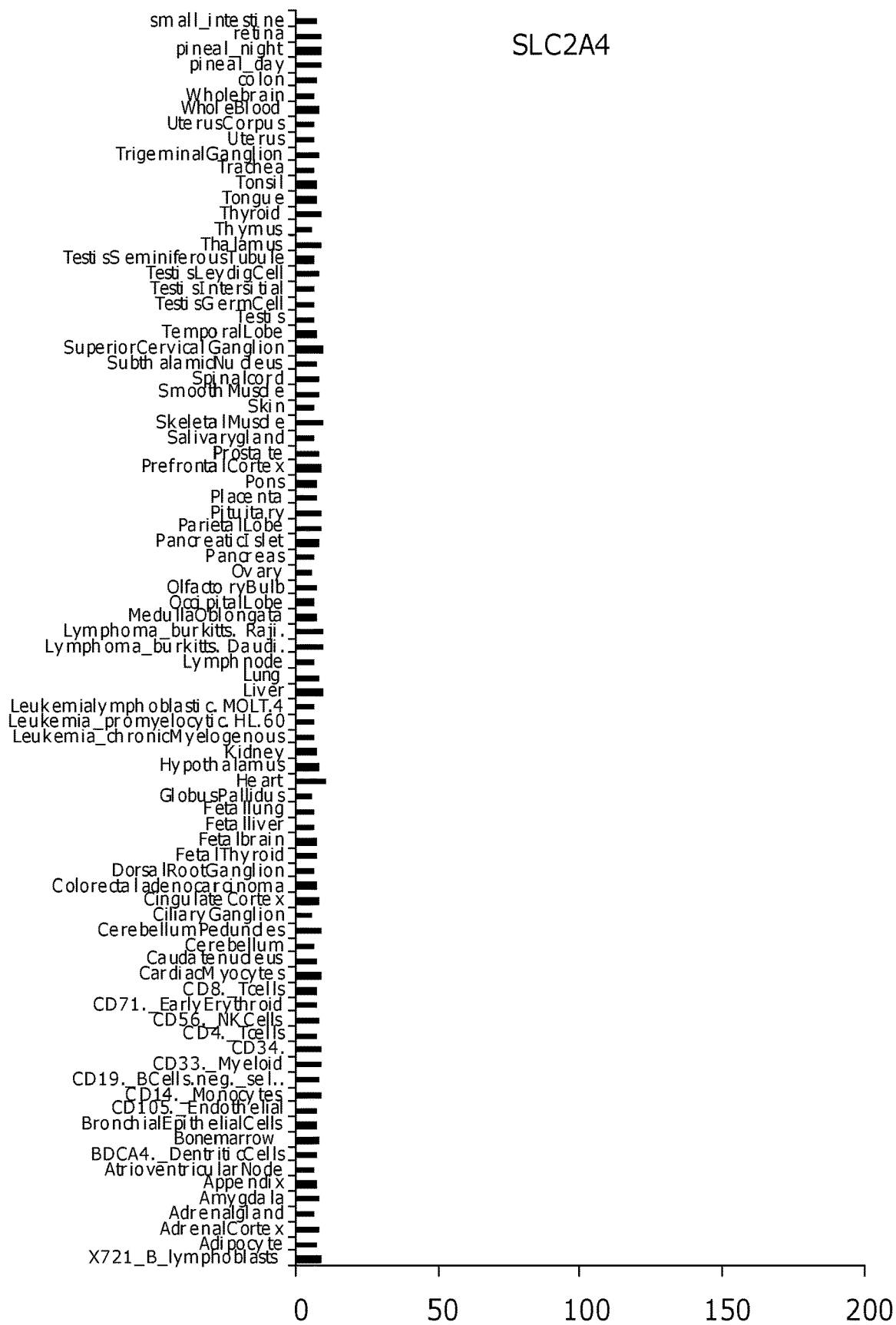
Figure 12C:
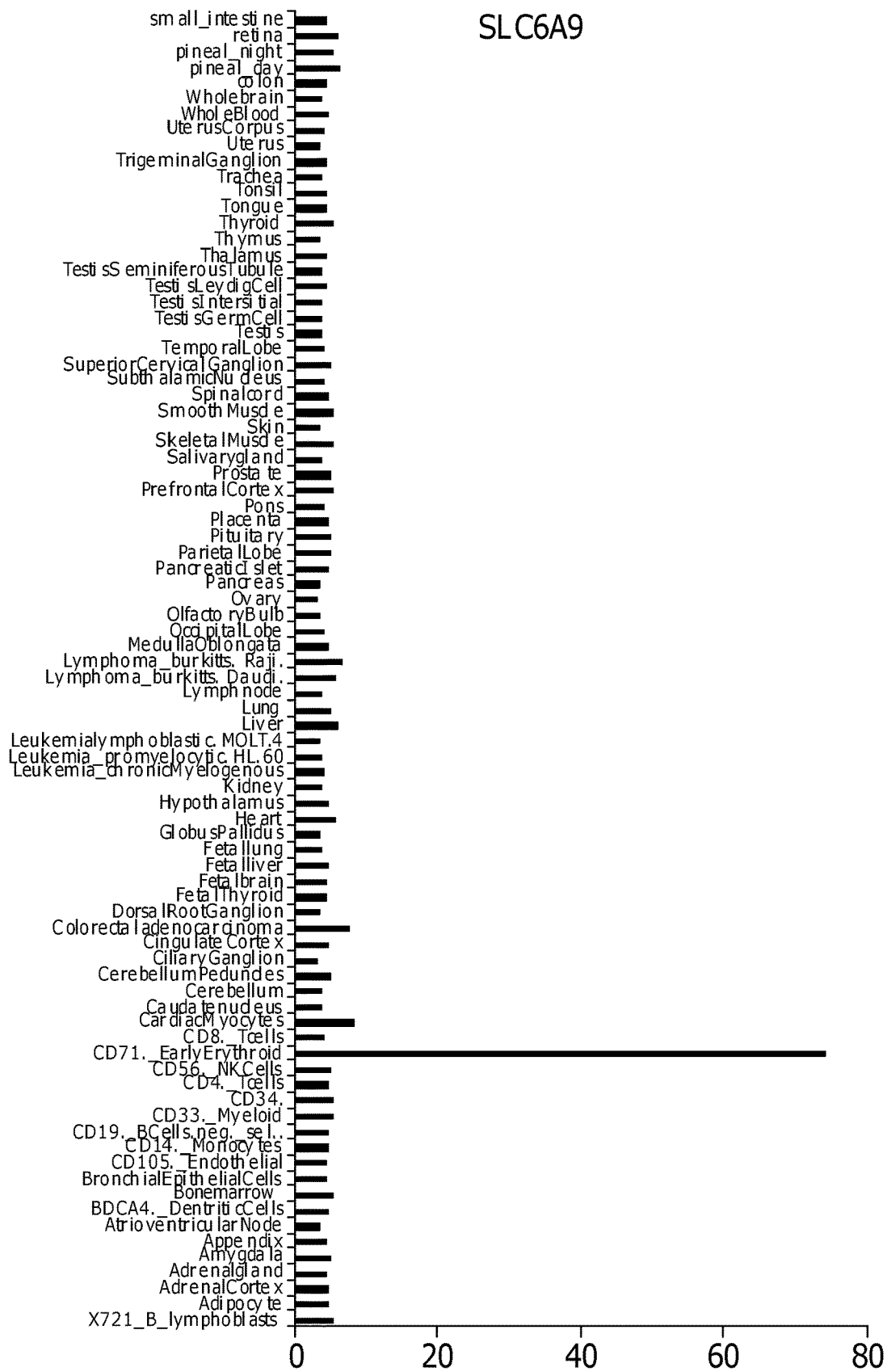

Example 9. Pharmacologic Modulation of Tumor Growth is Associated with Decreased MDSC Frequency Removal of MDSC has been shown to alleviate antitumor immunity and overall disease outcome. Our data suggested that treatment of tumor-bearing mice with 'metronomic' low-dose cyclophosphamide and a cox-2 inhibitor (Tongu et al., Cancer Immunol. Immunother. 62(2):383-91 (2013), results in slower tumor growth associated with lower numbers of MDSC and Tregs. We used this therapeutic regimen (CTX—30 mg/kg/day; celecoxib—20 mg/kg/day) to dose Pan02 tumor bearing animals and monitored tumor sizes as well as ICAM4+ MDSC levels in spleens of treated and control animals. We observed reduced tumor growth and associated decreased MDSC numbers as determined by ICAM4$^+$ cell frequencies in spleens of animals receiving this treatment (FIG. 11). Thus, in animals receiving the combination treatment, the frequency of ICAM4$^+$ cells decreased from 68.2% to 2.87% along with concomitant reduction in tumor volume (from 131.2 to 11.7 mm$^3$).

Example 10. Expression of ICAM4 in Human Cancer

The expression of ICAM4 was measured in multiple human cancer samples. Briefly, human cancer tissues analyzed for ICAM4 expression by Western blotting were obtained as lysates in RIPA buffer from Protein Biotechnologies (Protein Biotechnologies, CA).

Figure 16:
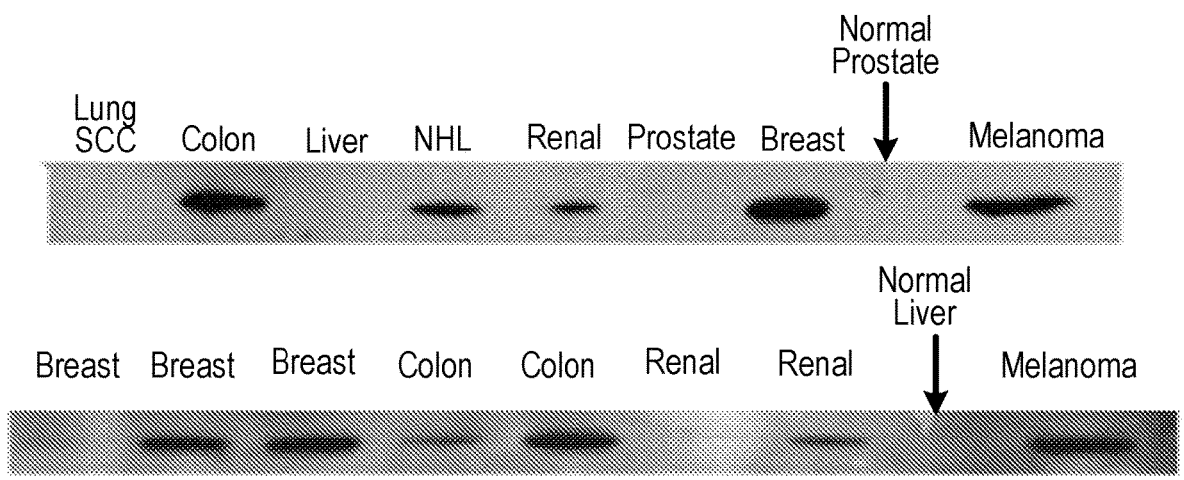
FIG. 16. Western blot analysis of ICAM4 expression in multiple primary human cancers and normal tissue lysates.

As shown in FIG. 16, Western blot analyses of tissue lysates from a majority of the human primary cancer samples revealed the presence of a protein band that corresponds to human ICAM4. Moreover, two samples of normal tissue (prostate and liver) showed no ICAM4 expression. This provides evidence of the presence of ICAM4+ cells in tumor samples from patients with various forms of cancer.

Example 11. Frequency of Circulating ICAM4+ MDSC in Prostate Cancer Patients

The frequency of ICAM4 positive MDSCs in PBMC isolated from healthy donors (HD) and prostate cancer patients (PD) was determined by FACS analysis, as follows. Blood was collected from healthy donors (n=6) and multiple prostate cancer patients (n=10). PBMC were isolated by differential density gradient separation (Ficoll-Hypaque; Sigma-Aldrich, St. Louis, Mo.) as described in Materials and Methods. Cells were labeled with HLA-DR, CD33 and ICAM4 or isotype control fluorochrome-conjugated antibodies. To calculate the percentage of ICAM4+ cells, gating was done in the Lin−, HLA-DRlo region and positive cells were considered ICAM4+ cells after subtraction of the background measured with the isotype control. Students t-test was carried out to measure significance level.

Figure 17:
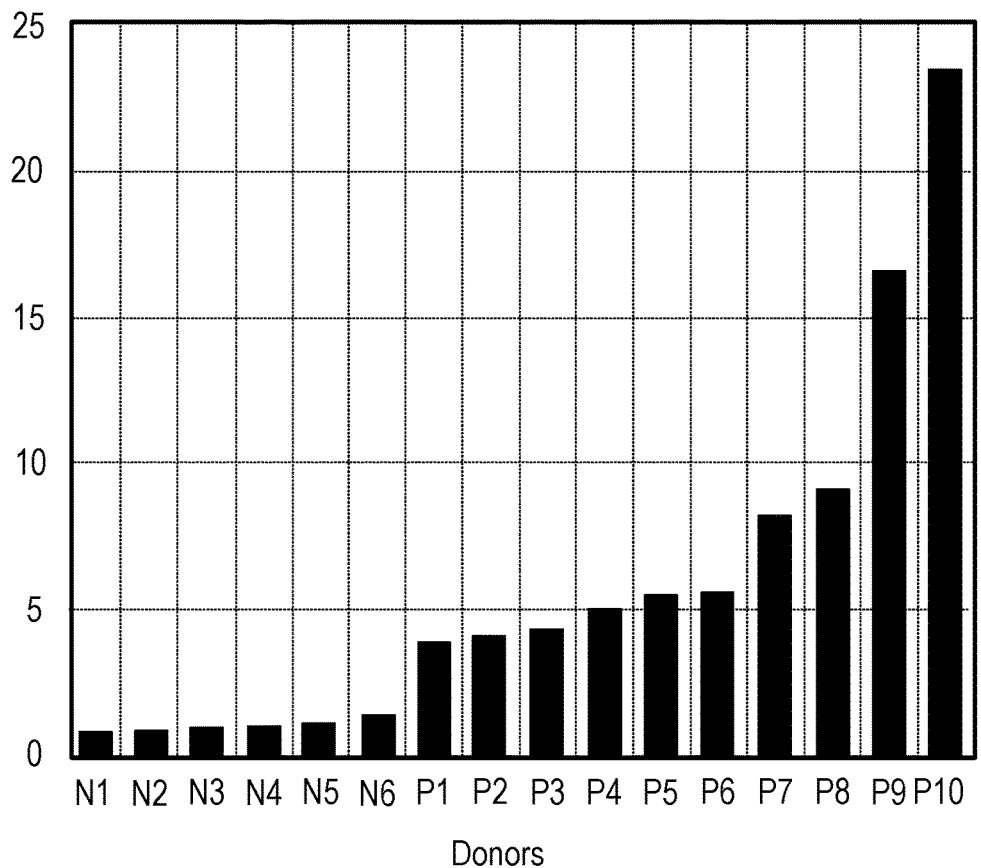
FIG. 17. Frequency of ICAM4 positive MDSCs in PBMC isolated from healthy donors (HD) and prostate cancer patients (PD) as determined by FACS analyses.

The results, presented in FIG. 17, show that all the prostate cancer patients (PD) tested had significantly higher ($p<0.01$) levels of circulating ICAM4+ MDSC as compared to healthy donors (HD).

REFERENCES

1. Young, M. R., M. Newby, and H. T. Wepsic. 1987. Hematopoiesis and suppressor bone marrow cells in mice bearing large metastatic Lewis lung carcinoma tumors. *Cancer Res.* 47:100-105.
2. Bronte, V., P. Serafini, E. Apolloni, and P. Zanovello. 2001. Tumor-induced immune dysfunctions caused by myeloid suppressor cells. *J. Immunother.* 24(431-446.
3. Gabrilovich, D. I., M. P. Velders, E. M. Sotomayor, and W. M. Kast. 2001. Mechanism of immune dysfunction in cancer mediated by immature Gr-1+ myeloid cells. *J. Immunol.* 166(9): 5398-5406.
4. Ostrand-Rosenberg, S. 2010. Myeloid-derived suppressor cells: more mechanisms for inhibiting antitumor activity. *Cancer Immunol. Immunother.* 59(10): 1593-1600.
5. Gabrilovich, D. I., and S. Nagaraj. 2009. Myeloid-derived suppressor cells as regulators of the immune system. *Nat. Rev. Immunol.* 9:162-174.
6. Clark, C. E., S. R. Hingorani, R. Mick, C. Combs, D. A. Tuveson, and R. H. Vonderheide. 2007. Dynamics of the immune reaction to pancreatic cancer from inception to invasion. *Cancer Res.* 67: 9518-9527.
7. Zhao, F., S. Obermann, M. von Wasielewski, M. Haile, M. P. Manns, F. Korangy, and T. F. Greten. 2009. Increase in frequency of myeloid-derived suppressor cells in mice with spontaneous pancreatic carcinoma. *Immunology* 128: 141-149.
8. LaFace, D., and J. Talmadge. 2011. Meeting report: regulatory myeloid cells. *Int. Immunopharmacol.* 7: 780-782.
9. Talmadge, J. E., and D. I. Gabrilovich. 2013. History of myeloid-derived suppressor cells. *Nat. Rev. Cancer.* 13(10):739-752
10. Zhao, F., B. Hoechst, A. Duffy, Gamrekelashvili, S. Fioravanti, M. P. Manns, T. F. Greten, and F. Korangy. 2012. S100A9 a new marker for monocytic human myeloid derived suppressor cells. *Immunology* 136(2): 176-183.
11. Youn, J. I., S. Nagaraj, M. Collazo, and D. I. Gabrilovich. 2008. Subsets of myeloid-derived suppressor cells in tumor-bearing mice. *J. Immunol.* 181(8):5791-5802.
12. Almand, B., J. I. Clark, E. Nikitina, J. van Beynen, N. R. English, D. P. Carbone, and D. I. Gabrilovich. 2001. Increased production of immature myeloid cells in cancer patients: a mechanism of immunosuppression in cancer. *J. Immunol.* 166(1): 678-689.
13. Mirza, N., M. Fishman, I. Fricke, M. Dunn, A. M. Neuger, T. J. Frost, R. M. Lush, S. Antonia, and D. I. Gabrilovich. 2006. All-trans-retinoic acid improves differentiation of myeloid cells and immune response in cancer patients. *Cancer Res.* 66: 9299-9307.
14. Kusmartsev, S., Z. Su, A. Heiser, J. Dannull, E. Eruslanov, H. Kübler, D. Yancey, P. Dahm, and J. Vieweg. 2008. Reversal of myeloid cell-mediated immunosuppression in patients with metastatic renal carcinoma. *Clin. Cancer Res.* 14:8270-8278.
15. Diaz-Montero, C. M., M. L. Salem, M. I. Nishimura, E.Garrett-Mayer, D. J. Cole, and A. J. Montero. 2009. Increased circulating myeloid-derived suppressor cells correlate with clinical cancer stage, metastatic tumor burden, and doxorubicin-cyclophosphamide chemotherapy. *Cancer Immunol. Immunother.* 58(1):49-59.
16. Liu, C. Y., Y. M. Wang, C. L. Wang, P. H. Feng, H. W. Ko, Y. H. Liu, Y. C. Wu, Y. Chu, F. T. Chung, C. H. Kuo, K. Y. Lee, S. M. Lin, H. C. Lin, C. H. Wang, C. T. Yu, and H. P. Kuo. 2010. Population alterations of L-arginase- and inducible nitric oxide synthase-expressed CD11b+/CD14−/CD15+/CD33+ myeloid-derived suppressor cells and CD8+T lymphocytes in patients with advanced-stage non-small cell lung cancer. *J. Cancer Res. Clin. Oncol.* 136(1):35-45.
17. Filipazzi, P., R. Valenti, V. Huber, L. Pilla, P. Canese, M. Iero, C. Castelli, L. Mariani, G. Parmiani, and L. Rivoltini. 2007. Identification of a new subset of myeloid suppressor cells in peripheral blood of melanoma patients with modulation by a granulocyte-macrophage colony-stimulation factor-based antitumor vaccine. *J. Clin. Oncol.* 25(18):2546-2553.
18. van Cruijsen, H., A. A van der Veldt, L. Vroling, D. Oosterhoff, H. J. Broxterman, R. J. Scheper, G. Giaccone, J. B. Haanen, A. J. van den Eertwegh, E. Boven, K. Hoekman, T. D. de Gruijl. 2008. Sunitinib-induced myeloid lineage redistribution in renal cell cancer patients: CD1c+ dendritic cell frequency predicts progression-free survival. *Clin. Cancer Res.* 14(18):5884-5892.
19. Vuk-Pavlović, S., P. A. Bulur, Y. Lin, R. Qin, C. L. Szumlanski, X. Zhao, and A. B. Dietz. 2010. Immunosuppressive CD14+ HLA-DRlow/− monocytes in prostate cancer. *Prostate* 70(4):443-455.
20. Nagaraj, S., and D. I. Gabrilovich. 2012. Regulation of suppressive function of myeloid-derived suppressor cells by CD4+ T cells. *Semin. Cancer Biol.* 22(4):282-288.
21. Shurin, M. R., G. V. Shurin, A. Lokshin, Z. R. Yurkovetsky, D. W. Gutkin, G. Chatta, H. Zhong, B. Han, and R. L. Ferris. 2006. Intratumoral cytokines/chemokines/growth factors and tumor infiltrating dendritic cells: friends or enemies? *Cancer Metastasis Rev.* 25(3):333-356.
22. Vieweg, J., Z. Su, P. Dahm, and S. Kusmartsev. 2007. Reversal of tumor-mediated immunosuppression. *Clin. Cancer Res.* 13(2 Pt 2):727s-732s.
23. Gottfried, E., M. Kreutz, and A. Mackensen. 2008. Tumor-induced modulation of dendritic cell function. *Cytokine Growth Factor Rev.* 19(1):65-77.
24. Husain, Z., Y. Huang, P. Seth, and V. P. Sukhatme V P. 2013. Tumor-derived lactate modifies antitumor immune response: effect on myeloid-derived suppressor cells and NK cells. *J. Immunol.* 191(3):1486-95.
25. Husain, Z., P. Seth, and V. P. Sukhatme. 2013. Tumor-derived lactate and myeloid-derived suppressor cells: Linking metabolism to cancer immunology. *Oncoimmunology.* 2(11):e26383.
26. Bronte, V., and P. Zanavello. 2005. Regulation of immune responses buy L-arginine metabolism. *Nat. Rev. Immunol.* 5:641-654.

27. Huang, B., P. Y. Pan, Q. Li, A. I. Sato, D. E. Levy, J. Bromberg, C. M. Divino, and S. H. Chen. 2006. Gr-1+ CD115+ immature myeloid suppressor cells mediate the development of tumor-induced T regulatory cells and T-cell anergy in tumor-bearing host. *Cancer Res.* 66: 1123-1131.
28. Serafini, P., S. Mgebroff, K. Noonan, and I. Borrello. 2008. Myeloid-derived suppressor cells promote cross-tolerance in B-cell lymphoma by expanding regulatory T cells. *Cancer Res.* 68: 5439-5449.
29. Pan, P. Y., G. Ma, K. J. Weber, J. Ozao-Choy, G. Wang, B. Yin, C. M. Divino, and S. H. Chen. 2010. Immune stimulatory receptor CD40 is required for T-cell suppression and T regulatory cell activation mediated by myeloid-derived suppressor cells in cancer. *Cancer Res.* 70:99-108.
30. Ugel, S., F. Delpozzo, G. Desantis, F. Papalini, F. Simonato, N. Sonda, S. Zilio, and V. Bronte. 2009. Therapeutic targeting of myeloid-derived suppressor cells. *Curr. Opin. Pharmacol.* 9(4): 470-481.
31. Kao, J., E. C., Ko, S. Eisenstein, A. G. Sikora, S. Fu, and S. H. Chen. 2011. Targeting immune suppressing myeloid-derived suppressor cells in oncology. *Crit. Rev. Oncol. Hematol.* 77(1): 12-19.
32. Terabe, M., S. Matsui, J. M. Park, M. Mamura, N. Noben-Trauth, D. D. Donaldson, W. Chen, S. M. Wahl, S. Ledbetter, B. Pratt, J. J. Letterio, W. E. Paul, and J. A. Berzofsky. 2003. Transforming growth factor-b production and myeloid cells are an effector mechanism through which CD1d restricted T cells block cytotoxic T lymphocyte-mediated tumor immunosurveillance: abrogation prevents tumor recurrence. *J. Exp. Med.* 198(11):1741-1752.
33. Zea, A. H., P. C. Rodriguez, M. B. Atkins, C. Hernandez, S. Signoretti, J. Zabaleta, D. McDermott, D. Quiceno, A. Youmans, A. O'Neill, J. Mier, and A. C. Ochoa. 2005. Arginase-producing myeloid suppressor cells in renal cell carcinoma patients: a mechanism of tumor evasion. *Cancer Res.* 65(8): 3044-3048.
34. Greten, T. F, M. P. Manns, and F. Korangy. 2011. Myeloid derived suppressor cells in human disease. *Int. Immunopharmacol.* 11(7):802-807.
35. Cerdeira, A. S., A. Rajakumar, C. M. Royle, A. Lo, Z. Husain, R. I. Thadhani, V. P. Sukhatme, S. A. Karumanchi, and H. D. Kopcow. 2013. Conversion of peripheral blood NK cells to a decidual NK-like phenotype by a cocktail of defined factors. *J. Immunol.* 190(8):3939-3948.
36. Smyth, G. K. 2004. Linear models and empirical bayes methods for assessing differential expression in microarray experiments. *Stat. Appl. Genet. Mol. Biol.* 3 (1): Article 3.
37. Benjamini, Y., and Y. Hochberg, 1995. Controlling the false discovery rate: a practical and powerful approach to multiple testing. *J R Stat Soc Series B* 57, 11.
38. Apweiler, R., A. Bairoch, C. H. Wu, W. C. Barker, B. Boeckmann, S. Ferro, E. Gasteiger, H. Huang, R. Lopez, M. Magrane, M. J. Martin, D. A. Natale, C. o'Donovan, N. Redaschi, and L. S. Yeh, 2004. UniProt: The Universal Protein knowledgebase. *Nucleic Acids Research* 32 (90001): 115D-1119.
39. Lechner, M. G., D. J. Liebertz, and A. L. Epstein. 2010. Characterization of cytokine-induced myeloid-derived suppressor cells from normal human peripheral blood mononuclear cells. *J. Immunol.* 185(4):2273-2278.
40. Marigo, I., L. Dolcetti, P. Serafini, P. Zanovello, and V. Bronte. 2008. Tumor-induced tolerance and immune suppression by myeloid derived suppressor cells. *Immunol. Rev.* 222:162-179.
41. Ostrand-Rosenberg, S., and P. Sinha. 2009. Myeloid-derived suppressor cells: linking inflammation and cancer. *J. Immunol.* 182(8):4499-4506.
42. Peranzoni, E., S. Zilio, I. Marigo, L. Dolcetti, P. Zanovello, S. Mandruzzato, and V. Bronte. 2010. Myeloid-derived suppressor cell heterogeneity and subset definition. *Curr Opinion Immunol.* 22:238-244.
43. Greifenberg, V., E. Ribechini, S. Rössner, and M. B. Lutz. 2009. Myeloid-derived suppressor cell activation by combined LPS and IFN-gamma treatment impairs DC development. *Eur. J. Immunol.* 39(10):2865-2876.
44. Ribechini, E., V. Greifenberg, S. Sandwick, and M. B. Lutz. 2010. Subsets, expansion and activation of myeloid-derived suppressor cells. *Med. Microbiol. Immunol.* 199 (3):273-281.
45. Haile, L. A., T. F. Greten, and F. Korangy. 2012. Immune suppression: the hallmark of myeloid derived suppressor cells. *Immunol. Invest.* 41(6-7):581-594.
46. Yang, R., Z. Cai, Y. Zhang, W. H. Yutzy 4th, K. F. Roby, and R. B. Roden. 2006. CD80 in immune suppression by mouse ovarian carcinoma-associated Gr-1+CD11b+ myeloid cells. *Cancer Res.* 66(13):6807-6815.
47. Huang, B., P. Y. Pan, Q. Li, A. I. Sato, D. E. Levy, J. Bromberg, C. M. Divino, and S. H. Chen. 2006. Gr-1+ CD115+ immature myeloid suppressor cells mediate the development of tumor-induced T regulatory cells and T-cell anergy in tumor-bearing host. *J Clin Invest.* 116 (10):2777-2790.
48. Gallina, G., L. Dolcetti, P. Serafini, C. De Santo, I. Marigo, M. P. Colombo, G. Basso, F. Brombacher, I. Borrello, P. Zanovello, S. Bicciato, and V. Bronte. 2006. Tumors induce a subset of inflammatory monocytes with immunosuppressive activity on CD8+ T cells. *J. Clin. Invest.* 116(10):2777-2790.
49. Zhao, F., B. Hoechst, A. Duffy, J. Gamrekelashvili, S. Fioravanti, M. P. Manns, T. F. Greten, and F. Korangy. 2012. S100A9 a new marker for monocytic human myeloid-derived suppressor cells. *Immunology* 136(2): 176-183.
50. Youn, J. I., and D. I. Gabrilovich. 2010. The biology of myeloid-derived suppressor cells: the blessing and the curse of morphological and functional heterogeneity. *Eur. J. Immunol.* 40(11):2969-2975.
51. Mielcarek, M., P. J. Martin, and B. Torok-Storb. 1997. Suppression of alloantigen-induced T-cell proliferation by CD14+ cells derived from granulocyte colony-stimulating factor-mobilized peripheral blood mononuclear cells. *Blood* 89(5):1629-1634.
52. Talmadge, J. E., E. C. Reed, A. Kessinger, C. A. Kuszynski, G. A. Perry, C. L. Gordy, K. C. Mills, M. L. Thomas, S. J. Pirruccello, B. A. Letheby, M. A. Arneson, and J. D. Jackson. 1996. Immunologic attributes of cytokine mobilized peripheral blood stem cells and recovery following transplantation. *Bone Marrow Transplant.* 17(1):101-109.
53. Singh, R. K., M. L. Varney, S. Buyukberber, K. Ino, A. G. Ageitos, E. Reed, S. Tarantolo, and J. E. Talmadge. 1999. Fas-FasL-mediated CD4+ T-cell apoptosis following stem cell transplantation. *Cancer Res.* 59(13):3107-3111.

54. Wesolowski, R., J. Markowitz, and W. E. Carson III. 2013. Myeloid derived suppressor cells—a new therapeutic target in the treatment of cancer. *J. Immuno Ther. Cancer* 1:1-11.
55. Hermand, P., P. Gane, M. Huet, V. Jallu, C. Kaplan, H. H. Sonneborn, J. P. Cartron, and P. Bailly. 2003. Red cell ICAM-4 is a novel ligand for platelet activated alpha IIbbeta 3 integrin. *J. Biol. Chem.* 278(7):4892-4898.
56. Carrero, R., I. Cerrada, E. Lledo, J. Dopazo, F. Garcia-Garcia, M-P. Rubio, C. Trigueros, A. Dorronsoro, A. Ruiz-Sauri, J. A. Montero, and P. Sepulveda. 2012. IL1β induces mesenchymal stem cells migration and leukocyte chemotaxix through NFkB. *Stem Cell Rev and Rep.* 8:905-916
57. Kammerer, S., R. B. Roth, R. Reneland, G. Marnellos, C. R. Hoyal, N. J. Markward, F. Ebner, M. Kiechle, U. Schwarz-Boeger, L. R. Griffiths, C. Ulbrich, K. Chrobok, G. Forster, G. M. Praetorius, P. Meyer, J. Rehbock, C. R. Cantor, M. R. Nelson, and A. Braun. 2004. Large-scale association study identifies ICAM gene region as breast and prostate cancer susceptibility locus. *Cancer Res.* 64(24):8906-8910.
58. Najjar, Y. G., and J. H. Finke. 2013. Clinical perspectives on targeting of myeloid derived suppressor cells in the treatment of cancer. *Front. Oncol.* 3:49-59.
59. Mundy-Bosse, B. L., G. B. Lesinski, A. C. Jaime-Ramirez, K. Benninger, M. Khan, P. Kuppusamy, K. Guenterberg, S. V. Kondadasula, A. R. Chaudhury, K. M. La Perle, M. Kreiner, G. Young, D. C. Guttridge, and W. E. Carson 3rd. 2011. Myeloid-Derived suppressor cell inhibition of the IFN response in tumor-bearing mice. *Cancer Res.* 71(15); 5101-5110.
60. Gabrilovich, D. I., S. Ostrand-Rosenberg, V. Bronte. 2012. Coordinated regulation of myeloid cells by tumours. *Nat. Rev. Immunol.* 12(4):253-268.
61. Egan, C. E., W. Sukhumavasi, A. L. Bierly, and E. Y. Denkers. 2008. Understanding the multiple functions of Gr-1(+) cell subpopulations during microbial infection. *Immunol. Res.* 40(1):35-48.
62. Iida N., A. Dzutsev, C. A. Stewart, L. Smith, N. Bouladoux, R. A. Weingarten, D. A. Molina, R. Salcedo, T. Back, S. Cramer, R. M. Dai, H. Kiu, M. Cardone, S. Naik, A. K. Patri, E. Wang, F. M. Marincola, K. M. Frank, Y. Belkaid, G. Trinchieri, and R. S. Goldszmid. 2013. Commensal bacteria control cancer response to therapy by modulating the tumor microenvironment. Science 342 (6161):967-970.
63. Ma C., T. Kapanadze, J. Gamrekelashvili, M. P. Manns, F. Korangy, and T. F. Greten. 2012. J Leukoc Biol. Anti-Gr-1 antibody depletion fails to eliminate hepatic myeloid-derived suppressor cells in tumor-bearing mice. 92(6):1199-206.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a subject, the method comprising:
    detecting a level of ICAM4+ MDSC in a sample from the subject;
    comparing the level of ICAM4+ MDSC in the sample to a reference level of ICAM4+ MDSC;
    selecting a subject who has a level of ICAM4+ MDSC above a reference level for treatment with a therapy that reduces levels of MDSCs, and
    administering the therapy that reduces levels of MDSCs to the subject.
2. The method of claim 1, wherein the cancer is a solid cancer of epithelial origin.
3. The method of claim 1, wherein the cancer is characterized by the presence of ICAM4+ myeloid derived suppressor cells (MDSC) in the cancer tissue.
4. The method of claim 1, wherein the therapy that reduces levels of MDSCs is selected from the group consisting of Phosphodiesterase-5 (PDE-5) inhibitors; Synthetic triterpenoids; Cyclooxygenase 2 (COX2) inhibitors; arginase inhibitors; NF-κB inhibitors; inhibitors of Nitric oxide synthase; inhibitors of colony stimulating factors and their receptors; histamine or H2 blockers; IL-17; all-trans retinoic acid (ATRA); Vitamin D3 or Vitamin A; TLR9 ligand agonists; Nitro-Bisphosphonates (N-Bisphosphonates); inhibitors of STAT3 activation; and platinum agents; Sunitinib; Gemcitabine; 5-Fluorouracil (5-FU); paclitaxel; heat shock protein 90 (HSP90) inhibitors; IL-13 linked to *Pseudomonas* exotoxin (IL-13-PE); and anti-Gr1+ antibodies.

* * * * *